United States Patent
Ramstedt et al.

(10) Patent No.: US 10,428,022 B2
(45) Date of Patent: Oct. 1, 2019

(54) IMINOSUGARS USEFUL FOR THE TREATMENT OF VIRAL DISEASES

(71) Applicant: Emergent Virology, LLC, Gaithersburg, MD (US)

(72) Inventors: Urban Ramstedt, Bethesda, MD (US); Kelly Lyn Warfield, Adamstown, MD (US); Anthony Treston, Rockville, MD (US)

(73) Assignee: Emergent Virology LLC, Gaithersburg, MD (US)

( * ) Notice: Subject to any disclaimer, the term of this patent is extended or adjusted under 35 U.S.C. 154(b) by 107 days.

(21) Appl. No.: 15/524,535

(22) PCT Filed: Nov. 4, 2015

(86) PCT No.: PCT/US2015/059110
§ 371 (c)(1),
(2) Date: May 4, 2017

(87) PCT Pub. No.: WO2016/073652
PCT Pub. Date: May 12, 2016

(65) Prior Publication Data
US 2018/0273473 A1    Sep. 27, 2018

Related U.S. Application Data

(60) Provisional application No. 62/075,505, filed on Nov. 5, 2014.

(51) Int. Cl.
| A61K 31/45 | (2006.01) |
| C07D 211/46 | (2006.01) |
| C07D 401/06 | (2006.01) |
| C07D 401/12 | (2006.01) |
| C07D 405/06 | (2006.01) |
| C07D 409/06 | (2006.01) |
| C07D 413/06 | (2006.01) |
| C07D 473/34 | (2006.01) |
| C07D 487/04 | (2006.01) |
| C07D 401/10 | (2006.01) |
| C07D 401/14 | (2006.01) |
| C07D 405/10 | (2006.01) |
| C07D 413/10 | (2006.01) |
| C07D 413/12 | (2006.01) |

(52) U.S. Cl.
CPC .......... C07D 211/46 (2013.01); C07D 401/06 (2013.01); C07D 401/10 (2013.01); C07D 401/12 (2013.01); C07D 401/14 (2013.01); C07D 405/06 (2013.01); C07D 405/10 (2013.01); C07D 409/06 (2013.01); C07D 413/06 (2013.01); C07D 413/10 (2013.01); C07D 413/12 (2013.01); C07D 473/34 (2013.01); C07D 487/04 (2013.01); A61K 31/45 (2013.01)

(58) Field of Classification Search
None
See application file for complete search history.

(56) References Cited

U.S. PATENT DOCUMENTS

| 4,246,345 A | 1/1981 | Kinast et al. |
| 4,266,025 A | 5/1981 | Kinast et al. |
| 4,405,714 A | 9/1983 | Kinast et al. |
| 4,806,650 A | 2/1989 | Schroder et al. |
| 4,994,572 A | 2/1991 | Fleet |
| 5,043,273 A | 8/1991 | Scudder et al. |
| 5,051,407 A | 9/1991 | Boeshagen et al. |
| 5,103,008 A | 4/1992 | Scudder et al. |
| 5,200,523 A | 4/1993 | Fleet |
| 5,622,972 A | 4/1997 | Bryant et al. |
| 6,465,487 B1 | 10/2002 | Block et al. |
| 6,545,021 B1 | 4/2003 | Mueller et al. |
| 6,689,759 B1 | 2/2004 | Jacob et al. |
| 6,809,803 B1 | 10/2004 | O'Brien et al. |
| 8,426,445 B2 | 4/2013 | Ramstedt et al. |
| 8,450,345 B2 | 5/2013 | Ramstedt et al. |
| 8,748,460 B2 | 6/2014 | Ramstedt et al. |
| 8,975,280 B2 | 3/2015 | Butters et al. |
| 2007/0275998 A1 | 11/2007 | Butters et al. |
| 2008/0138351 A1 | 6/2008 | Dwek et al. |
| 2009/0252785 A1 | 10/2009 | Pollock et al. |
| 2010/0266678 A1 | 10/2010 | Pollock et al. |
| 2011/0065752 A1 | 3/2011 | Ramstedt et al. |
| 2011/0065753 A1 | 3/2011 | Ramstedt et al. |
| 2011/0065754 A1 | 3/2011 | Ramstedt et al. |

FOREIGN PATENT DOCUMENTS

| WO | WO-9940916 A1 | 8/1999 |
| WO | WO-2004007453 A1 | 1/2004 |
| WO | WO-2006125141 A2 | 11/2006 |
| WO | WO-2006125141 A3 | 9/2007 |
| WO | WO-2007140184 A2 | 12/2007 |
| WO | WO-2007140184 A3 | 11/2008 |
| WO | WO-2010096764 A1 | 8/2010 |

(Continued)

OTHER PUBLICATIONS

Berge, S.M., et al., "Pharmaceutical Salts," Journal of Pharmaceutical Sciences 66(1):1-19, Wiley, United States (Jan. 1977).

(Continued)

*Primary Examiner* — Samantha L Shterengarts
(74) *Attorney, Agent, or Firm* — Sterne, Kessler, Goldstein & Fox, P.L.L.C.

(57) ABSTRACT

Formula IA, and their use for treating viral infections.

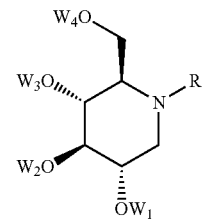

IA

21 Claims, No Drawings

(56) References Cited

FOREIGN PATENT DOCUMENTS

| WO | WO-2010144759 A1 | 12/2010 |
| WO | WO-2014143999 A1 | 9/2014 |
| WO | WO-2014179424 A2 | 11/2014 |
| WO | WO-2014179438 A2 | 11/2014 |
| WO | WO-2015039010 A2 | 3/2015 |

OTHER PUBLICATIONS

International Search Report and Written Opinion for Application No. PCT/US2015/059110, dated Mar. 21, 2016, 17 pages.

Miller, J.L., et al., "Liposome-mediated delivery of iminosugars enhances efficacy against dengue virus in vivo," Antimicrobial Agents and Chemotherapy 56(12):6379-6386, American Society for Microbiology, United States (2012).

Yu, W., et al., "Design, Synthesis, and Biological Evaluation of N-alkylated Deoxynojirimycin (DNJ) Derivatives for the Treatment of Dengue Virus Infection," Journal of Medicinal Chemistry 55(13):6061-6075, American Chemical Society, United States (2012).

Zhao, Y., et al., "Hybrids of 1-Deoxynojirimycin and Aryl-1,2,3-Triazoles and Biological Studies Related to Angiogenesis," Bioorganic & Medicinal Chemistry 16(12):6333-6337, Elsevier Science, England(Jun. 2008).

Stuart, P.T., et al., "An iminosugar with potent inhibition of dengue virus infection in vivo," *Antiviral Research* 98(1):35-43, Elsevier, Netherlands (2013).

IMINOSUGARS USEFUL FOR THE TREATMENT OF VIRAL DISEASES

RELATED APPLICATIONS

The present application claims priority to U.S. provisional application No. 62/075,505 filed Nov. 5, 2014, which is incorporated herein by reference in its entirety.

FIELD

The present application relates generally to iminosugars and in particular, to N-substituted deoxynojirimycin compounds.

SUMMARY

One embodiment may be a compound of formula IA:

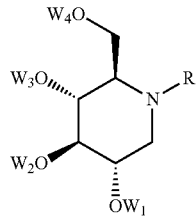

or a pharmaceutically acceptable salt thereof, wherein R may be
a)

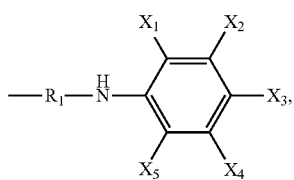

wherein one or more CH groups of the ring may be optionally substituted with N; or
b)

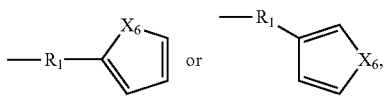

wherein $X_6$ may be O or S;
each of $W_1$-$W_4$ may be independently selected from H and $C_1$-$C_3$ alkyl group, such as methyl, ethyl and propyl;
$R_1$ may be an alkyl group, such as $C_1$-$C_{20}$ or $C_1$-$C_{12}$ alkyl group;
each of $X_1$-$X_5$ may be independently selected from the group consisting of H, $N_3$, $NO_2$, $NH_2$,

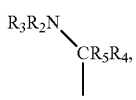

and a group comprising a heteroatom containing ring,
wherein each of $R_2$ and $R_3$ is independently selected from the group consisting of H, alkyl (such as $C_1$-$C_4$ or $C_1$-$C_3$ alkyl) or hydroxyalkyl (such as $C_1$-$C_4$ or $C_1$-$C_3$ hydroxyalkyl); $R_4$ and $R_5$ are each H, or $R_4$ and $R_5$ are together =N—OH, provided that at least one of $X_1$-$X_5$ is

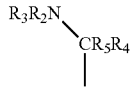

or the group comprising the heteroatom containing ring; or wherein each of $X_1$-$X_5$ is independently selected from the group consisting of H, $N_3$, $NO_2$, and $NH_2$, and wherein two of $X_1$-$X_5$, which are adjacent, form a heteroatom containing ring.

In some embodiments of the compound of formula IA, each of $W_1$-$W_4$ is hydrogen.

In some embodiments of the compound of formula IA, R may be

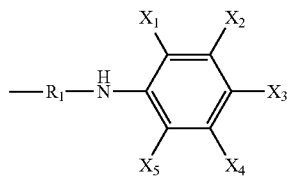

In some cases for such R, one or more CH groups of the ring of R may be optionally substituted with N. Yet in some other cases for such R, none of CH groups of the ring of R is substituted with N.

In some embodiments for such R, $R_1$ may be a $C_3$-$C_{10}$ or $C_4$-$C_9$ or $C_5$-$C_9$ or $C_5$-$C_7$ alkyl group, such as a $C_6$ alkyl group.

In some embodiments, one of $X_1$-$X_5$ may be

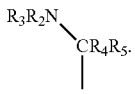

In such a case, in some embodiments, $R_2$ and $R_3$ may be each methyl and $R_4$ and $R_5$ may be each H. In some other embodiments, $R_2$ may be $C_1$-$C_3$ hydroxyalkyl, such as hydroxymethyl, hydroxyethyl or hydroxypropyl, and each of $R_3$, $R_4$ and $R_5$ may be H. Yet in some other embodiments, $R_2$ and $R_3$ are each H and $R_4$ and $R_5$ are together =N—OH.

In some embodiments, one of $X_1$-$X_5$ may be a group comprising a heteroatom containing ring. In some embodiments, such heteroatom containing ring may contain at least one ring forming atom selected from N and O.

In some embodiments, the heteroatom containing ring may be directly bound to the ring of R. Yet in some other embodiments, the heteroatom containing ring may be bound to the ring of R through $C_1$-$C_3$ alkyl group.

In some embodiments, the heteroatom containing ring may be a three, four, five, six or seven member ring. In some embodiments, the heteroatom containing ring may be a five or six member ring.

In some embodiments, the heteroatom containing ring may be a conjugated ring. Yet in some other embodiments, the heteroatom containing ring may be a non-conjugated ring.

In some embodiments, the heteroatom containing ring may comprise at least one ring forming nitrogen atom. In some embodiments, the heteroatom containing ring may comprise two or more ring forming nitrogen atoms. In some embodiments, the heteroatom containing ring contains a ring forming oxygen atom. In some embodiments, the heteroatom containing ring may comprise at least one ring forming nitrogen atom and at least one ring forming oxygen atom.

In some embodiments, the group comprising the heteroatom containing ring may be selected from the following:

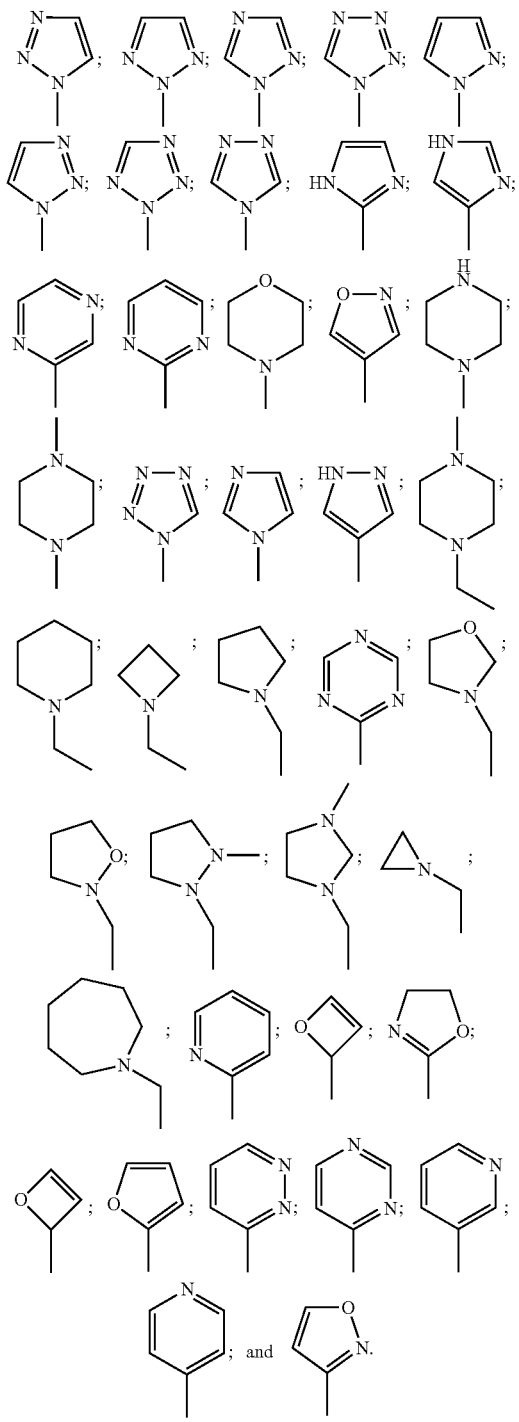

In some embodiments, $X_2$ or $X_3$ may be

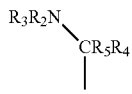

or the group comprising the heteroatom containing ring. In such a case, $X_4$ and $X_5$ may be each independently selected from H and $NO_2$, wherein at least one of $X_4$ and $X_5$ is H.

In some embodiments, $X_3$ may be

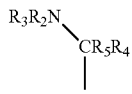

or the group comprising the heteroatom containing ring. In such a case, $X_5$ may be $NO_2$ or H.

In some embodiments, no more than two of $X_1$-$X_5$ may be not H. In some embodiments, at least two or at least three of $X_1$-$X_5$ may be H. In some embodiments, two, three or four of $X_1$-$X_5$ may be H.

In some embodiments, two of adjacent groups selected from $X_1$-$X_5$ may form a heteroatom containing ring. Such heteroatom containing ring may include one or more ring forming heteroatoms, such as N and O. For example, $X_1$ and $X_2$, $X_2$ and $X_3$, $X_3$ and $X_4$, or $X_4$ and $X_5$ may form the heteroatom containing ring. In some embodiments, $X_3$ and $X_4$ or $X_4$ and $X_5$ may form the heteroatom containing ring. In some embodiments, R may be selected from the following groups:

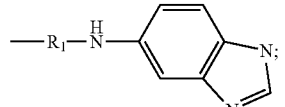

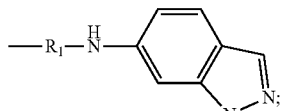

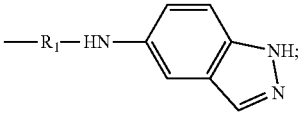

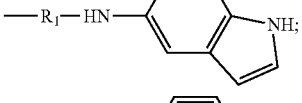

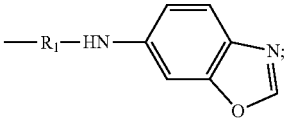

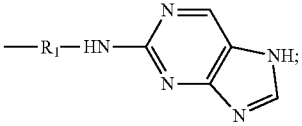

-continued

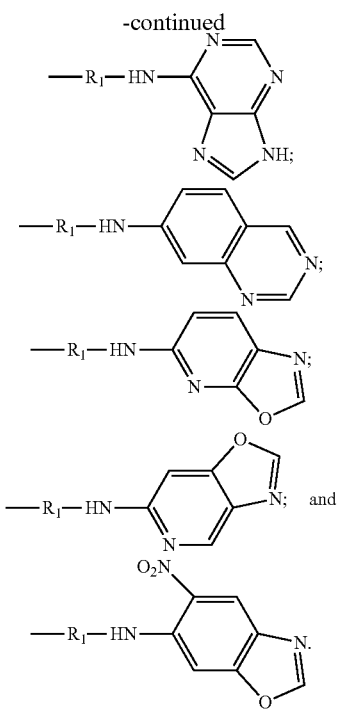

In some embodiments, those of $X_1$-$X_5$, which do not form the heteroatom containing ring, may be each H. Yet in some other embodiments, at least one of those of $X_1$-$X_5$, which do not form the heteroatom containing ring, may be $NO_2$ or $NH_2$, while the rest of $X_1$-$X_5$, which do not form the heteroatom containing ring, if any, may be H. In some embodiments, one of those of $X_1$-$X_5$, which do not form the heteroatom containing ring, may be $NO_2$ or $NH_2$, while the rest of $X_1$-$X_5$, which do not form the heteroatom containing ring, may be H.

In some embodiments, R may be

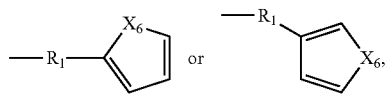

where $X_6$ may be O or S. In some embodiments, $X_6$ may be O. In some embodiments, $R_1$ may be $C_6$-$C_{10}$ alkyl. For such R, $R_1$ may be $C_4$-$C_{12}$ or $C_5$-$C_{11}$ or $C_6$-$C_{10}$ or $C_7$-$C_9$ alkyl group, such as a $C_8$ alkyl group.

Another embodiment may be a pharmaceutical composition, such as an oral pharmaceutical composition, comprising the compound of formula IA and a pharmaceutically acceptable excipient thereof.

DETAILED DESCRIPTION

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

Definition of Terms

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein may be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

In general, "substituted" refers to an alkyl, alkenyl, alkynyl, aryl, or ether group, as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

As used herein, "alkyl" groups include straight chain and branched alkyl groups having from 1 to about 20 carbon atoms, and typically from 1 to 12 carbons or, in some embodiments, from 1 to 8 carbon atoms. As employed herein, "alkyl groups" include cycloalkyl groups as defined below. Alkyl groups may be substituted or unsubstituted. Examples of straight chain alkyl groups include methyl, ethyl, n-propyl, n-butyl, n-pentyl, n-hexyl, n-heptyl, and n-octyl groups. Examples of branched alkyl groups include, but are not limited to, isopropyl, sec-butyl, t-butyl, neopentyl, and isopentyl groups. Representative substituted alkyl groups may be substituted one or more times with, for example, amino, thio, hydroxy, cyano, alkoxy, and/or halo groups such as F, Cl, Br, and I groups. As used herein the term haloalkyl is an alkyl group having one or more halo groups. In some embodiments, haloalkyl refers to a per-haloalkyl group. As used herein, cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 6, or 7. Cycloalkyl groups may be substituted or unsubstituted. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups may be mono-substituted or substituted more than once, such as, but not limited to: 2,2-; 2,3-; 2,4-; 2,5-; or 2,6-disubstituted cyclohexyl groups or mono-, di-, or tri-substituted norbornyl or cycloheptyl groups, which may be substituted with, for example, alkyl, alkoxy, amino, thio, hydroxy, cyano, and/or halo groups.

As used herein, alkenyl groups are straight chain, branched or cyclic alkyl groups having 2 to about 20 carbon atoms, and further including at least one double bond. In some embodiments alkenyl groups have from 1 to 12 carbons, or, typically, from 1 to 8 carbon atoms. Alkenyl groups may be substituted or unsubstituted. Alkenyl groups include, for instance, vinyl, propenyl, 2-butenyl, 3-butenyl, isobutenyl, cyclohexenyl, cyclopentenyl, cyclohexadienyl, butadienyl, pentadienyl, and hexadienyl groups among others. Alkenyl groups may be substituted similarly to alkyl groups. Divalent alkenyl groups, i.e., alkenyl groups with two points of attachment, include, but are not limited to, $CH-CH=CH_2$, $C=CH_2$, or $C=CHCH_3$.

As used herein, "aryl" or "aromatic," groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. The phrase "aryl groups" includes groups containing fused rings, such as fused aromatic-aliphatic ring systems (e.g., indanyl, tetrahydronaphthyl, and the like). Aryl groups may be substituted or unsubstituted.

As used herein, heteroalkyl group include straight and branched chain alkyl groups as defined above and further include 1, 2, 3, 4, 5, or 6 heteroatoms independently selected from oxygen, sulfur, and nitrogen. Thus, heteroalkyl groups include 1 to 12 carbon atoms, 1 to 10 carbons or, in some embodiments, from 1 to 8, or 1, 2, 3, 4, 5, or 6 carbon atoms, or any range therein (e.g., 1-4). Examples of heteroalkyl groups include, but are not limited to, $-(CH_2CH_2O)_{1-5}CH_3$, $-(CH_2)_{1-6}O(CH_2)_{1-6}CH_3$, $-(CH_2)_{1-6}NR_a(CH_2)_{1-6}CH_3$, $-(CH_2)_{1-6}S(CH_2)_{1-6}CH_3$, $-(CH_2)_{1-6}O(CH_2)_{1-6}O(CH_2)_{1-6}CH_3$, $-(CH_2)_{1-6}NR_a(CH_2)_{1-6}NR_a(CH_2)_{1-6}CH_3$, $-(CH_2)_{1-6}O(CH_2)_{1-6}O(CH_2)_{1-6}O(CH_2)_{1-6}CH_3$, $-(CH_2)_{1-6}NR_a(CH_2)_{1-6}NR_a(CH_2)_{1-6}NR_a(CH_2)_{1-6}CH_3$, with the total number of carbon atoms in the heteroalkyl group being 1 to 12 and $R^a$ is a hydrogen or a substituted or unsubstituted alkyl, alkenyl, aryl or aralkyl group. Other examples of heteroalkyl groups include, but are not limited to, groups having different heteroatoms in a single group. Such examples of heteroalkyl groups include, but are not limited to, $-(CH_2)_{1-6}S(CH_2)_{1-6}O(CH_2)_{1-6}$, $-(CH_2)_{1-6}NR_a(CH_2)_{1-6}O(CH_2)_{1-6}$, $-(CH_2)_{1-6}O(CH_2)_{1-6}NR_a(CH_2)_{1-6}S(CH_2)_{1-6}$, $-(CH_2)_{1-6}NR_a(CH_2)_{1-6}O(CH_2)_{1-6}S(CH_2)_{1-6}$, with the total number of carbon atoms in the heteroalkyl group being 1 to 12. In some embodiments, heteroalkyl groups include, but are not limited to, polyoxyethylene groups, such as $-(OCH_2CH_2-)_{1-5}CH_3$, for example, $-O(CH_2)_2O(CH_2)_2OCH_3$, $-O(CH_2)_2O(CH_2)_2O(CH_2)_2OCH_3$, $-O(CH_2)_2O(CH_2)_2O(CH_2)_2O(CH_2)_2OCH_3$.

As used herein, aralkyl groups are substituted aryl groups in which an alkyl group as defined above has a hydrogen or carbon bond of the alkyl group replaced with a bond to an aryl group as defined above. In some embodiments, aralkyl groups contain 7 to 14 carbon atoms, 7 to 10 carbon atoms, e.g., 7, 8, 9, or 10 carbon atoms or any range therein (e.g., 7-8). Aralkyl groups may be substituted or unsubstituted. Substituted aralkyl groups may be substituted at the alkyl, the aryl or both the alkyl and aryl portions of the group. Representative substituted and unsubstituted alkaryl groups include but are not limited to alkylphenyl such as methylphenyl, (chloromethyl)phenyl, chloro(chloromethyl)phenyl, or fused alkaryl groups such as 5-ethylnaphthalenyl. As used herein, heterocyclyl groups are non-aromatic ring compounds containing 3 or more ring members, of which one or more is a heteroatom such as, but not limited to, N, O, and S. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass partially unsaturated and saturated ring systems, such as, for example, imidazolinyl and imidazolidinyl groups. The phrase also includes bridged polycyclic ring systems containing a heteroatom such as, but not limited to, quinuclidyl. The phrase also includes heterocyclyl groups that have other groups, such as alkyl, oxo or halo groups, bonded to one of the ring members, referred to as "substituted heterocyclyl groups".

Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, pyrrolinyl, piperidyl, piperazinyl, morpholinyl, thiomorpholinyl, tetrahydropyranyl, and tetrahydrothiopyranyl groups. Representative substituted heterocyclyl groups may be mono-substituted or substituted more than once, such as, but not limited to, morpholinyl groups, which are 2-, 3-, 4-, 5-, or 6-substituted, or disubstituted with various substituents such as those listed above. The heteroatom(s) may also be in oxidized form, if chemically possible.

As used herein, heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, imidazolyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. The phrase "heteroaryl groups" includes fused ring compounds and also includes heteroaryl groups that have other groups bonded to one of the ring members, such as alkyl groups, referred to as "substituted heteroaryl groups." Representative substituted heteroaryl groups may be substituted one or more times with various substituents such as those listed above. The heteroatom(s) may also be in oxidized form, if chemically possible.

As used herein, the term "halogen" or "halo" as used herein refers to bromine, chlorine, fluorine, or iodine. In some embodiments, the halogen is fluorine. In other embodiments, the halogen is chlorine or bromine. The term "halide" as used herein refers to the anion of a halogen, such as bromide, chloride, fluoride, and iodide. In some embodiments, the halide is chloride or iodide.

As used herein, the terms "alkoxy" refers to a substituted or unsubstituted alkyl group bonded to an oxygen atom. Examples include but are not limited to methoxy and ethoxy. Representative substituted alkoxy groups may be substituted one or more times with substituents such as those listed above, such as methoxymethyl and fluoromethoxy. As used herein, the term "hydroxyalkyl" means an alkyl group terminated with one or more hydroxy groups.

As used herein, the term "conjugated" means a group, such a cyclic group or a ring, that contains at least two adjacent C atoms with $sp^2$-hybridisation (or optionally also sp-hybridisation), and wherein one or more of these C atoms may also be substituted with a heteroatom, such as N or O. In the simplest case this may be, for example, a group with alternating C—C single and double (or triple) bonds, but is also inclusive of aromatic groups.

As used herein, the term "viral infection" describes a diseased state, in which a virus invades a healthy cell, uses the cell's reproductive machinery to multiply or replicate, release of viral particles and the infection of other cells by the newly produced progeny viruses. Latent infection by certain viruses is also a possible result of viral infection. As used herein, the term "treating or preventing viral infection" means to inhibit the replication of the particular virus, to inhibit viral transmission, or to prevent the virus from establishing itself in its host, and to ameliorate or alleviate the symptoms of the disease caused by the viral infection. The treatment is considered therapeutic if there is a reduction in viral load, decrease in mortality and/or morbidity.

IC50 or IC90 (inhibitory concentration 50 or 90), also referred to as effective concentration or EC50 or EC90, is a concentration of a therapeutic agent, such as an iminosugar, used to achieve 50% or 90% reduction of viral load, respectively.

CC50 (cytotoxic concentration 50) is a concentration of a therapeutic agent, such as an iminosugar, which results in the death of 50% of the host cells.

DENV stands for Dengue virus.
VEEV stands for Venezuelan Equine Encephalitis virus.
IV stands for intravenous.
IG stands for intragastric.
IP stands for intraperitoneal.
IM stand for intramuscular.
SQ stands for subcutaneous.
PFU stands for a plaque-forming unit.
PBS stands for phosphate buffered saline.
UV-5 refers to the compound of the following formula:

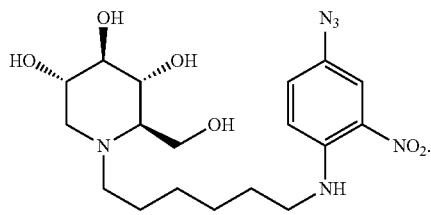

RELATED DOCUMENTS

The following patent documents, which are all incorporated herein by reference in their entirety, may be useful for understanding the present disclosure: U.S. Pat. Nos. 6,545,021; 6,809,803; 6,689,759; 6,465,487; 5,622,972; 8,450,345; 8,426,445; 8,748,460; 8,975,280; US patent application publications nos. 2011-0065754; 2011-0065753; 2011-0065752; PCT application publications nos. WO1999/040916; WO2014/143999; WO2014/179424; WO2014/179438; WO2015/039010. If any of the definitions in these documents conflicts with the definitions provided herein, the definitions provided herein control.

DISCLOSURE

The present inventors developed novel iminosugar compounds. Because the novel compounds may be classified as deoxynojirimycin derivatives, they may have at least one common utility with previously known deoxynojirimycin derivatives, such as N-butyl deoxynojirimycin, which is also known as NB-DNJ, UV-1, Zavesca® or Miglustat, or N-methoxynonyl deoxynojirimycin, which is also known as UV-4. For example, some deoxynojirimycin derivatives have demonstrated activity against at least one virus. Accordingly, the developed novel iminosugar compounds may have utility as antiviral agents.

For example, the novel iminosugar compounds, such as UV-30 and UV-60, may be effective against one or more viruses. For example, UV-30 and UV-60 may be used against a Dengue virus and/or a virus belonging to the Togaviridae family, such as Venezuelan equine encephalitis virus.

Thus, the novel iminosugar compounds, such as UV-30 and UV-60, may be useful for treating a disease or condition caused by or associated with one or more viruses. For example, UV-30 and UV-60 may be used for treating disease or condition caused by or associated with a Dengue virus and/or a virus belonging to the Togaviridae family, such as Venezuelan equine encephalitis virus. In certain embodiments, the deoxynojirimycin derivatives, such as UV-30 and UV-60, may increase a survival rate or probability for a subject infected with one or more viruses. For example, UV-30 and UV-60 may increase a survival rate or probability for a subject infected with a Dengue virus and/or a virus belonging to the Togaviridae family, such as Venezuelan equine encephalitis virus.

Dengue Viruses

Dengue virus belongs to the genus Flavivirus of the Flaviridae family and causes dengue fever. Dengue virus includes four closely related serotypes, usually referred to as Dengue 1, Dengue 2, Dengue 3 and Dengue 4. Recovery from infection by one provides lifelong immunity against that serotype but confers only partial and transient protection against infection by the other three. Good evidence exists that sequential infection increases the risk of more serious disease, including dengue shock syndrome (DSS) or dengue hemorrhagic fever (DHF). An increase in DSS/DHF cases are causing increasing concern in the Americas and in Asia, where all four dengue viruses are endemic. DSS/DHF has become a leading cause of hospitalization and death among children in several countries. In 2007, there were more than 890,000 reported cases of dengue in the Americas, of which 26,000 cases were DSS/DHF.

Dengue is transmitted primarily by the *Aedes aegypti* mosquito and is the most common mosquito-borne viral disease of humans. Globally, 2.5 billion people—40% of the world's population—live in the warm areas where *Aedes aegypti* is common and dengue can be transmitted. The rapid growth of tropical cities and their human and mosquito populations is bringing ever greater numbers of people into contact with this vector. The geographical spread of both the mosquito vectors and the virus has led to a global resurgence of epidemic dengue fever and the emergence of DSS/DHF.

Togaviridae Family

The Togaviridae family includes Genus Alphavirus and Genus Rubivirus.

Genus Alphavirus includes the following viruses: Sindbis virus; Semliki Forest virus; O'nyong'nyong virus; Chikungunya virus; Mayaro virus; Ross River virus; Barmah Forest virus; Eastern equine encephalitis virus; Western equine encephalitis virus; and Venezuelan equine encephalitis virus. Genus Rubivirus includes Rubella viruses.

Diseases and conditions that can be caused by or associated with viruses, that belong to the family Togaviridae, include, but not limited to, sindbis fever; O'nyong'nyong fever; Chikungunya disease; Ross River fever; Barmah Forest virus infection; Eastern equine encephalitis; Western equine encephalitis; Venezuelan equine encephalitis and Rubella. Animals that can be infected with a virus that belongs to the Togaviridae family, include vertebrates, such as birds and mammals including primates, humans, rodents, livestock animals, such as sheep and goats, and equines, such as horses, zebras and donkeys, as well as invertebrates.

Deoxynojirimycin Derivatives

One embodiment may be a compound of formula IA:

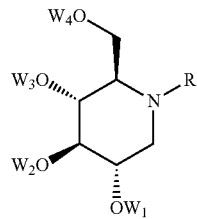

IA or a pharmaceutically acceptable salt thereof, wherein R may be a)

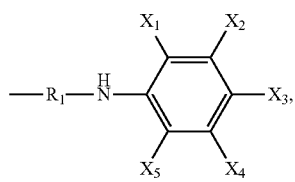

wherein one or more CH groups of the ring may be optionally substituted with N; or b)

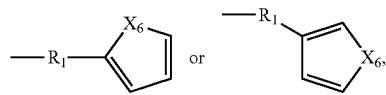

wherein $X_6$ may be O or S;

each of $W_1$-$W_4$ may be independently selected from H and $C_1$-$C_3$ alkyl group, such as methyl, ethyl and propyl;

$R_1$ may be an alkyl group, such as $C_1$-$C_{20}$ or $C_1$-$C_{12}$ alkyl group, which may be branched or unbranched;

each of $X_1$-$X_5$ may be independently selected from the group consisting of H, $N_3$, $NO_2$, $NH_2$,

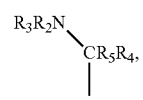

and a group comprising a heteroatom containing ring, wherein each of $R_2$ and $R_3$ is independently selected from the group consisting of H, alkyl (such as $C_1$-$C_4$ or $C_1$-$C_3$ alkyl) or hydroxyalkyl (such as $C_1$-$C_4$ or $C_1$-$C_3$ hydroxyalkyl); $R_4$ and $R_5$ are each H, or $R_4$ and $R_5$ are together =N—OH, provided that at least one of $X_1$-$X_5$ is

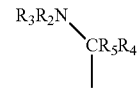

or the group comprising the heteroatom containing ring; or wherein each of $X_1$-$X_5$ is independently selected from the group consisting of H, $N_3$, $NO_2$, and $NH_2$, and wherein two of $X_1$-$X_5$, which are adjacent, form a heteroatom containing ring.

In some embodiments, none of $X_1$-$X_5$ is $N_3$.
In some embodiments, none of $X_1$-$X_5$ is $NH_2$.
In some embodiments, none of $X_1$-$X_5$ is either $N_3$ or $NH_2$.
In some embodiments of the compound of formula IA, each of $W_1$-$W_4$ is hydrogen.
In some embodiments of the compound of formula IA, R may be

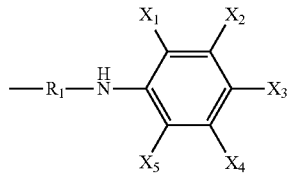

In some cases for such R, one or more ring forming CH groups of the ring of R may be optionally substituted with N. Non-limiting examples of such compounds include compounds 0102, 0105, 0106, 0107, 0108, 0109, 0110, 0122, 0123 from Table 1 below. Yet in some other cases for such R, none of the ring forming CH groups of the ring of R is substituted with N. Non-limiting examples of of such compounds include compounds 0047, 0060, 0069, 0073, 0077, 0079, 0080, 0081, 0082, 0083, 0084, 0086, 0087, 0088, 0089, 0090, 0098, 0099, 0100, 0101, 0103, 0104, 0124, 0125, 0126, 0127, 0128, 0129, 0130, 0131, 0132, 0133, 0134, 0135, 0136, 0139, 0142. 0143, 0153, 0154, 0157, 0158, 0160, 0162, 0163, 0164, 0165, 0166, 0167, 0168, 0177, 0178, 0179, 0180, 0181, 0182, 0183, 0184, 0185, 0188, 0198, 0241, 0242, 0243, 0244, 0245 and 0246 from Table 1 below.

In some embodiments for such R, $R_1$ may be $C_3$-$C_{10}$ or $C_4$-$C_9$ or $C_5$-$C_9$ or $C_5$-$C_7$ alkyl group, such as a $C_6$ alkyl group. In certain embodiments, $R_1$ may be an unbranched $C_3$-$C_{10}$ or $C_4$-$C_9$ or $C_5$-$C_9$ or $C_5$-$C_7$ alkyl group, such as an unbranched $C_6$ alkyl group.

In some embodiments, one of $X_1$-$X_5$ may be

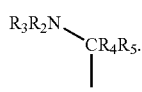

In such a case, in some embodiments, $R_2$ and $R_3$ may be each methyl and $R_4$ and $R_5$ may be each H. In some other embodiments, $R_2$ may be $C_1$-$C_3$ hydroxyalkyl, such as hydroxymethyl, hydroxyethyl or hydroxypropyl, and each of $R_3$, $R_4$ and $R_5$ may be H. Yet in some other embodiments, $R_2$ and $R_3$ are each H and $R_4$ and $R_5$ are together =N—OH.

In some embodiments, one of $X_1$-$X_5$ may be a group comprising a heteroatom containing ring. In some embodiments, such heteroatom containing ring may contain at least one ring forming atom selected from N and O.

In some embodiments, the heteroatom containing ring may be directly bound to the ring of R. Non-limiting examples of such compounds include compounds 0047, 0060, 0069, 0077, 0079, 0080, 0081, 0082, 0083, 0084, 0087, 0088, 0089, 0090, 0106, 0107, 0108, 0109, 0110, 0125, 0126, 0127, 0128, 0129, 0130, 0131, 0132, 0133, 0134, 0135, 0139, 0142, 0143, 0158, 0160, 0166, 0183, 0184, 0185, 0188, 0198, 0241, 0242, 0243, 0244, 0245 from Table 1 below.

Yet in some other embodiments, the heteroatom containing ring may be bound to the ring of R through $C_1$-$C_3$ alkyl group. Non-limiting examples of such compounds include compounds 0153, 0154, 0162, 0163, 0164, 0165, 0177, 0178, 0179, 0180, 0181, 0182 from Table 1 below.

In some embodiments, the heteroatom containing ring may be a three, four, five, six, seven or eight member ring. In some embodiments, the heteroatom containing ring may be a five or six member ring.

In some embodiments, the heteroatom containing ring may be a conjugated ring, which may be, for example, a four, five or six member conjugated ring. Non-limiting examples of such compounds include compounds, 0047, 0060, 0069, 0077, 0079, 0080, 0081, 0082, 0083, 0084, 0086, 0087, 0088, 0089, 0090, 0106, 0107, 0108, 0109, 0110, 0125, 0126, 0127, 0128, 0130, 0131, 0132, 0142, 0143, 0157, 0158, 0160, 0166, 0183, 0184, 0185, 0188, 0198, 0241, 0243, 0244, 0245 from Table 1 below.

Yet in some other embodiments, the heteroatom containing ring may be a non-conjugated ring, which may be a three, four, five, six or seven member ring. Non-limiting examples of such compounds include compounds 0129, 0133, 0134, 0135, 0139, 0153, 0154, 0162, 0163, 0164, 0165, 0177, 0178, 0179, 0180, 0181, 0182 from Table 1 below.

In some embodiments, the heteroatom containing ring may comprise at least one ring forming nitrogen atom. Non-limiting examples of such compounds include compounds 0047, 0060, 0077, 0079, 0080, 0081, 0082, 0083, 0084, 0087, 0088, 0089, 0090, 0106, 0107, 0108, 0109, 0110, 0125, 0126, 0127, 0128, 0129, 0130, 0131, 0132, 0133, 0134, 0135, 0139, 0142, 0143, 0153, 0154, 0157, 0158, 0159, 0160, 0162, 0163, 0164, 0165, 0166, 0177, 0178, 0179, 0180, 0181, 0182, 0183, 0184, 0185, 0188, 0198, 0241, 0242, 0243, 0244, 0245 from Table 1 below.

In some embodiments, the heteroatom containing ring may comprise two or more ring forming nitrogen atoms. Non-limiting examples of such compounds include 0047, 0060, 0077, 0079, 0080, 0081, 0082, 0083, 0084, 0087, 0088, 0089, 0090, 0106, 0107, 0108, 0109, 0110, 0125, 0126, 0127, 0128, 0131, 0132, 0133, 0134, 0135, 0139, 0142, 0143, 0153, 0157, 0158, 0159, 0160, 0162, 0166, 0179, 0180, 0188, 0241, 0242 from Table 1 below.

In some embodiments, the heteroatom containing ring contains a ring forming oxygen atom. Non-limiting examples of such compounds include 0069, 0129, 0130, 0154, 0177, 0178, 0184, 0185, 0198, 0245 from Table 1 below.

In some embodiments, the heteroatom containing ring may comprise at least one ring forming nitrogen atom and at least one ring forming oxygen atom. Non-limiting examples of such compounds include 0129, 0130, 0154, 0177, 0178, 0184, 0185, 0198, 0245 from Table 1 below.

In some embodiments, the heteroatom containing ring may be a substituted ring, i.e. a ring containing at least one substituent, such as a $C_1$-$C_3$ alkyl group. In some embodiments, such substituent may be on a heteroatom of the heteroatom containing ring. Non-limiting examples of such compounds include compounds 0135, 0139, 0162, 0179, 0180 from Table 1 below.

In some embodiments, the group comprising the heteroatom containing ring may be selected from the following:

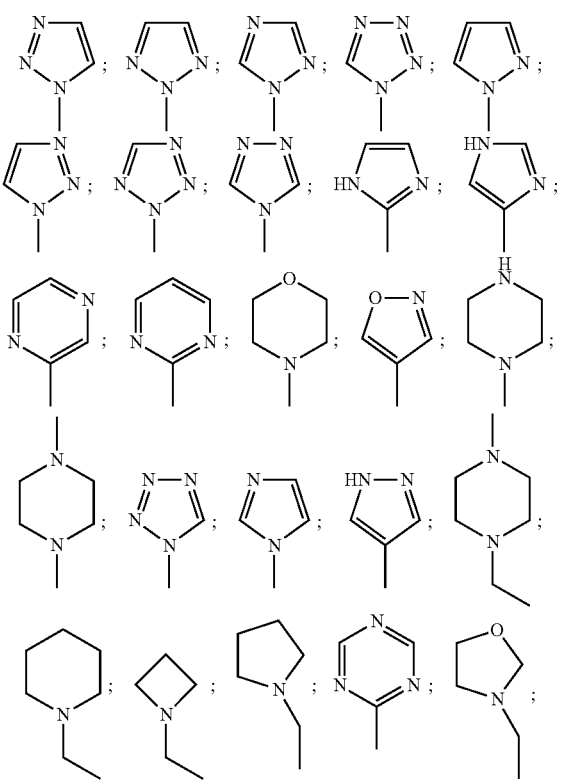

-continued

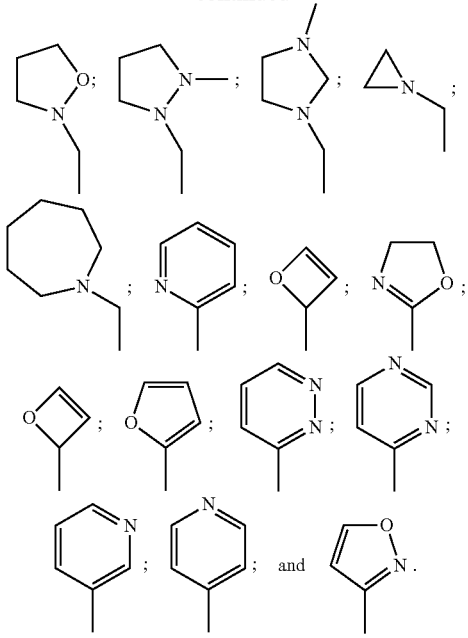

In some embodiments, one of $X_2$ and $X_3$ may be

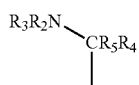

or the group comprising the heteroatom containing ring. In such a case, the other of $X_2$ and $X_3$ may be H. In certain embodiments, $X_4$ and $X_5$ may be each independently selected from H and $NO_2$, wherein at least one of $X_4$ and $X_5$ is H. For example, in some embodiments, $X_4$ may be $NO_2$ and $X_5$ may be H. In some embodiments, $X_4$ may be H and $X_5$ may be $NO_2$. In some embodiments, $X_4$ and $X_5$ may be both H. $X_1$ may be H.

In some embodiments, $X_3$ may be

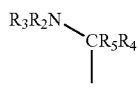

or the group comprising the heteroatom containing ring. In such a case, $X_5$ may be $NO_2$ or H. $X_1$, $X_2$ and $X_4$ may be each H.

In some embodiments, no more than two of $X_1$-$X_5$ may be not H. In some embodiments, at least two or at least three of $X_1$-$X_5$ may be H. In some embodiments, two, three or four of $X_1$-$X_5$ may be H.

In some embodiments, two of adjacent groups selected from $X_1$-$X_5$ may form a heteroatom containing ring, i.e. a ring containing at least one ring forming heteroatom, which may be, for example, N or O. The heteroatom containing ring may be, for example, a conjugated heteroatom containing ring.

In some embodiments, the heteroatom containing ring may be a nitrogen containing ring.

In some embodiments, the heteroatom containing ring may be a five or six member ring.

In some embodiments, the remaining of $X_1$-$X_5$ may be each H. Yet in some other embodiments, at least one of the remaining of $X_1$-$X_5$ may be selected from $N_3$, $NO_2$, and $NH_2$. In some embodiments, one of the remaining of $X_1$-$X_5$ may be $NO_2$, while the rest two of $X_1$-$X_5$ may be each H.

In some embodiments, $X_1$ and $X_2$, $X_2$ and $X_3$, $X_3$ and $X_4$, or $X_4$ and $X_5$ may form the heteroatom containing ring. Yet in some embodiments, $X_3$ and $X_4$ or $X_4$ and $X_5$ may form the heteroatom containing ring. In such a case, in some embodiments, the remaining three of $X_1$-$X_5$ may be each H. Yet in some other embodiments, one of the remaining of $X_1$-$X_5$, e.g. $X_1$ may be $NO_2$, while the remaining two may be each H.

In some embodiments, the heteroatom containing ring may comprise at least two ring forming nitrogens.

In some embodiments, the heteroatom containing ring may also include at least one ring forming oxygen atom.

In some embodiments, the heteroatom containing ring may include at least one ring forming nitrogen and at least one ring forming oxygen.

Non-limiting examples of the compounds, in which two of adjacent groups selected from $X_1$-$X_5$ may form a heteroatom containing ring, include compounds 0098, 0099, 0100, 0101, 0102, 0103, 0104, 0105, 0122, 0123, 0124 from Table 1 below.

In some embodiments, R may be selected from the following groups:

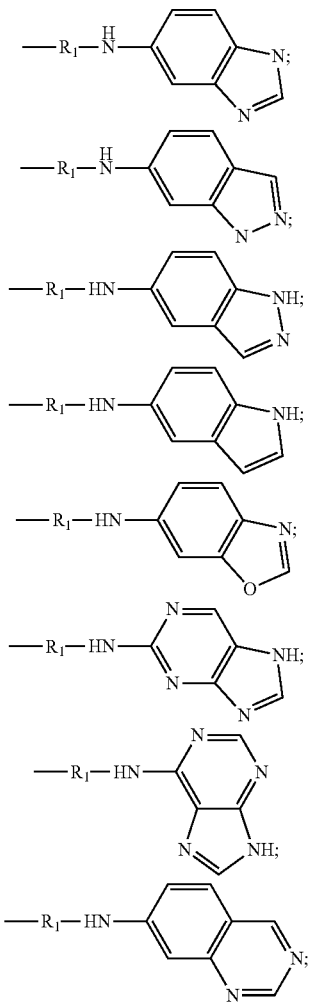

-continued

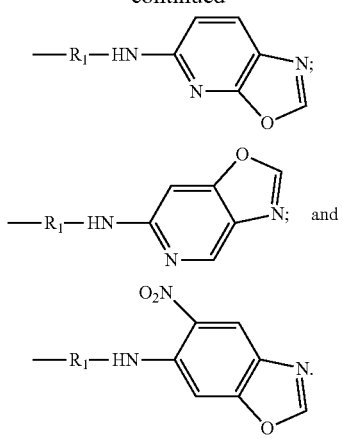

In some embodiments, those of $X_1$-$X_5$, which do not form the heteroatom containing ring, may be each H. Yet in some other embodiments, at least one of those of $X_1$-$X_5$, which do not form the heteroatom containing ring, may be $NO_2$ or $NH_2$, while the rest of $X_1$-$X_5$, which do not form the heteroatom containing ring, if any, may be H. In some embodiments, one of those of $X_1$-$X_5$, which do not form the heteroatom containing ring, may be $NO_2$ or $NH_2$, while the rest of $X_1$-$X_5$, which do not form the heteroatom containing ring, may be H.

In some embodiments, R may be

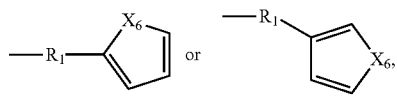

where $X_6$ may be O or S. In some embodiments, $X_6$ may be O. In some embodiments, $R_1$ may $C_6$-$C_{10}$ alkyl. For such R, $R_1$ may be $C_4$-$C_{12}$ or $C_5$-$C_{11}$ or $C_6$-$C_{10}$ or $C_7$-$C_9$ alkyl group, such as a $C_8$ alkyl group. In certain embodiments, $R_1$ may be $C_4$-$C_{12}$ or $C_5$-$C_{11}$ or $C_6$-$C_{10}$ or $C_7$-$C_9$ unbranched alkyl group, such as an unbranched $C_8$ alkyl group.

In some embodiments, the compound of formula IA may be a compound presented in Table 1.

TABLE 1

Representative compounds

| Compound Code | Compound Structure |
|---|---|
| 0030 | 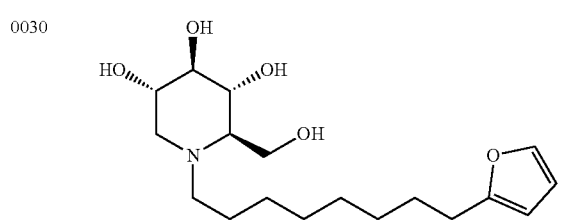 |

TABLE 1-continued

Representative compounds

| Compound Code | Compound Structure |
|---|---|
| 0031 | 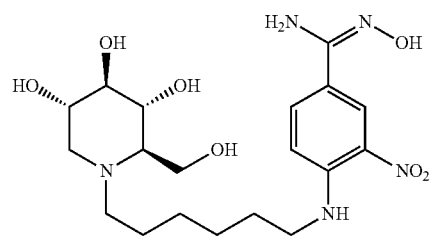 |
| 0047 | 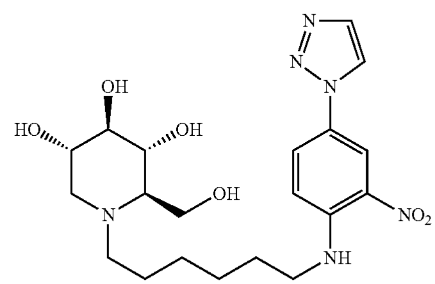 [SMILES: O=[N+]([O-])c1cc(-n2ccnn2)ccc1NCCCCCCN1C[C@H](O)[C@@H](O)[C@H](O)[C@H]1CO] |
| 0060 | 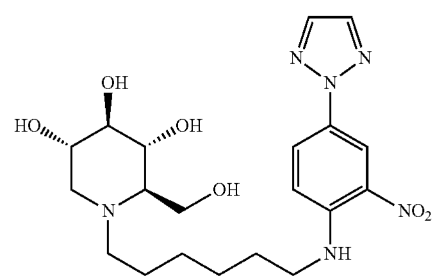 [SMILES: O=[N+]([O-])c1cc(-n2nccn2)ccc1NCCCCCCN1C[C@H](O)[C@@H](O)[C@H](O)[C@H]1CO] |
| 0069 | 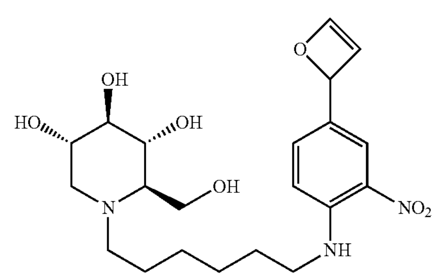 [SMILES: O=[N+]([O-])c1cc(C2C=CO2)ccc1NCCCCCCN1C[C@H](O)[C@@H](O)[C@H](O)[C@H]1CO] |
| 0073 | 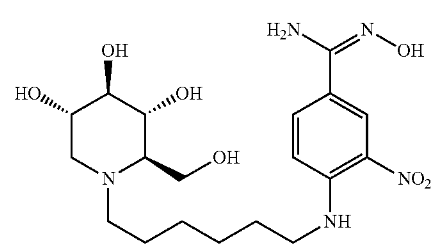 [SMILES: N/C(=N/O)c1ccc(NCCCCCCN2C[C@H](O)[C@@H](O)[C@H](O)[C@H]2CO)c([N+](=O)[O-])c1] |

TABLE 1-continued
Representative compounds
| Compound Code | Compound Structure |
|---|---|
| 0077 | 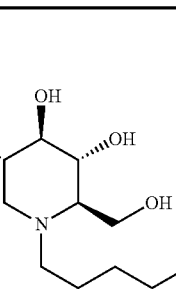 |
| 0079 | 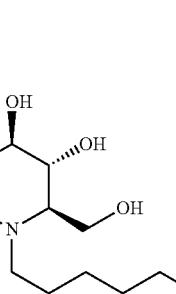 |
| 0080 | 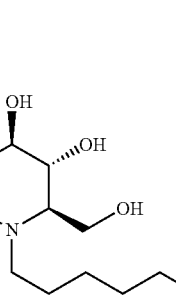 |
| 0081 | 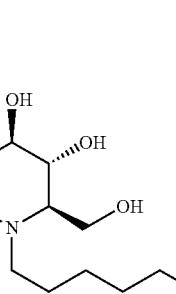 |
| 0082 | 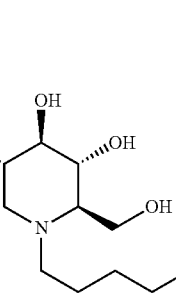 |
| 0083 | 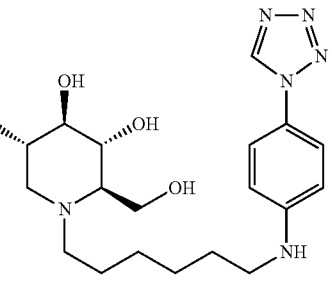 |
| 0084 | 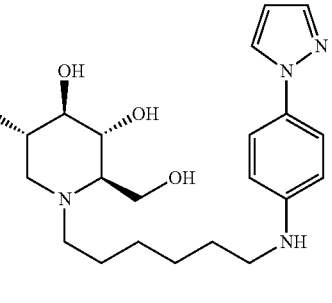 |
| 0086 | 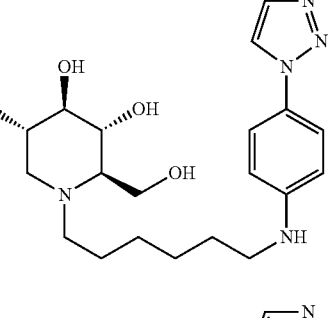 |
| 0087 | 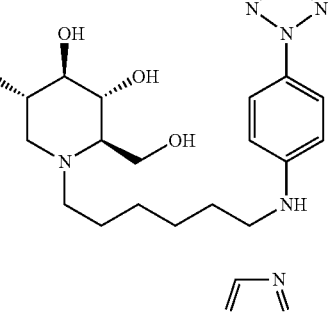 |
| 0088 | 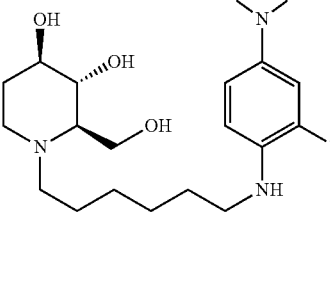 |

TABLE 1-continued

Representative compounds

| Compound Code | Compound Structure |
|---|---|
| 0089 | 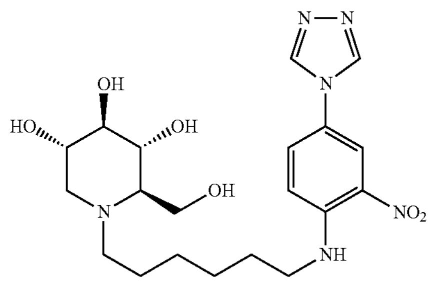 [SMILES: O=[N+]([O-])c1cc(-n2cnnc2)ccc1NCCCCCCN1C[C@H](O)[C@@H](O)[C@H](O)[C@H]1CO] |
| 0090 | 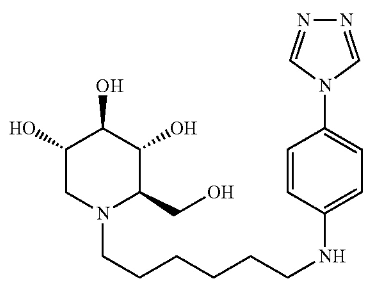 [SMILES: OC[C@@H]1[C@@H](O)[C@H](O)[C@@H](O)CN1CCCCCCNc1ccc(-n2cnnc2)cc1] |
| 0098 | 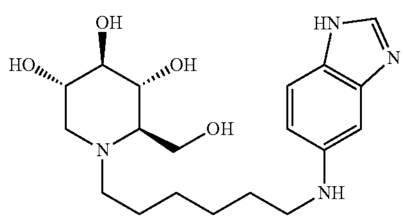 [SMILES: OC[C@@H]1[C@@H](O)[C@H](O)[C@@H](O)CN1CCCCCCNc1ccc2[nH]cnc2c1] |
| 0099 | 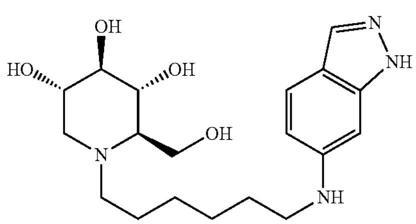 [SMILES: OC[C@@H]1[C@@H](O)[C@H](O)[C@@H](O)CN1CCCCCCNc1ccc2cn[nH]c2c1] |
| 0100 | 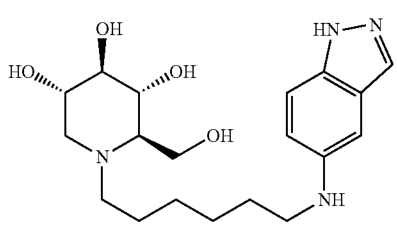 [SMILES: OC[C@@H]1[C@@H](O)[C@H](O)[C@@H](O)CN1CCCCCCNc1ccc2[nH]ncc2c1] |
| 0101 | 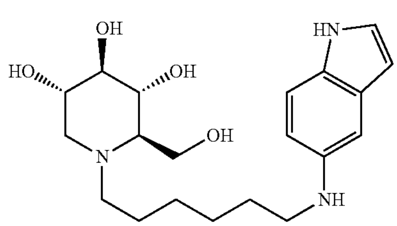 [SMILES: OC[C@@H]1[C@@H](O)[C@H](O)[C@@H](O)CN1CCCCCCNc1ccc2[nH]ccc2c1] |
| 0102 | |
| 0103 | |
| 0104 | |
| 0105 | |
| 0106 | |
| 0107 | |

TABLE 1-continued

Representative compounds

| Compound Code | Compound Structure |
|---|---|
| 0108 | (chemical structure) |
| 0109 | (chemical structure) |
| 0110 | (chemical structure) |
| 0122 | (chemical structure) |
| 0123 | (chemical structure) |
| 0124 | (chemical structure) |
| 0125 | (chemical structure) |
| 0126 | (chemical structure) |
| 0127 | (chemical structure) |
| 0128 | (chemical structure) |

TABLE 1-continued

Representative compounds

| Compound Code | Compound Structure |
|---|---|
| 0129 | 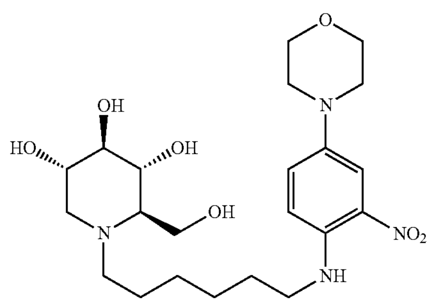 [SMILES: O=[N+]([O-])c1cc(N2CCOCC2)ccc1NCCCCCCN1C[C@H](O)[C@@H](O)[C@H](O)[C@H]1CO] |
| 0130 | 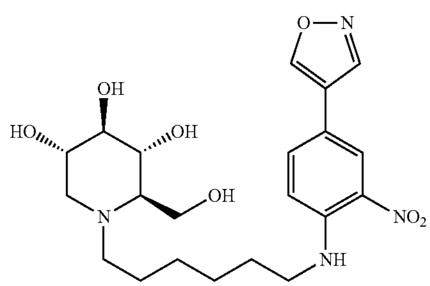 [SMILES: O=[N+]([O-])c1cc(-c2cnoc2)ccc1NCCCCCCN1C[C@H](O)[C@@H](O)[C@H](O)[C@H]1CO] |
| 0131 | 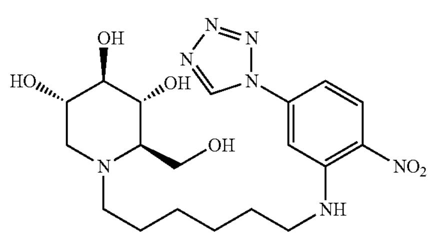 [SMILES: O=[N+]([O-])c1ccc(-n2cnnn2)cc1NCCCCCCN1C[C@H](O)[C@@H](O)[C@H](O)[C@H]1CO] |
| 0132 | 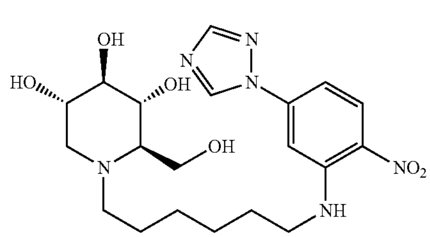 [SMILES: O=[N+]([O-])c1ccc(-n2cncn2)cc1NCCCCCCN1C[C@H](O)[C@@H](O)[C@H](O)[C@H]1CO] |
| 0133 | 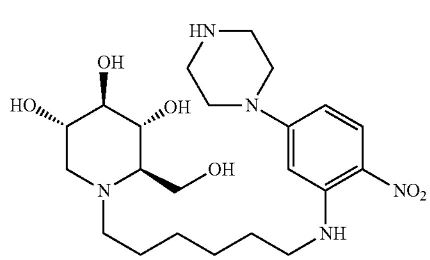 [SMILES: O=[N+]([O-])c1ccc(N2CCNCC2)cc1NCCCCCCN1C[C@H](O)[C@@H](O)[C@H](O)[C@H]1CO] |
| 0134 | |
| 0135 | |
| 0136 | |
| 0139 | |
| 0142 | |

TABLE 1-continued
Representative compounds
| Compound Code | Compound Structure |
|---|---|
| 0143 | 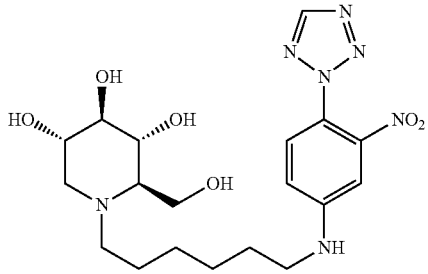 [SMILES: O=[N+]([O-])c1cc(NCCCCCCN2C[C@H](O)[C@@H](O)[C@H](O)[C@H]2CO)ccc1-n1ncnn1] |
| 0153 | 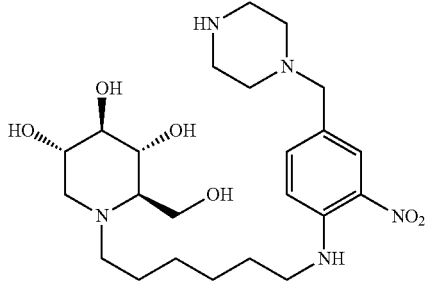 [SMILES: O=[N+]([O-])c1cc(CN2CCNCC2)ccc1NCCCCCCN1C[C@H](O)[C@@H](O)[C@H](O)[C@H]1CO] |
| 0154 | 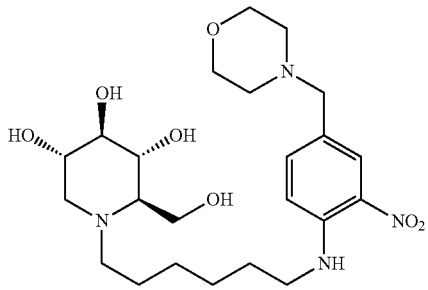 [SMILES: O=[N+]([O-])c1cc(CN2CCOCC2)ccc1NCCCCCCN1C[C@H](O)[C@@H](O)[C@H](O)[C@H]1CO] |
| 0157 | 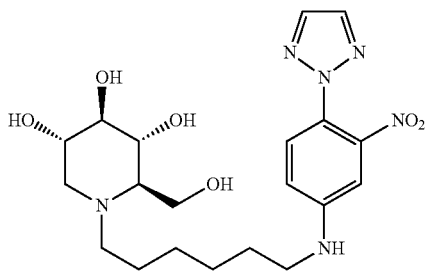 [SMILES: O=[N+]([O-])c1cc(NCCCCCCN2C[C@H](O)[C@@H](O)[C@H](O)[C@H]2CO)ccc1-n1nccn1] |
| 0158 | 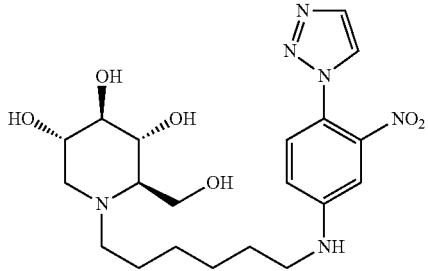 [SMILES: O=[N+]([O-])c1cc(NCCCCCCN2C[C@H](O)[C@@H](O)[C@H](O)[C@H]2CO)ccc1-n1ccnn1] |
| 0160 | 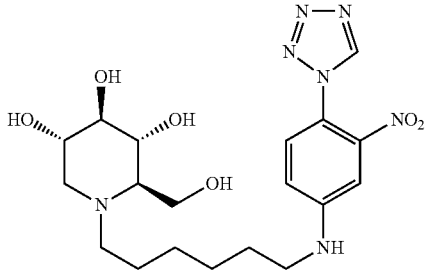 [SMILES: O=[N+]([O-])c1cc(NCCCCCCN2C[C@H](O)[C@@H](O)[C@H](O)[C@H]2CO)ccc1-n1cnnn1] |
| 0162 | 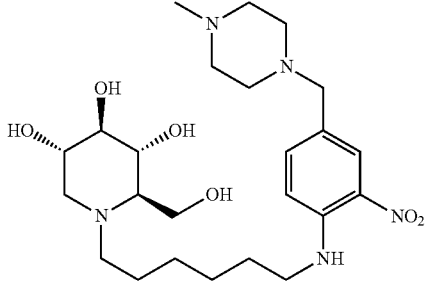 [SMILES: CN1CCN(Cc2ccc(NCCCCCCN3C[C@H](O)[C@@H](O)[C@H](O)[C@H]3CO)c([N+](=O)[O-])c2)CC1] |
| 0163 | 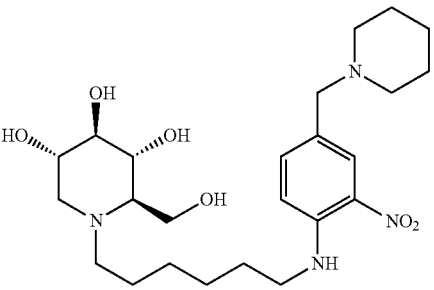 [SMILES: O=[N+]([O-])c1cc(CN2CCCCC2)ccc1NCCCCCCN1C[C@H](O)[C@@H](O)[C@H](O)[C@H]1CO] |
| 0164 | 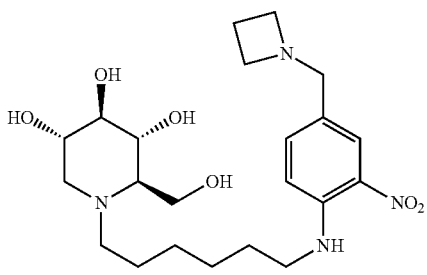 [SMILES: O=[N+]([O-])c1cc(CN2CCC2)ccc1NCCCCCCN1C[C@H](O)[C@@H](O)[C@H](O)[C@H]1CO] |
| 0165 | 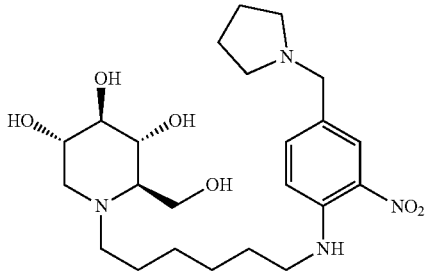 [SMILES: O=[N+]([O-])c1cc(CN2CCCC2)ccc1NCCCCCCN1C[C@H](O)[C@@H](O)[C@H](O)[C@H]1CO] |

TABLE 1-continued

Representative compounds

| Compound Code | Compound Structure |
|---|---|
| 0166 | 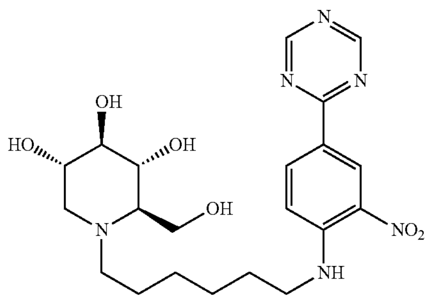 [SMILES: O=[N+]([O-])c1cc(-c2ncncn2)ccc1NCCCCCCN1C[C@H](O)[C@@H](O)[C@H](O)[C@H]1CO] |
| 0167 | 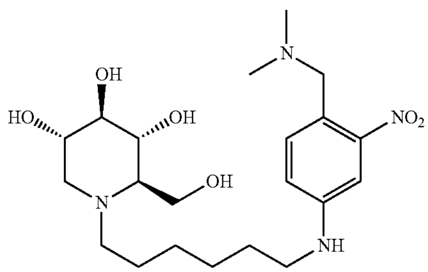 [SMILES: CN(C)Cc1ccc(NCCCCCCN2C[C@H](O)[C@@H](O)[C@H](O)[C@H]2CO)cc1[N+](=O)[O-]] |
| 0168 | 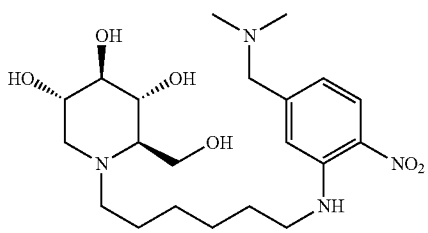 [SMILES: CN(C)Cc1ccc([N+](=O)[O-])c(NCCCCCCN2C[C@H](O)[C@@H](O)[C@H](O)[C@H]2CO)c1] |
| 0177 | 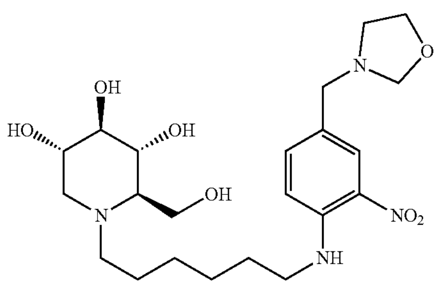 [SMILES: O=[N+]([O-])c1cc(CN2CCOC2)ccc1NCCCCCCN1C[C@H](O)[C@@H](O)[C@H](O)[C@H]1CO] |
| 0178 | 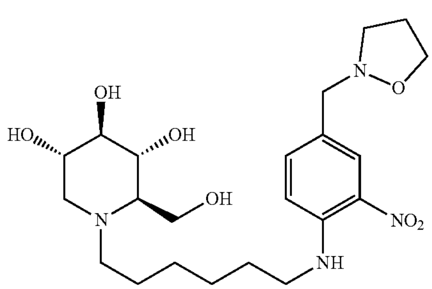 [SMILES: O=[N+]([O-])c1cc(CN2CCCO2)ccc1NCCCCCCN1C[C@H](O)[C@@H](O)[C@H](O)[C@H]1CO] |
| 0179 | |
| 0180 | |
| 0181 | |
| 0182 | |
| 0183 | |

TABLE 1-continued

Representative compounds

| Compound Code | Compound Structure |
|---|---|
| 0184 | (structure) |
| 0185 | (structure) |
| 0188 | (structure) |
| 0198 | (structure) |
| 0241 | (structure) |
| 0242 | (structure) |
| 0243 | (structure) |
| 0244 | (structure) |
| 0245 | (structure) |
| 0246 | (structure) |

In some embodiments, the compound of formula IA may be a part of a pharmaceutical composition, such as an oral pharmaceutical composition, which may also include one or more pharmaceutically acceptable excipients.

The deoxynojirimycin derivatives may be synthesized as illustrated in examples below. Methods of synthesizing deoxynojirimycin derivatives are also disclosed, for example, in U.S. Pat. Nos. 5,622,972, 5,200,523, 5,043,273, 4,994,572, 4,246,345, 4,266,025, 4,405,714, and 4,806,650 and U.S. Patent application publication no. 2007/0275998, which are all incorporated herein by reference.

In some embodiments, the deoxynojirimycin derivative, such as a compound of formula IA, may be in a form of a salt derived from an inorganic or organic acid. Pharmaceutically acceptable salts and methods for preparing salt forms are disclosed, for example, in Berge et al. (J. Pharm. Sci. 66:1-18, 1977). Examples of appropriate salts include but are not limited to the following salts: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate, and undecanoate.

In some embodiments, the deoxynojirimycin derivative may be also used in a form of a prodrug. Prodrugs of DNJ derivatives, such as the 6-phosphorylated DNJ derivatives, are disclosed in U.S. Pat. Nos. 5,043,273 and 5,103,008.

In some embodiments, the deoxynojirimycin derivative, such as a compound of formula IA, may be used as a part of a composition, which further comprises a pharmaceutically acceptable carrier and/or a component useful for delivering the composition to an animal. Numerous pharmaceutically acceptable carriers useful for delivering the compositions to a human and components useful for delivering the composition to other animals such as cattle are known in the art. Addition of such carriers and components to the composition of the invention is well within the level of ordinary skill in the art.

In some embodiments, the pharmaceutical composition may consist essentially of a deoxynojirimycin derivative, such as a compound of formula IA, which may mean that the deoxynojirimycin derivative is the only active ingredient in the composition.

Yet in some embodiments, a deoxynojirimycin derivative, such as a compound of formula IA, may be administered with one or more additional antiviral compounds.

In some embodiments, a deoxynojirimycin derivative, such as a compound of formula IA, may be used in a liposome composition, such as those disclosed in US publications nos. 2008/0138351, 2009/0252785 and 2010/0266678.

In some embodiments, a deoxynojirimycin (DNJ) derivative, such as compound UV-0030 or UV-0060, may be administered to a cell or an animal affected by a virus. The DNJ derivative, such as compound UV-0030 or UV-0060, may inhibit morphogenesis of the virus, or it may treat the individual. The treatment may reduce, abate, or diminish the virus infection in the animal.

In some embodiments, the animal, to whom a DNJ derivative, such as compound UV-0030 or UV-0060, may be administered, may be an animal infected with a Dengue virus which may be a vertebrate, such as a mammal, which may be, for example, a rodent or a primate, such as a human.

In some embodiments, the amount of the DNJ derivative, such as compound UV-0030 or UV-0060, administered to an animal or to an animal cell to the methods of the invention may be an amount effective to inhibit the morphogenesis of Dengue virus from the cell. The term "inhibit" as used herein may refer to the detectable reduction and/or elimination of a biological activity exhibited in the absence of the iminosugar. The term "effective amount" may refer to that amount of the DNJ derivative, such as compound UV-0030 or UV-0060, necessary to achieve the indicated effect. The term "treatment" as used herein may refer to reducing or alleviating symptoms in a subject, preventing symptoms from worsening or progressing, inhibition or elimination of the causative agent, or prevention of the infection or disorder related to the Dengue virus in a subject who is free therefrom.

Yet in some embodiments, the animal to whom a DNJ derivative, such as compound UV-0030 or UV-0060, may be administered, may be an animal that is infected with a virus that belongs to the Togaviridae family, such as Venezuelan equine encephalitis virus. Such animal may be a vertebrate, such as a bird or a mammal, including a primate, a human, a rodent, a livestock animal, such as sheep and goats, or an equine, such as horses, zebras and donkeys, or an invertebrate.

The amount of a DNJ derivative, such as compound UV-0030 or UV-0060, administered to a cell, or an animal can be an amount effective to inhibit the morphogenesis of a virus, that belongs to the Togaviridae family. The term "inhibit" as used herein can refer to the detectable reduction and/or elimination of a biological activity exhibited in the absence of the iminosugar. The term "effective amount" can refer to that amount of the DNJ derivative, such as compound UV-0030 or UV-0060, necessary to achieve the indicated effect. The term "treatment" as used herein can refer to reducing or alleviating symptoms in a subject, preventing symptoms from worsening or progressing, inhibition or elimination of the causative agent, or prevention of the infection or disorder related to the virus that belongs to the Togaviridae family in a subject who is free therefrom.

Thus, for example, treatment of the disease caused by or associated with a virus can include destruction of the infecting agent, inhibition of or interference with its growth or maturation, and abatement or neutralization of its pathological effects. The amount of the DNJ derivative, such as compound UV-0030 or UV-0060, which can be administered to the cell or animal is preferably an amount that does not induce toxic effects which outweigh the advantages which accompany its administration.

Actual dosage levels of active ingredients in the pharmaceutical compositions may vary so as to administer an amount of the active compound(s) that is effective to achieve the desired therapeutic response for a particular patient.

Treatment of the disease caused by or associated with a virus, which may be, for example, a Dengue virus or a virus belonging to the Togaviridae family, such as VEEV virus, may include destruction of the infecting agent, inhibition of or interference with its growth or maturation, and neutralization of its pathological effects.

The selected dose level may depend on the activity of the DNJ derivative, such as compound UV-0030 or UV-0060, the route of administration, the severity of the condition being treated, and the condition and prior medical history of the patient being treated. If desired, the effective daily dose may be divided into multiple doses for purposes of administration, for example, two to four doses per day. It will be understood, however, that the specific dose level for any particular patient may depend on a variety of factors, including the body weight, general health, diet, time and route of administration and combination with other therapeutic agents and the severity of the condition or disease being treated. The adult human dosage may range from about one microgram to about 20 gram, or from about one microgram to about 10 gram; or from about one microgram to about 5 gram or from about one microgram to about 1 gram, or from between about 10 mg and 100 mg, of the DNJ derivative per 10 kilogram body weight or any value or subrange within these ranges. In some embodiments, a total daily dose may be from 0.1 mg/kg body weight to 600 mg/kg body weight or 0.5 mg/kg body weight to 500 mg/kg body weight or from 1 mg/kg body weight to 400 mg/kg body weight or from 1 mg/kg body weight to 350 mg/kg body weight or from 1 mg/kg body weight to 60 mg/kg body weight or from 2 mg/kg body weight to 50 mg/kg body weight or from 3 mg/kg body weight to 30 mg/kg body weight or any value or subrange within these ranges. The daily dose may be administered over one or more administering events per day. For example, in some embodiments, the daily dose may be distributed over two administering events per day, three administering events per day or four administering events. Of course, the amount of the DNJ derivative which should be administered to a cell or animal may depend upon numerous factors well understood by one of skill in the art, such as the molecular weight of the DNJ derivative and the route of administration.

Pharmaceutical compositions that are useful in the methods of the invention may be administered systemically in oral solid formulations, ophthalmic, suppository, aerosol, topical or other similar formulations. For example, it may be in the physical form of a powder, tablet, capsule, lozenge, gel, solution, suspension, syrup, or the like. In addition to the DNJ derivative, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer the DNJ derivative. Such pharmaceutical compositions may be administered by a number of routes. The term "parenteral" used herein includes subcutaneous, intravenous, intraarterial, intrathecal, and injection and infusion techniques, without limitation. By way of example, the pharmaceutical compositions may be administered orally, topically, parenterally, systemically, or by a pulmonary route.

These compositions may be administered a in a single dose or in multiple doses which are administered at different times. Because the inhibitory effect of the composition upon a virus may persist, the dosing regimen may be adjusted such that virus propagation is retarded while the host cell is minimally effected. By way of example, an animal may be administered a dose of the composition of the invention once per week, whereby virus propagation is retarded for the entire week, while host cell functions are inhibited only for a short period once per week.

In many embodiments, an oral pharmaceutical composition comprising the DNJ derivative and a pharmaceutically acceptable excipient may be preferred.

Embodiments described herein are further illustrated by, though in no way limited to, the following working examples.

WORKING EXAMPLES

Example 1. Synthesis of UV-0060 (Also Called UV-60)

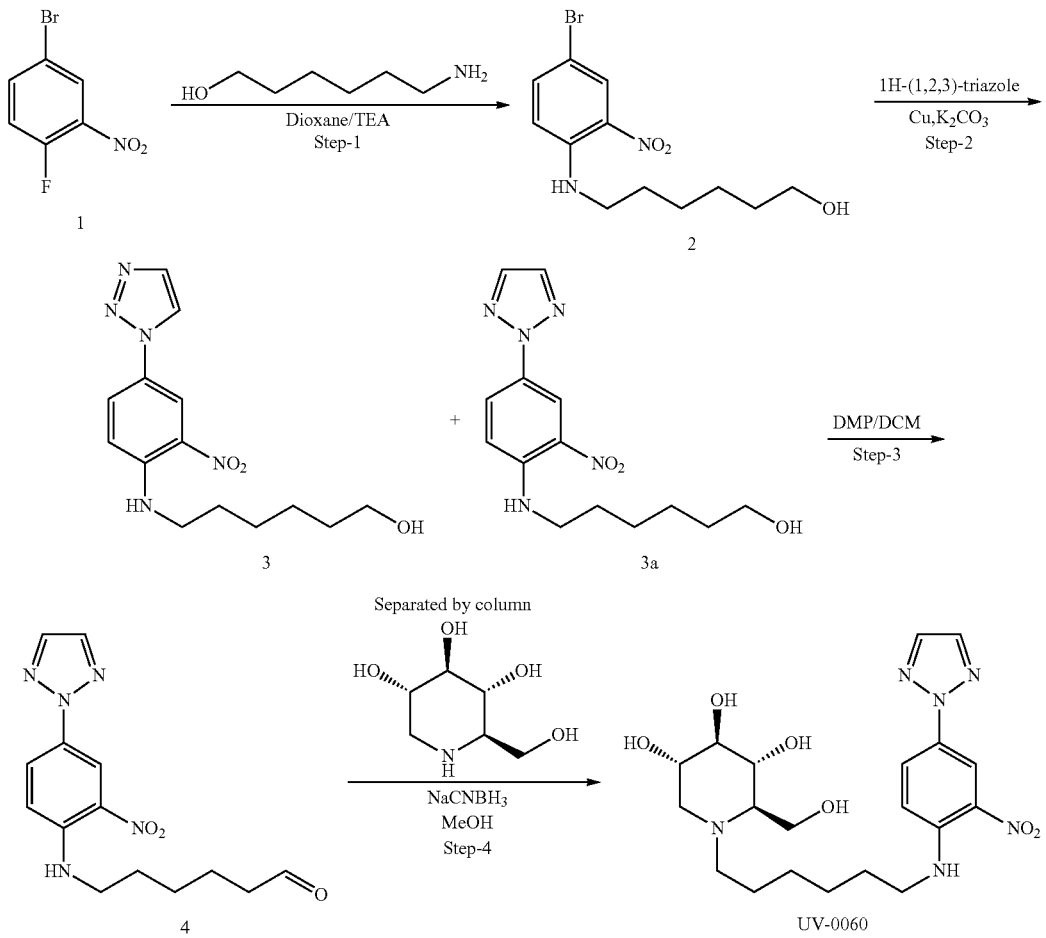

Free DNJ preparation

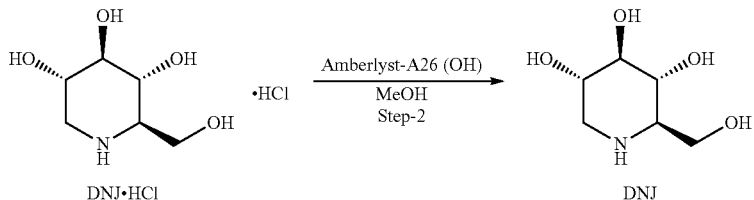

TABLE 2

Synthesis of UV-0060

| S. No. | Reaction/ Conversion | Experimental conditions | Inference |
|---|---|---|---|
| 8 | Preparation of 2 | 1 (35.0 g, 159.09 mmol), 1,4-dioxane (700 mL), TEA (3.0 eq), aminohexanol (1.5 eq), RT-60° C., 16 h. | A new polar spot was observed on TLC after 16 h. The volatiles were removed under reduced pressure to obtain the crude material. The crude material was purified by flash column chromatography (silica gel: 100-200 mesh) by eluting with 35% EtOAc-hexane to afford 42 g (84% yield) of 2 as an orange red solid. Data complies. |
| 7 | Preparation of 3a | 2 (2 × 15 g, 47.1 mmol), 1,2,3-triazole (8.5 eq), Cu (2.1 eq), $K_2CO_3$ (1.7 eq), RT-160° C., 24 h. | Two polar spots with complete consumption of starting material were observed by TLC. The reaction was diluted with EtOAc (500 mL) and the organic layer was concentrated under reduced pressure to obtain the crude material. The crude material was purified by flash column chromatography (silica gel: 100-200 mesh) by eluting with 30% EtOAc/hexane to afford 8.0 g (28% yield) of 3a as red colour thick syrup. $^1$HNMR showed all the desired peaks along with small amount of (1H)-1,2,3-triazole. |
| 14 | Preparation of 4 | 3a (8.0 g, 26.22 mmol), DCM (160 mL), DMP (1.5), 0 C.-RT, 16 h. | After 16 h, a non-polar spot with complete consumption of starting material was observed by TLC. The reaction mass was diluted with water (100 mL), extracted with DCM (250 mL). Separated DCM layer and washed with sat-$NaHCO_3$ (200 mL). The organic layer was concentrated under reduced pressure to afford crude material. The crude material was purified flash column chromatography (silica gel: 100-200 mesh) by eluting with 20% EtOAc-hexane to afford to afford 3.8 g (48% yield) of 4 as orange red solid. Data complies. |
| 15 | Preparation of UV-0060 | 4 (3.8 g, 12.5 mmol), MeOH (60 ml), DNJ (0.8 eq), AcOH (Cat.), $NaCNBH_3$ (1.5 eq), RT, 16 h. | After 16 h, a new polar spot was observed on TLC. The volatiles were removed under reduced pressure to obtain crude material. The crude material was purified by silica gel (100-200) flash column chromatography by eluting with 10% MeOH-DCM to afford 1.5 g (27% yield) of UV-0060 as an orange red solid. $[M + H]^+$ 451.5, Purity by UPLC |

Example 2. Synthesis of UV-0030 (Also Called UV-30)

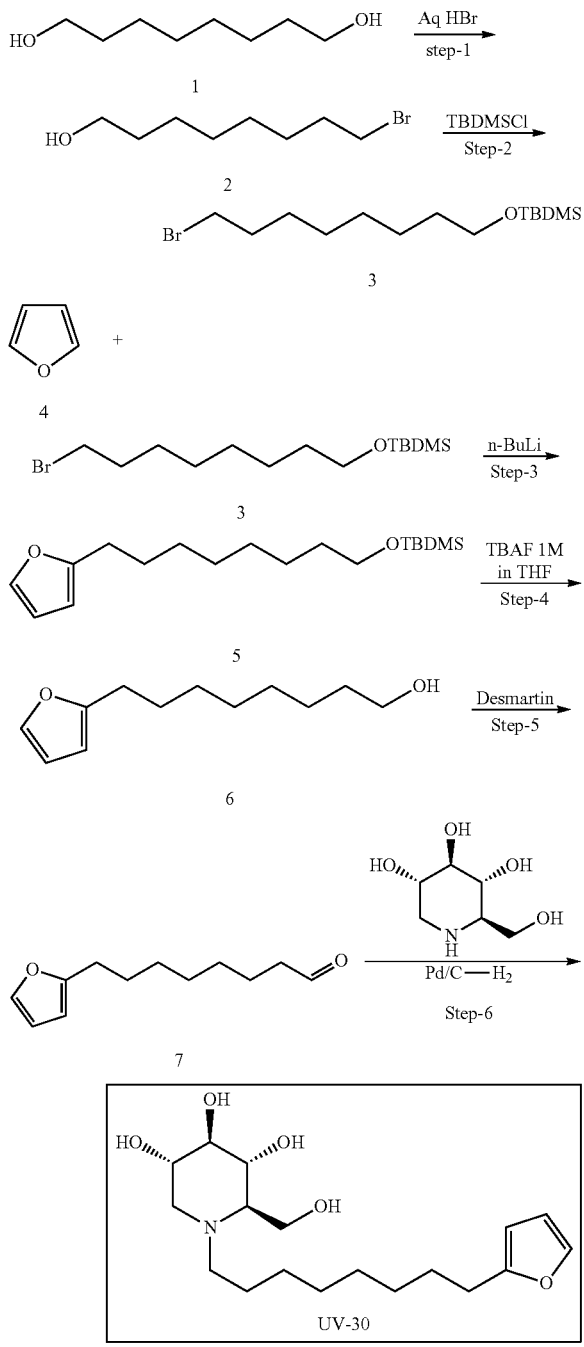

Preparation of 8-bromo octan-1-ol (Compound-2) (SUT-MA1102-086)

Step-1:

To the solution of compound-1 (100 g, 0.76 mol) in toluene (1200 ml), aqueous 47% HBr (600 ml) was added at 0° C. for 20 min and the reaction mixture was heated to 80° C. for 6 h. After consumption of the starting material (by TLC), the reaction mass was quenched with ice cold water (500 ml) then the compound was extracted into EtOAc (2×1000 ml) and combined organic layer was dried over anhydrous $Na_2SO_4$ filtered and concentrated under reduced pressure. The obtained residue was purified by silica gel column chromatography, eluting with 10-15% EtOAc/Hexane to afford 2 (110 g, 68.7%) as yellow liquid.

TLC: 20% EtOAc/Hexane (Rf: 0.5)

1H NMR (500 MHz, CDCl3, δ in ppm): δ 3.62 (m, 2H), 3.40 (m, 2H), 1.85-1.80 (m, 2H). 1.60-1.57 (m, 2H), 1.50-1.25 (m, 8H).

Preparation of (8-bromooctyloxy)(tert-butyl)dimethyl silane)(Compound-3)(SUT-MA1202-063)

Step-2:

To a stirred solution of Compound-2 (25.0 g, 0.111 mol) in dichloromethane (DCM, 375 ml) was added TEA (23.3 ml, 0.166 mol), DMAP (677 mg, 0.005 mol) and cooled to 0° C. then added tert-Butyldimethylchlorosilane, TBDMSCl (21.9 g, 0.144 mol) slowly over a period of 20 min and resulting reaction mixture was stirred at RT for 12 hrs. After complete consumption of the starting material (by TLC), the reaction mass was quenched with saturated NH4Cl solution (200 ml). The compound was extracted with DCM (2×100 ml) and combined organic layer was dried over anhydrous Na2SO4, filtered and concentrated under reduced pressure. The obtained residue was purified by silica gel column chromatography eluting with 3-5% EtOAc/Hexane to afford 3 (25 g, 66.4%) as thick syrup.

TLC: 30% EtOAc/Hexane (Rf: 0.7)

1H NMR (500 MHz, CDCl3, δ in ppm): δ 3.6 (m, 2H), 3.40 (m, 2H), 1.85-1.80 (m, 2H), 1.58-1.40 (m, 4H), 1.35 (m, 6H), 0.95 (s, 9H), 0.02 (s, 6H).

Preparation of tert-butyl(8-(furan-2-yl)octyloxy) dimethylsilane(Compound 5)(SUT-MA1102-093)

Step-3:

To a stirred solution of Furan (60.0 g, 0.88 mol) in THF (1100 ml) was added 2,2-bipyridine (615 mg) and cooled to 0° C. then added n-BuLi (385 ml, 0.61 mol, 1.6M) slowly over a period of 30 min and stirred for 1 hr. Reaction mass was cooled to 0° C. and compound-3 (60 g, 0.17 mol, in 100 ml of THF) was added slowly for 30 min and reaction mixture was gradually warmed to RT and stirred for 12 h. Progress of the reaction was monitored by TLC after complete consumption of starting material reaction mass was quenched with saturated NH4Cl solution (300 ml) and the compound was extracted with ethyl acetate (2×500 ml) and dried over Na2SO4, filtered and concentrated under reduced pressure to afford 5 (60 g, Crude), The obtained crude compound was used for next stage directly without any further purification.

TLC: 30% EtOAc/DCM (Rf: 0.7)

Preparation of 8-(furan-2-yl)octan-1-ol (Compound-6)

Step-4:

To a stirred solution of 5 (100.0 g, Crude) in THF (1000 ml) was added TBAF (600 ml, 1M in THF) at 0° C. slowly for 1 h and reaction mixture was warmed to RT slowly and stirred for 12 h. After complete consumption of starting material (by TLC) reaction mass was quenched with saturated NH4Cl solution (300 ml) and compound was extracted with EtOAc (2×500 ml). Combined organic layer was dried over anhydrous Na2SO4, filtered and concentrated under reduced pressure. The obtained residue was purified by silica gel column chromatography eluting with 15% EtOAc/Hexane to afford 6 (45 g, 74.8%) as thick syrup.

TLC: 30% EtOAc/Hexane (Rf: 0.40)

1H NMR (400 MHz, CDCl3 δ in ppm): δ 7.3 (d, 1H), 6.3 (s, 1H), 6.0 (s, 1H), 3.65 (m, 2H), 2.63 (m, 2H), 1.72-1.50 (m, 4H), 1.4-1.25 (m, 6H).

Preparation of 8-(furan-2-yl)octanal (Compound-7) (SUT-MA1202-073)

Step-5:

To a stirred solution of compound 6 (10.0 g, 0.051 mol) in DCM (200 ml) was added DMP (26.0 g, 0.061 mol) at 0° C. slowly and warmed to RT for 1 h. After complete consumption of the starting material (by TLC), the reaction mass was quenched with saturated NaHCO3 solution and the compound was extracted with DCM (2×100 ml). Combined organic layer was dried over anhydrous Na2SO4 filtered and concentrated under reduced pressure. The obtained residue was purified by silica gel column chromatography eluting with 10% EtOAc/Hexane to afford compound-7 (5.7 g, 56.4%) as thick syrup.

TLC: 20% EtOAc/Hexane (Rf: 0.6)

1H NMR (500 MHz, CDCl3 δ in ppm): δ 9.8 (s, 1H), 7.30 (d, 1H), 6.23 (s, 1H), 5.95 (s, 1H), 2.60 (m, 2H), 2.40 (m, 2H), 1.70-1.60 (m, 4H), 1.40-1.30 (m, 6H).

Preparation of (2R,3R,4R,5S)-1-(8-(furan-2-yl)octyl)-2-(hydroxymethyl)piperidine-3,4,5-triol (UV-30 or UV-0030) (SUT-MA1202-074)

Step-6:

To a stirred solution of 7 (5.7 g, 0.029 mol) in MeOH (150 ml) was added DNJ (3.83 g, 0.023 mol), AcOH (Catalytic) at RT and stirred for 10 min and then added NaCNBH3 (2.8 g, 0.044 mol) the resulting reaction mixture was stirred for 16 h. After complete consumption of the starting material (by TLC), all volatiles were removed under reduced pressure the obtained residue was purified by silica gel column chromatography eluting with 10-30% MeOH/EtOAc to afford UV-30 (2.2 g, 22%) as a low melting solid.

TLC: 20% MeOH/DCM (Rf: 0.4)

1H NMR (400 MHz, CD3OD δ in ppm): δ 7.30 (s, 1H), 6.30 (s, 1H), 6.0 (s, 1H), 3.85 (m, 2H), 3.5 (m, 1H), 3.40-3.25 (m, 1H), 3.20-3.12 (t, 1H), 3.0 (m, 1H), 2.90-2.75 (m, 1H), 2.70-2.52 (m, 3H), 2.25-2.10 (m, 2H), 1.70-1.40 (m, 4H), 1.40-1.25 (m, 8H).

Purity by HPLC-ELSD: 99.72%

Mass (m/z): 342 (M++H)

UV-0030 has been synthesized with acceptable purity for R&D studies (>90%) as determined by HPLC-UV.

Example 3. Synthesis of UV-0031

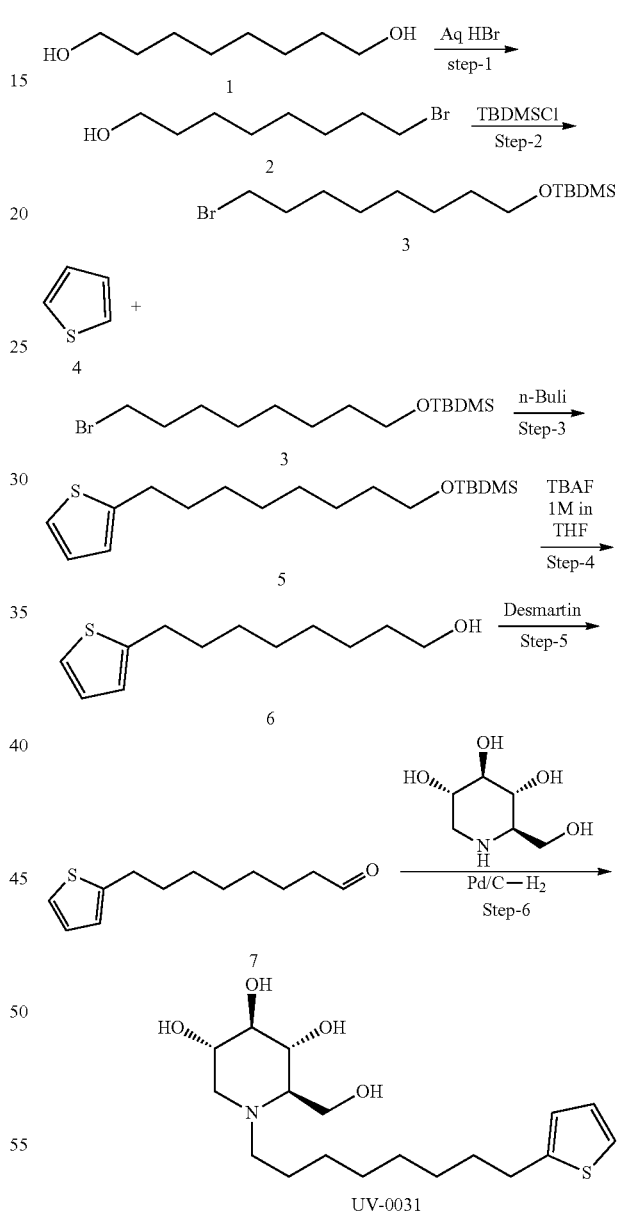

Compound 5:

To a stirred solution of Thiophene (40.0 g, 0.476 mol) in dry THF (800 ml) and 2, 2-bipyridine (800 mg) was added n-BuLi (179 ml, 0.285 mol) slowly at 0° C. over a period of 40 min and stirred for 1 hr at same temperature then added 8-bromooctyloxy)(tert-butyl)dimethyl silane prepared as shown in scheme for UV-0030 (32.3 g, 0.095 mol) in THF (50 ml) slowly and resulting reaction mixture was stirred for 16 hr at room temperature (RT). After complete consumption of the starting material (by TLC), the reaction mass was quenched with saturated NH$_4$Cl solution (200 ml) and compound was extracted with EtOAc (2×250 ml). Combined organic layer was dried over anhydrous Na$_2$SO$_4$, filtered and concentrated under reduced pressure to afford compound 5 (33.0 g) as thick syrup. This scheme was repeated on similar scale to provide additional material. Crude compound was used for next stage without further purification.

Compound 6:

To a stirred solution of 5 (35.0 g, crude) in THF (700 ml) was added TBAF (300 ml, 1.0M in THF) slowly at 0° C. for 20 min and slowly warmed to RT and stirred for 12 hrs. After complete consumption of the starting material (by TLC), the reaction mass was quenched with ice cold water (250 ml) and the compound was extracted with EtOAc (2×150 ml). Combined organic layer was dried over anhydrous Na$_2$SO$_4$, filtered and concentrated under reduced pressure. The obtained crude compound was purified by column chromatography eluting with 15% EtOAc/Hexane to afford compound 6 (19 g, 83.7) as thick syrup.

Compound 7:

To a stirred solution of compound 6 (12.0 g, 0.056 mol) in CHCl$_3$ (240 ml) was added PCC (30.5 g, 0.141 mol) at 10° C. slowly and warmed to RT for 4 h. After complete consumption of the starting material (by TLC), the reaction mass was filtered and concentrated under reduced pressure. The obtained residue was purified by silica gel column chromatography eluting with 10% EtOAc/Hexane to afford 7 (8.3 g, 69.7%) as thick syrup.

Preparation of UV-0031:

To a stirred solution of 7 (8.3 g, 0.039 mol) in MeOH (250 ml) was added DNJ (5.2 g, 0.031 mol), AcOH (Catalytic) at RT and stirred for 10 min and then added NaCNBH$_3$ (3.7 g, 0.059 mol) the resulting reaction mixture was stirred at RT for 16 h. After complete consumption of the starting material (by TLC), volatiles were removed under reduced pressure. The obtained residue was purified by silica gel column chromatography eluting with 10-30% MeOH/EtOAc to afford UV-0031 (2.2 g, 15.6%) as a low melting solid. TLC: 20% MeOH/DCM (R$_f$: 0.3); $^1$H NMR (400 MHz, CD3OD δ in ppm): δ 7.15 (d, 1H), 6.90 (d, 1H), 6.75 (m, 1H), 3.85 (m, 2H), 3.5 (m, 1H), 3.40-3.30 (m, 1H), 3.20-3.12 (t, 1H), 3.0 (m, 1H), 2.90-2.75 (m, 2H), 2.60 (m, 1H), 2.25-2.10 (m, 2H), 1.72-1.45 (m, 4H), 1.40-1.20 (m, 8H); purity by HPLC-ELSD: 98.22%, [M+H]$^+$ 358.4. Purity by HPLC-ELSD: 98.22% (column: Acquity UPLC HSS-T3 {100×2.1 mm, 1.8μ}; RT 4.07 min; ACN: 0.025% TFA); 0.5 mL/min).

Example 4. Synthesis of UV-0047

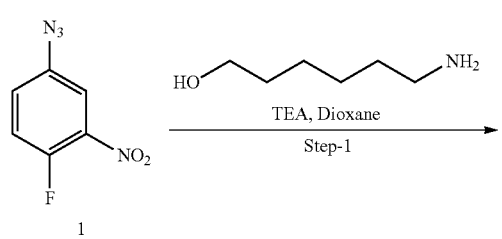

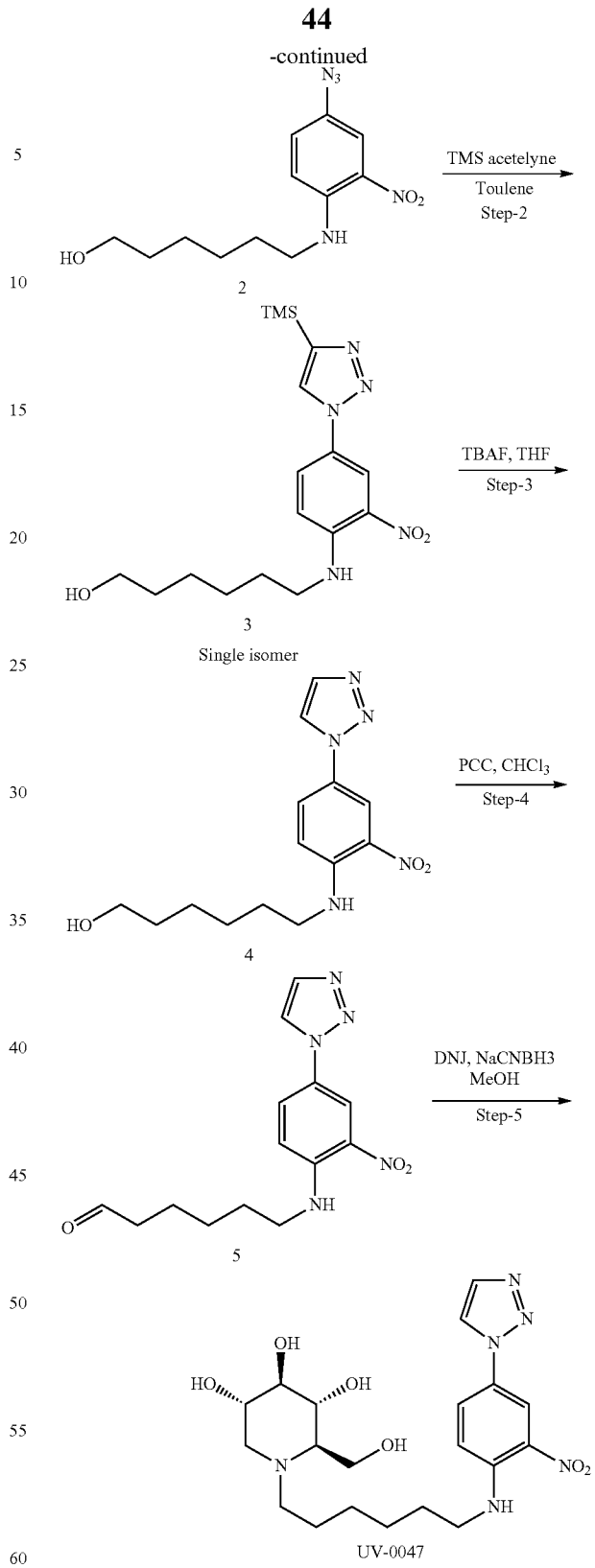

Step-1: To a stirred solution of 1 (10 g, 54.94 mmol) in 1,4 Dioxane (200 ml), was added 6-Aminohexanol (2.0 eq) at RT and stirred for 20 min. To this, TEA (3.0 eq) was added at RT and resulting reaction mixture was warmed to 55° C. for 16 h. After complete conversion of starting material (monitored by TLC), the volatiles were removed under reduced pressure to obtain the crude material. The crude material was purified by silica gel flash column chromatography to afford 16 g of compound-2 as yellow thick syrup.

Step-2: To a stirred solution of 2 (500 mg, 1.78 mmol) in Toluene (5 ml) was added TMS acetylene (5 ml) at RT in a sealed tube and resulting reaction mixture was warmed to 80° C. for 48 h. After complete consumption of starting material (by TLC), the volatiles were concentrated under reduced pressure to afford crude material which was purified by column chromatography by eluting with 10-15% EtOAC/DCM to afford 603 mg (Yield: 90%) of compound-3 as yellow colored solid. Similarly 2.0 g of compound-2 gave 2.4 g (Yield: 90%) of compound-3 as yellow colored solid. Same reaction was completed on 10.0 g of compound-2 to afford 11.0 g of 3 as yellow color solid.

Step-3: To a stirred solution of 3 (600 mg, 1.59 mmol) in THF (10 ml) was added 1 m TBAF (3.0 eq) at 0° C. slowly and resulting reaction mixture was warmed to RT and stirred for 4 h. After complete conversion of starting material (monitored by TLC), reaction mass was quenched with ice-cold water and extracted with EtOAc (2×30 mL). The combined organic extracts were washed with brine, dried over anhydrous Na2SO4 and concentrated under reduced pressure to afford 480 mg (crude) of compound-4 as yellow colored solid. Similarly 2.4 g of compound-3 gave 1.9 g (crude) of compound-4 as yellow colored solid. Same reaction was completed on 11.0 g compound-3 to afford 9.0 g of 4 as yellow color solid.

Step-4: To a stirred solution of 4 (250 mg, 0.81 mmol) in CHCl3 (10 ml), was added PCC (2.5 eq) at 10° C. and slowly warmed to RT and stirred for 4 h. After complete consumption of starting material (monitored by TLC), reaction mass was filtered through a celite bed and washed with DCM (20 ml) filtrate was concentrated under reduced pressure to obtained crude. The crude material was purified by silica gel column chromatography to afford 100 mg of 5 as yellow colored solid. Similarly 5.0 g of compound-4 gave 2.0 g of compound-5 as yellow colored solid.

Step-5: To a stirred solution of compound 5 (100 mg, 0.33 mmol) in MeOH (5 ml) was added DNJ (0.8 eq), AcOH (cat.) at RT and stirred for 10 min. To this, NaCNBH3 (1.5 eq) was added and stirred at RT for 16 h. After complete consumption of starting material (monitored by TLC), the volatiles were concentrated under reduced pressure to obtain the crude. The crude material was purified by silica gel column chromatography by eluting with 20% MeOH-EtOAc to afford 60 mg of UV-47 as yellow colored thick syrup. Similarly 2.0 g of compound-5 gave 1.0 g of UV-47 as yellow colored low melting solid. Purity by UPLC 96.49%; (column: Acquity UPLC BEH C-18 {50×2.1 mm, 1.7µ}; RT 1.49 min; ACN: 0.025% TFA (Aq); 0.5 mL/min; [M+H]+ 451.6 by LCMS.

Example 5. Synthesis of UV-0069

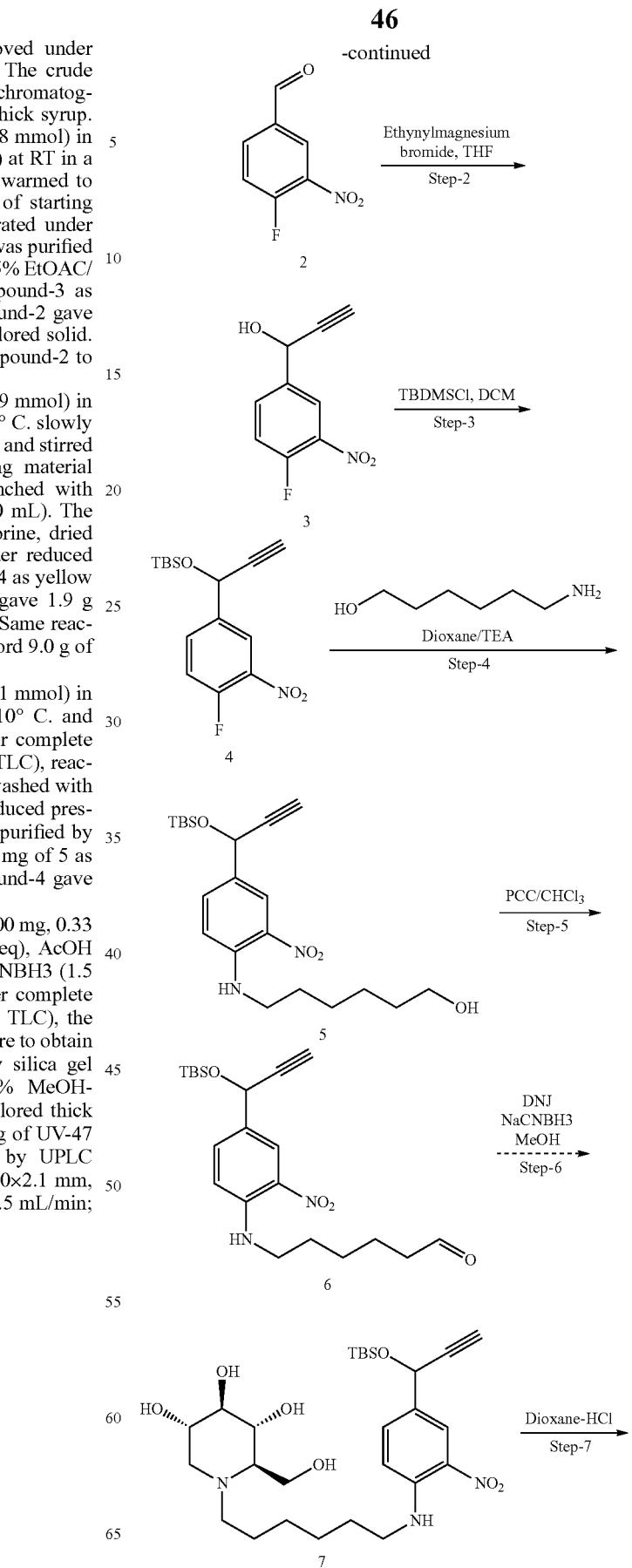
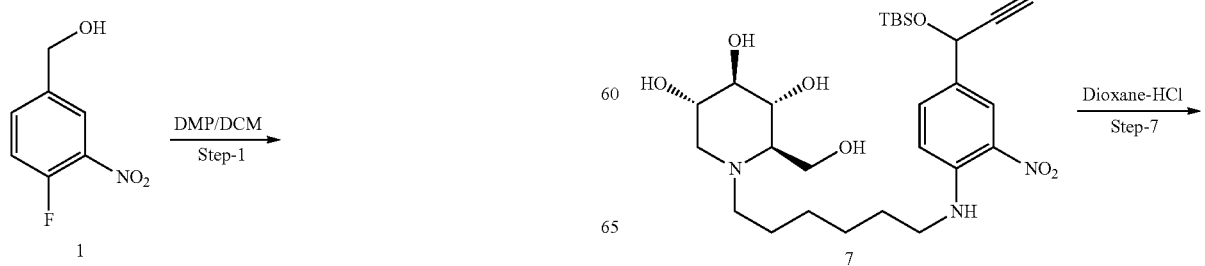

47

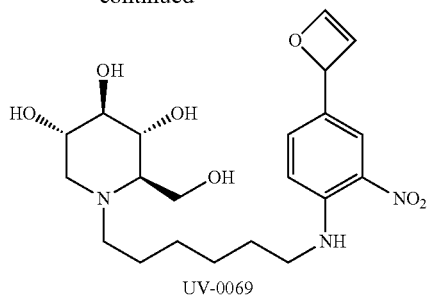

UV-0069

Preparation of 2:

1 (2.0 g, 11.00 mmol), DCM (40 ml), DMP (1.5 eq), 0° C. for 5 min; gradually warmed to RT for 10 min and stirred at RT for 3 h. After purification afforded 1.5 g of 2.

Preparation of 3:

2 (1.5 g, 8.80 mmol), dry THF (30 ml), 0.5M Ethynyl-magnesiumbromide in THF (2.0 eq), −30° C. for 1 h; gradually warmed to RT for 30 min and stirred at RT for 4 h. After purification afforded 1.0 g of 3.

Preparation of 4:

3 (500 mg, 2.56 mmol), DCM (10 ml), TEA (2.0 eq), TBDMSCl (1.2 eq), 0° C. for 5 min; gradually warmed to RT for 10 min and stirred at RT for 20 h. After purification afforded 500 mg of 4.

Preparation of 5:

4 (500 mg, 1.6 mmol), 1,4 dioxane (20 ml), TEA (3.0 eq), 6-aminohexanol (1.5 eq), RT for 5 min; gradually raised to 70° C. for 10 min and stirred at 70° C. for 16 h. After purification afforded 520 mg of 5.

Preparation of 6:

5 (520 mg, 1.28 mmol), CHCl3 (20 ml), PCC (2.5 eq), 10° C. for 10 min; gradually warmed to RT for 10 min and stirred at RT for 3 h. After purification afforded 200 mg of 6.

Preparation of 7:

6 (200 mg, 0.49 mmol), MeOH (10 ml), DNJ (0.8 eq), AcOH (Cat.), RT, 30 min, NaCNBH3 (1.5 eq), RT, 16 h. Purification afforded 100 mg of 7.

Preparation of UV-0069:

7 (100 mg, 0.18 mmol), 1,4 dioxane (5 ml), 4 M HCl in 1,4 dioxane (2 ml), 0° C. for 10 min; gradually warmed to RT for 10 min and stirred at RT for 16 h. By TLC one major polar product was formed. LCMS showed 66% of product formation. Mass based purification [column Ascentis C-18 (250×21.2 mm, 10μ) (60 mg loading; CH3CN: 0.05% TFA; T/B %: 0.1/90, 2/80, 15/70, 25/20, 30/10, 35/10; as mobile phase; flow rate: 15 mL/min)] afforded 20 mg of UV-0069. Purity 98.75% by UPLC (column: Acquity UPLC BEH C-18 {2.1×50 mm, 1.7μ}; RT 1.60 min; ACN: 0.025% TFA (Aq); 0.5 mL/min), [M+H]+ 438.5. The multiplicities and chemical shifts observed in ¹H-NMR are in compliance with expected pattern for the indicated structure.

48

Example 6. Synthesis of UV-0073

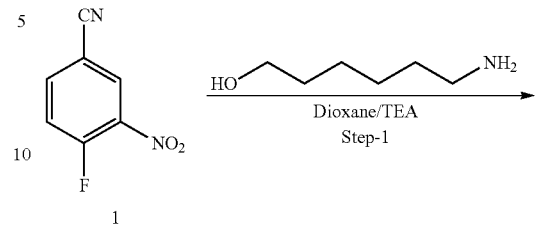

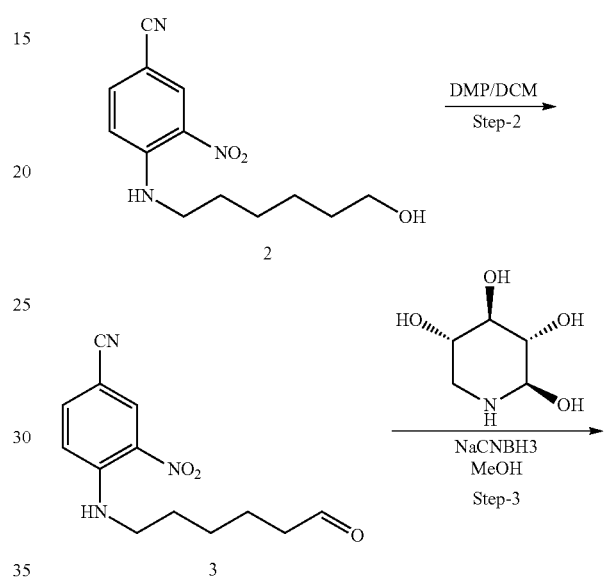

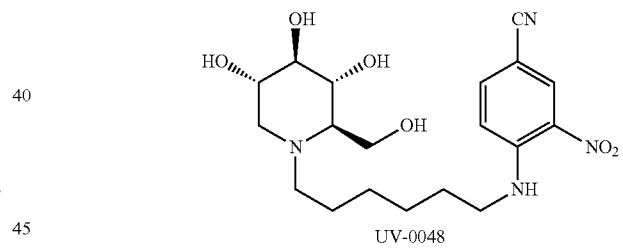

UV-0048

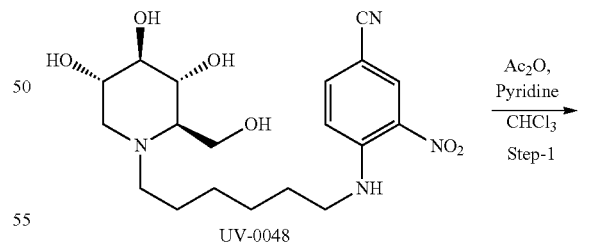

UV-0048

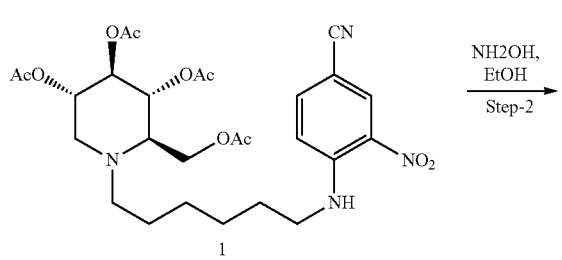

1

-continued

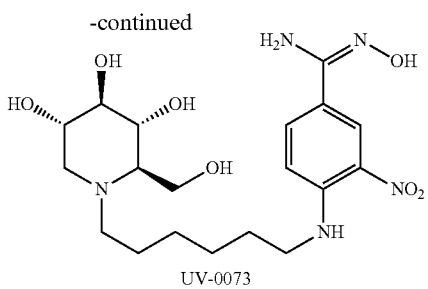

UV-0073

Step-1: To a stirred solution of 1 (1.0 g, 6.0 mmol) in 1, 4 Dioxane (20 ml), was added 6-Aminohexanol (1.5 eq) at RT and stirred for 20 min. To this, TEA (3.0 eq) was added and resulting reaction mixture was warmed to 55° C. for 16 h. After complete conversion of starting material (monitored by TLC), the volatiles were removed under reduced pressure to obtain the crude material. The crude material was purified by silica gel flash column chromatography to afford 1.1 g of compound-2 as yellow solid. 1H NMR data is in agreement with the product. Similarly 4.0 g of compound-1 gave 4.5 g of compound-2 as yellow color solid. Same reaction on 8.0 g compound 1 afforded 10.0 g of 2 as yellow color solid.

Step-2: To a stirred solution of 2 (1.0 g, 3.80 mmol) in DCM (20 ml), was added DMP (1.2 eq) at 0° C. and slowly warmed to RT and stirred for 2 h. After complete consumption of starting material (monitored by TLC). Reaction mass was quenched with Sat. NaHCO3 and extracted with DCM (2×40 mL). The combined organic extracts were washed with brine, dried over anhydrous Na2SO4 filtered and concentrated under reduced pressure to afford the crude. The crude material was purified by silica gel column chromatography to afford 700 mg of 3 as yellow colored thick syrup. Similarly 12.0 g of compound-2 gave 9.0 g of compound-3 as yellow color solid.

Step-3: To a stirred solution of compound 3 (700 mg, 3.06 mmol) in MeOH (20 ml) was added DNJ (0.8 eq), AcOH (cat.) at RT and stirred for 10 min. To this, NaCNBH3 (1.5 eq) was added and stirred at RT. After complete consumption of starting material (monitored by TLC), the volatiles were concentrated under reduced pressure to obtain the crude. The crude material was purified by silica gel column chromatography by eluting with 20% MeOH-EtOAc to afford 350 mg of UV-48 as yellow colored solid. Similarly 9.0 g of compound-3 gave 4.0 g of UV-48 as yellow colored solid. HPLC purity: 94.85%. This solid was triturated with EtOAc (150 ml) to afford 3.5 g of UV-48 as yellow colored solid. 1H NMR data is in agreement with the product. HPLC purity: 95%, M+H+409.6 by LCMS.

Preparation of tetraacetyl-UV-48

UV-48 (300 mg, 0.73 mmol), CHCl3 (5 ml), pyridine (5 ml), Ac2O (10 eq), 0° C. for 10 min; gradually warmed to RT for 10 min and stirred at RT for 72 h. Work up afforded 400 mg of tetraacetyl-UV-48.

Preparation of UV-0073 (Also Called UV-73):

Tetraacetyl-UV-48 (400 mg, 0.69 mmol), EtOH (5 ml), 50% Aq NH2OH (2.0 eq), RT, 5 h, 50% Aq NH2OH (4.0 eq), RT, 16 h. Crude LCMS showed 68% product formation. Preparative HPLC purification [column Ascentis C-18 (250×21.2 mm, 10µ) (100 mg loading per injection; CH3CN: 5 mM NH4OAc; T/B %: 0.1/90, 2/80, 12/50, 20/20, 25/10, 35/10; as mobile phase; flow rate: 15 mL/min)] afforded 100 mg of UV-0073 containing ammonium acetate, hence re-purified by second preparative purification to afford 70 mg of UV-0073, purity 95.54% by UPLC [column: Acquity UPLC HSS-T3 (100×2.1 mm, 1.8µ); RT 2.87 min; ACN: 0.025% TFA (Aq); 0.5 mL/min)], [M+H]+ 442.5 by LCMS.

Example 7. Synthesis of UV-0077

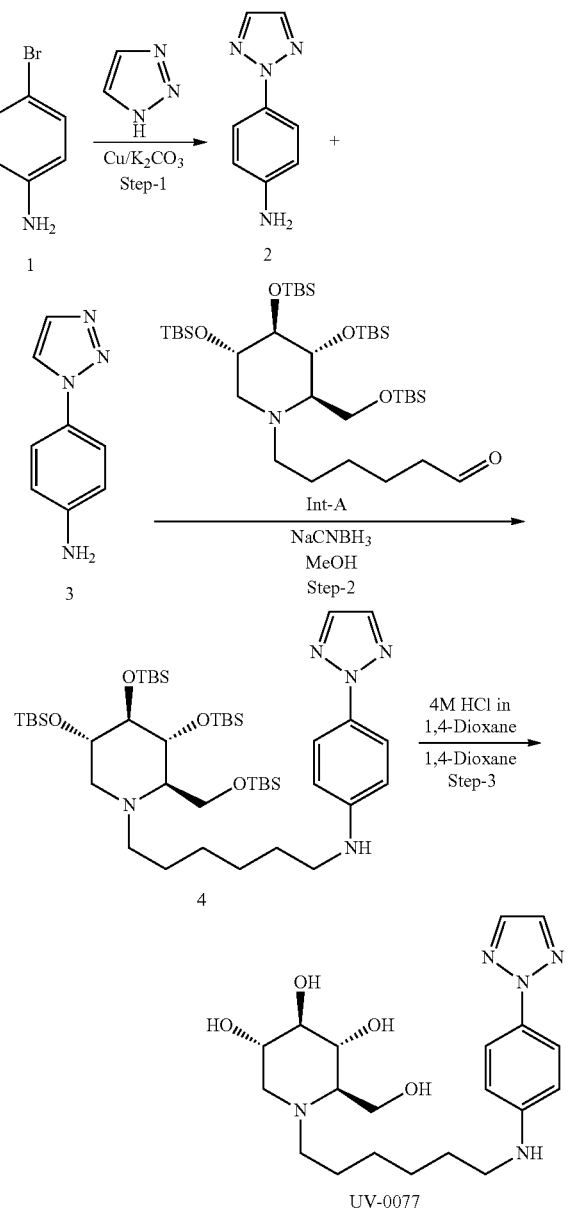

Preparation of 2 and 3:

1 (500 mg, 2.90 mmol), 1,2,3-triazole (3.0 eq), Cu (2.5 eq), K2CO3 (2.0 eq), RT, for 5 min; gradually heated to 160° C. for 20 min and stirred at 160° C. for 16 h. Two polar spots were observed by TLC. The reaction mixture was diluted with water and extracted with EtOAc (2×40 mL). The combined organic layer was washed with water and dried over anhydrous Na2SO4, filtered and concentrated under reduced pressure to afford the crude. The obtained crude material was purified by silica gel column chromatography

[using 100-200 mesh, compound-2 was eluted with 40% EtOAc-hexane and compound-3 was eluted with 60% EtOAc-hexane] to afford 320 mg of 2 and 250 mg of 3.

Preparation of 4:

Int-A (see below, also called Int-1, 700 mg, 0.97 mmol), MeOH (30 ml), 2 (0.8 eq), AcOH (Cat.), NaCNBH3 (1.5 eq), RT, 20 h. Work up and column purification afforded 120 mg of 4.

Preparation of UV-0077 (Also Called UV-77):

4 (120 mg, 0.13 mmol), 1,4-dioxane (2 ml), 4M HCl in 1,4-dioxane (1 mL), 0° C. for 10 min; gradually warmed to RT for 10 min and stirred at RT for 16 h. Prep HPLC purification [column X-select CSH C-18 (250×19 mm, 5µ) (50 mg per injection; CH₃CN: 5 mM NH₄OAc; T/B %: 0.1/90, 2/90, 12/60, 17/50, 22/40, 25/30, 30/20, 35/20, 40/10, 45/10; as mobile phase; flow rate: 15 mL/min)] afforded 6.0 mg of UV-0077, 98.78% purity by UPLC (column: Acquity UPLC BEH C-18 {2.1×50 mm, 1.7µ}; RT 1.34 min; ACN: 0.025% TFA (Aq); 0.5 mL/min), [M+H]⁺ 406.7 by LCMS. 1H-NMR showed ~2% ammonium acetate.

Synthesis of Int-A (Int-1):

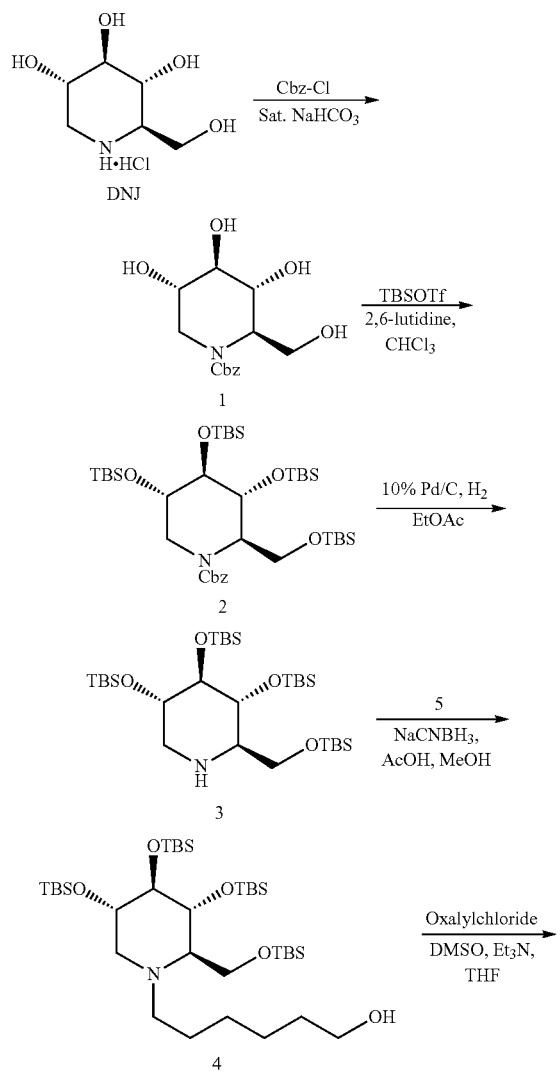

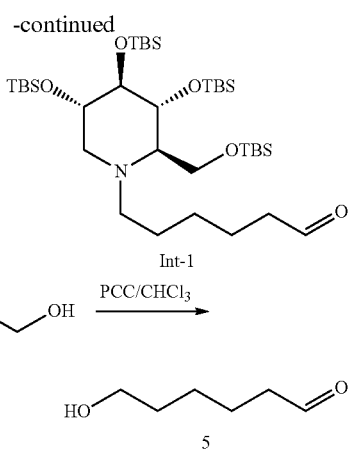

Preparation of 1:

To a stirred solution of (2R,3R,4R,5S)-2-(hydroxymethyl)piperidine-3,4,5-triol hydrochloride DNJ (25 g, 125.62 mmol) in saturated NaHCO₃ solution (300 mL) was added benzyl chloroformate (50% in toluene, 42.8 mL, 125.62 mmol) drop wise at 0° C. The reaction mixture was gradually warmed to RT for 15 min and stirred for 6 h. The reaction was monitored by TLC; after completion of the reaction, reaction mixture was diluted with water (500 mL), washed with CH₂Cl₂ (3×300 mL) and separated. The aqueous layer was extracted with EtOAc (5×300 mL). The combined organic extracts were dried over sodium sulfate, filtered and concentrated in vacuo to afford compound 1 (30 g, 80.8%) as thick syrup. This crude material was taken to the next step without further purification.

Preparation of 2:

To a stirred solution of 1 (30 g, 101.10 mmol) in CHCl₃ (600 mL) were added TBSOTf (139.6 mL, 606.06 mmol) and 2,6-lutidine (117.5 mL, 1011.00 mmol) at 0° C. under argon atmosphere. The reaction mixture was gradually warmed to RT for 15 min and stirred for 16 h. The reaction was monitored by TLC; after completion of the reaction, the reaction mixture was diluted with water (500 mL) and extracted with CH₂Cl₂ (3×300 mL). The combined organic extracts were dried over sodium sulfate, filtered and concentrated in vacuo to obtain the crude. The crude material was purified by silica gel column chromatography [using 100-200 mesh, eluting with 3% EtOAc-hexane] to afford compound 2 (50 g, 66.22%) as colorless thick syrup.

Preparation of 3:

To a stirred solution of 2 (50 g, 10.61 mmol) in ethyl acetate (500 mL) was added 10% Pd/C (10 g, 50% wet) at RT under argon atmosphere. The reaction mixture was kept under hydrogen atmosphere (balloon) and stirred for 24 h. The reaction was monitored by TLC; after completion of the reaction, the reaction mixture was filtered through a pad of celite. The filtrate was concentrated under reduced pressure to obtain the crude which was purified by silica gel column chromatography [using 100-200 mesh, eluting with 3% EtOAc-hexane] to afford compound 3 (41.6 g, 96.1%) as thick syrup.

Preparation of 5:

To a stirred solution of hexane-1,6-diol (6, 50 g, 423.72 mmol) in chloroform (1000 mL) were added PCC (55 g, 254.24 mmol) and celite (50 g) at RT under argon atmosphere and stirred for 3 h. The reaction was monitored by TLC; after completion of the reaction, the reaction mixture was filtered and the filtrate was concentrated under reduced pressure to obtain the crude which was purified by silica gel column chromatography [using 100-200 mesh, eluting with 40% EtOAc-hexane] to afford compound 5 (10 g, 20.18%) as thick syrup.

Preparation of 4:

To a stirred solution of compound 3 (40 g, 64.51 mmol) in methanol (800 mL) were added compound 5 (9.05 g, 77.42 mmol) and acetic acid (cat) at 0° C. under argon atmosphere and stirred for 30 min. The reaction mixture was gradually warmed to RT for 15 min and added sodiumcyanoborohydride (6.09 g, 96.71 mmol) and stirred for 16 h. The reaction was monitored by TLC; after completion of the reaction, the volatiles were removed in vacuo. The residue was diluted with water (200 mL) and extracted with EtOAc (3×200 mL). The combined organic extracts were dried over sodium sulfate, filtered and concentrated in vacuo to obtain the crude which was purified by silica gel column chromatography [using 100-200 mesh, eluting with 10% EtOAc-hexane] to afford compound 4 (35 g, 75.3%) as colourless thick syrup.

Preparation of Int-1:

To a stirred solution of oxalyl chloride (3.57 mL, 40.8 mmol) in THF (200 mL) was added DMSO (3.57 mL, 50.4 mmol) at −78° C. under argon atmosphere and stirred for 15 min. To this was added 4 (14 g, 19.4 mmol) in THF (30 mL) drop wise at −78° C. and stirred for 30 min. Then triethylamine (10.65 mL, 104.2 mmol) was added at −78° C. and gradually warmed to RT for 1 h. The reaction was monitored by TLC; after completion of the reaction, the reaction mixture was quenched with ice cold water (100 mL) and extracted with EtOAc (3×100 mL). The combined organic extracts were dried over sodium sulfate, filtered and concentrated in vacuo to obtain the crude. The crude was purified by silica gel column chromatography [using 100-200 mesh, eluting with 10% EtOAc-hexane] to afford Int-1 (10 g, 71.9%) as colorless syrup.

$^1$H NMR (500 MHz, CDCl$_3$): δ 9.78 (s, 1H), 3.96-3.94 (m, 1H), 3.77-3.61 (m, 3H), 3.52 (dd, J=10.0, 5.5 Hz, 1H), 2.92-2.78 (m, 2H), 2.75-2.64 (m, 3H), 2.43 (t, J=7.2 Hz, 2H), 1.69-1.61 (m, 2H), 1.52-1.43 (m, 2H), 1.38-1.30 (m, 2H), 0.95-0.85 (m, 36H), 0.12-0.02 (m, 24H)

Example 8. Synthesis of UV-0079

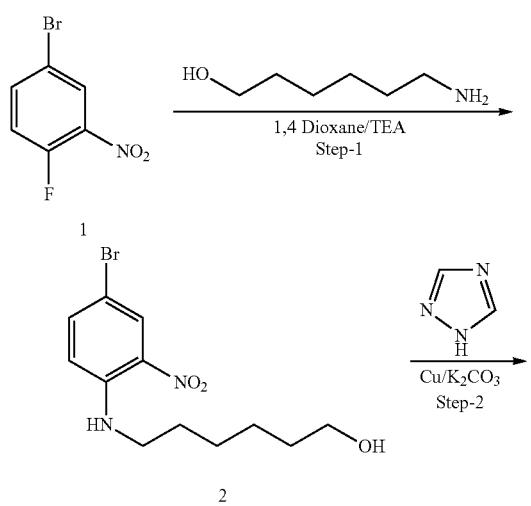

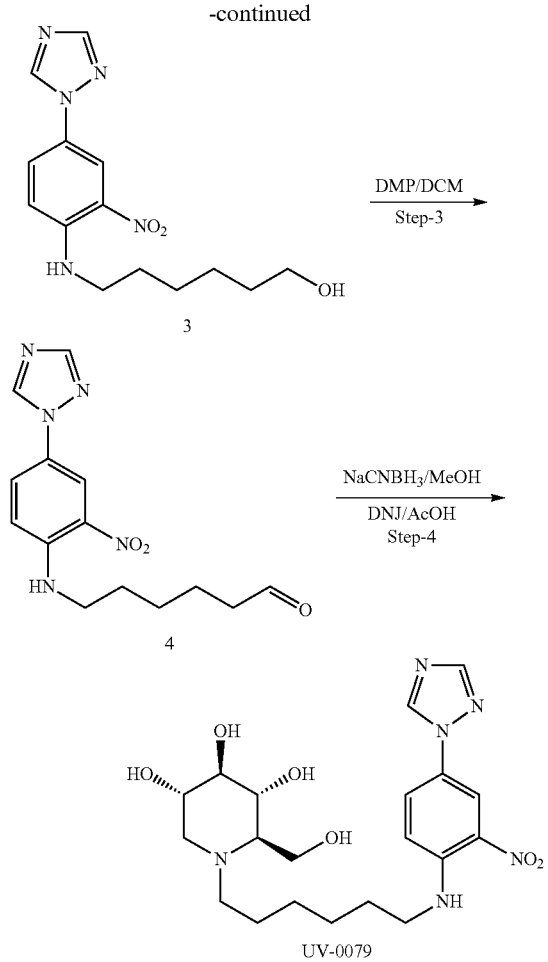

Preparation of 2:

1 (2.0 g, 9.17 mmol), 1,4-dioxane (40 mL), TEA (3.0 eq), aminohexanol (1.2 eq), RT for 5 min; heated to 80° C. for 10 min and stirred for 16 h. Work up and column purification afforded 2.0 g of 2. Repeat preparation with 1 (8.0 g, 36.68 mmol), 1,4-dioxane (160 mL), TEA (3.0 eq), aminohexanol (1.2 eq), RT for 5 min; slowly heated to 80° C. for 10 min and stirred for 16 h. Work up and column purification afforded 7.5 g of 2.

Preparation of 3:

2 (100 mg, 0.31 mmol), 1,2,4-triazole (3.0 eq), Cu (2.5 eq), K2CO3 (2.0 eq), RT, gradually warmed to 160° C. for 20 min and stirred for 16 h. Column purification afforded 20 mg of 3. Repeat reaction with 2 (2.0 g, 6.30 mmol), 1,2,4-triazole (3.0 eq), Cu (2.5 eq), K2CO3 (2.0 eq), RT, gradually heated to 160° C. for 20 min and stirred for 16 h. Column purification afforded 400 mg of 3.

Preparation of 4:

Oxalylchloride (2.1 eq), THF (5.0 ml), DMSO (2.6 eq), −78° C., 30 min, 3 (100 mg, 0.32 mmol), −78° C., 30 min, TEA (5.4 eq), −78° C., 30 min, gradually warmed to RT for 30 min and stirred for 2 h. Work up and column purification afforded 80 mg of 4. Repeat preparation with oxalylchloride (2.1 eq), THF (5.0 ml), DMSO (2.6 eq), −78° C., 30 min, 3 (300 mg, 0.98 mmol), −78° C., 30 min, TEA (5.4 eq), −78° C., 30 min, gradually warmed to RT for 30 min and stirred for 2 h. Work up and column purification afforded 230 mg of 4.

Preparation of UV-0079 (Also Called UV-79):

4 (315 mg, 1.03 mmol), MeOH (10 ml), DNJ (0.8 eq), AcOH (Cat.), RT, 20 min, NaCNBH3 (1.5 eq), RT, 16 h.

Crude LCMS showed 82% product formation. Purification by preparative HPLC [column Ascentis C-18 (250×21.2 mm, 10µ) (75 mg load per injection; CH$_3$CN: 0.05% TFA; T/B %: 0.1/95, 15/70, 25/50, 30/0, 35/0; as mobile phase; flow rate: 15 mL/min)] afforded 75 mg of UV-0079 with solvent traces. 72 mg UV-0079 was obtained after lyophilization with 99.0% purity by UPLC [column: Acquity BEH C-18 {50×2.1 mm, 1.7µ}; RT 1.45 min; ACN: 0.025% TFA (Aq); 0.5 mL/min], [M+H]$^+$ 451.1].

Example 8. Synthesis of UV-0080

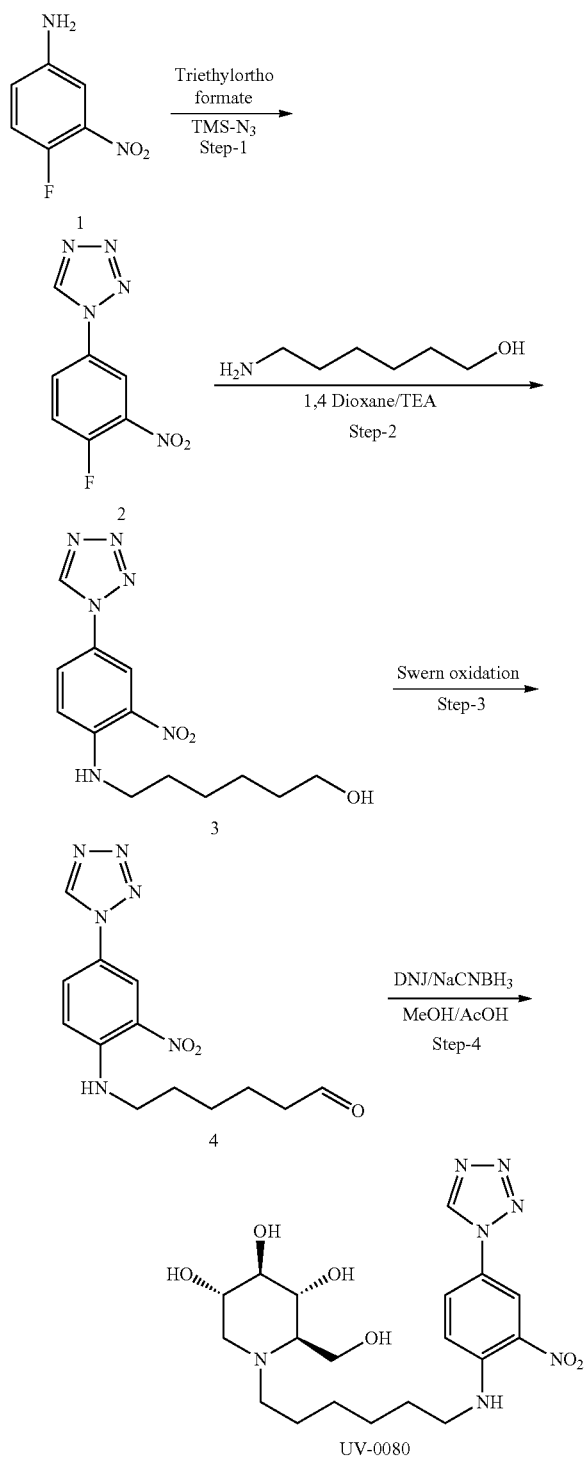

Preparation of 2:

1 (200 mg, 1.28 mmol), AcOH (5 mL), triethylorthoformate (5.0 eq), TMS-N3 (5.0 eq), 0° C. for 5 min; gradually warmed to 80° C. for 10 min and stirred for 4 h. Workup and column purification afforded 200 mg of 2. Repeat preparation with 1 (1.0 g, 6.41 mmol), AcOH (20 mL), triethylorthoformate (5.0 eq), TMS-N3 (5.0 eq), 0° C. for 5 min; gradually warmed to 80° C. for 10 min and stirred for 4 h. Workup and column purification afforded 900 mg of 2.

Preparation of 3:

2 (1.1 g, 5.26 mmol), 1,4-dioxane (20 mL), TEA (3.0 eq), aminohexanol (1.2 eq), RT for 5 min; gradually warmed to 80° C. for 10 min and stirred for 16 h. Work up and column purification afforded 1.0 g of 3.

Preparation of 4:

Oxalylchloride (2.1 eq), THF (10 mL), DMSO (2.6 eq), −78° C., 10 min, 3 (700 mg, 2.29 mmol), −78° C., 20 min, TEA (5.4 eq), −78° C. for 1 h, gradually warmed to RT for 1 h and stirred for 2 h. Work up and column purification afforded 650 mg of 4.

Preparation of UV-0080 (Also Called UV-80):

4 (650 mg, 2.13 mmol), MeOH (20 mL), DNJ (0.8 eq), AcOH (Cat.), NaCNBH3 (1.5 eq), RT, 16 h. LCMS showed 70% product formation. Preparative HPLC purification [column Ascentis C-18 (250×21.2 mm, 10µ) (100 mg loading; CH$_3$CN: 0.05% TFA; T/B %: 0.1/95, 2/95, 10/65, 20/50, 30/10, 35/10; as mobile phase; flow rate: 15 mL/min)] afforded 314 mg (29% yield) of UV-0080, purity 99.81% UPLC [column: Acquity BEH C-18 {50×2.1 mm, 1.7µ)}; RT 1.45 min; ACN: 0.025% TFA (Aq); 0.5 mL/min], [M+H]$^+$ 452.1 by LCMS.

Example 9. Synthesis of UV-0081

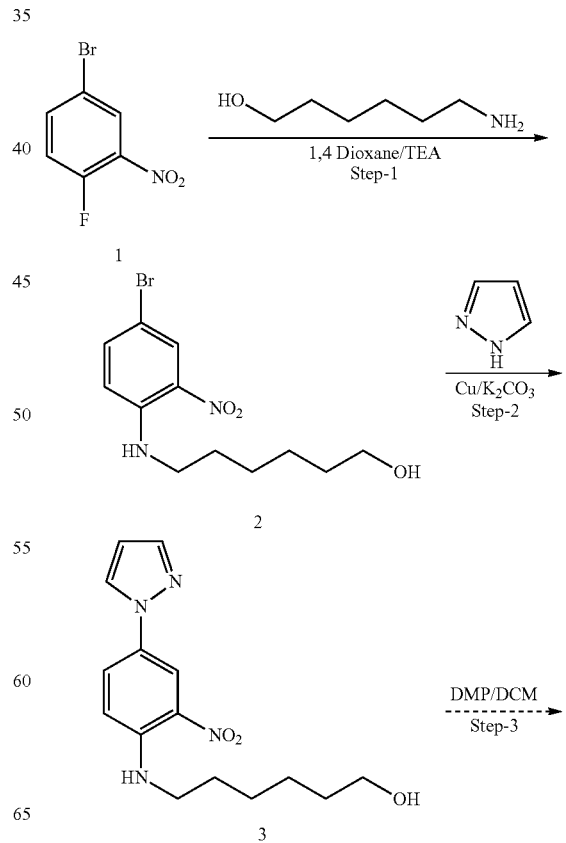

57

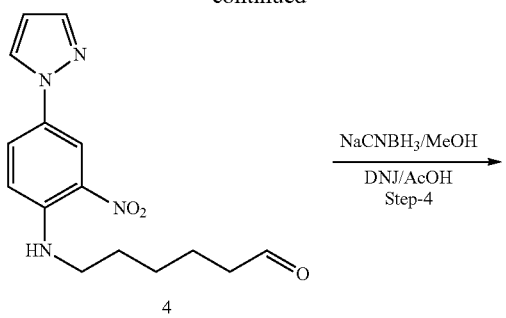

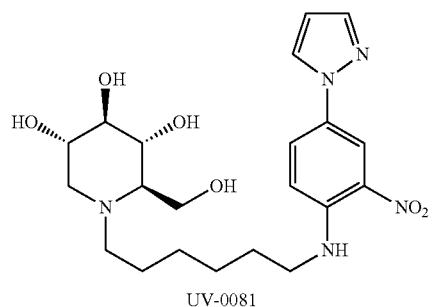

Preparation of 3:

2 (100 mg, 0.31 mmol), pyrazole (3.0 eq), Cu (2.5 eq), K2CO3 (2.0 eq), RT for 5 min; heated to 160° C. for 20 min and stirred for 16 h. Work up and column purification afforded 30 mg of 3. Repeat preparation of with 2 (2.0 g, 6.30 mmol), pyrazole (3.0 eq), Cu (2.5 eq), K2CO3 (2.0 eq), RT for 5 min; heated to 160° C. for 20 min and stirred for 16 h. Work up and column purification afforded 700 mg of 3.

Preparation of 4:

Oxalylchloride (2.1 eq), THF (5.0 ml), DMSO (2.6 eq), −78° C., 30 min, 3 (100 mg, 0.33 mmol), −78° C., 30 min, TEA (5.4 eq), −78° C., 30 min, gradually warmed to RT for 1 h and stirred for 2 h. Work up and column purification afforded 90 mg of 4. Repeat preparation with oxalylchloride (2.1 eq), THF (10.0 ml), DMSO (2.6 eq), −78° C., 30 min, 3 (600 mg, 1.98 mmol), −78° C., 30 min, TEA (5.4 eq), −78° C., 30 min, gradually warmed to RT for 1 h and stirred. After 2 h the reaction mass was quenched with water and extracted with EtOAc (2×50 mL). The combined organic layer was washed with water and dried over anhydrous Na2SO4, filtered and concentrated under reduced pressure to afford crude material which was purified by silica gel column chromatography [using 100-200 silica gel, eluting with 30% EtOAc-hexane] to afford 500 mg of 4.

Preparation of UV-0081 (Also Called UV-81):

4 (500 mg, 1.65 mmol), MeOH (20 ml), DNJ (0.8 eq), AcOH (Cat.), RT, 20 min, NaCNBH3 (1.5 eq), RT, and stirred for 16 h. LCMS showed 72% product formation. Crude material was triturated with ACN:H2O (1:1) (60 ml), ACN (40 ml), and EtOAc (40 ml) to afford 105 mg of UV-0081, purity 95.86% by UPLC [(column: Acquity BEH C-18 {50×2.1 mm, 1.7μ)}; RT 1.70 min; ACN: 0.025% TFA (Aq); 0.5 mL/min)], [M+H]+ 450.1

58

Example 10. Synthesis of UV-0082

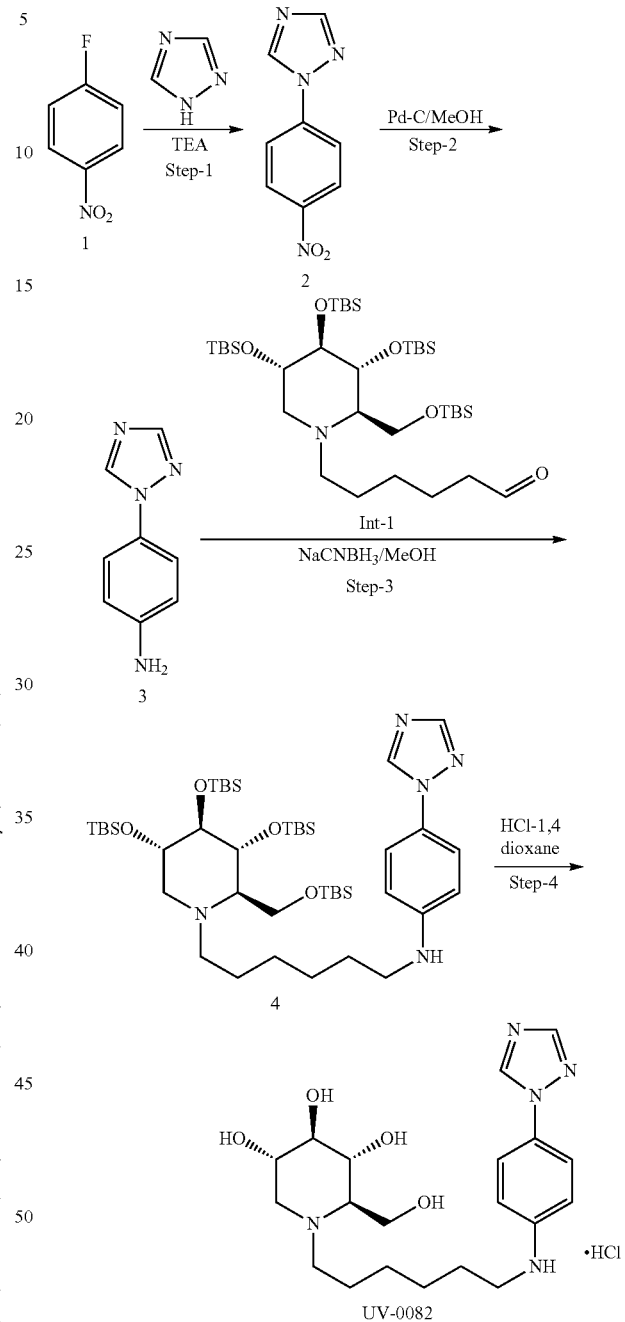

Preparation of 2:

1 (200 mg, 1.41 mmol), DMSO (3 mL), 1,2,4-triazole (1.1 eq), K2CO3 (3.0 eq), RT for 5 min; gradually heated to 80° C. for 10 min and stirred for 16 h. Work up and column purification afforded 120 mg of 2.

Preparation of 2:

1 (2.0 g, 14.1 mmol), DMSO (20 mL), 1,2,4-triazole (1.1 eq), K2CO3 (3.0 eq), RT for 5 min; gradually heated to 80° C. for 10 min and stirred for 16 h. Work up and column purification afforded 1.6 g of 2.

Preparation of 3:

2 (1.5 g, 8.42 mmol), MeOH (30 mL), Pd/C (1.0 g), RT, H2 (balloon pressure), 16 h. Work up and column purification afforded 1.2 g of 3.

Preparation of 4:

3 (160 mg, 1.00 mmol), MeOH (30 mL), Int-1 (also called Int-A, see above 900 mg, 1.25 mmol), AcOH (Cat.), NaCNBH3 (1.5 eq), RT, 20 h. Work up and column purification afforded 700 mg of 4.

Preparation of UV-0082 (Also Called UV-82):

4 (700 mg, 0.81 mmol), 1,4-dioxane (10 ml), 4M HCl in 1,4-dioxane (4 mL), 0° C. for 10 min and warmed to RT for 20 min and stirred for 16 h. Crude material was triturated with EtOAc (60 mL) and Et2O (80 mL) to afford 220 mg (50% yield) of UV-0082 with 95.75% purity by UPLC [column: Acquity BEH C-18 {50×2.1 mm, 1.7µ}; RT 1.10 min; ACN: 0.025% TFA (Aq); 0.5 mL/min)], [M+H]+ 406.5 by LCMS.

Example 11. Synthesis of UV-0083

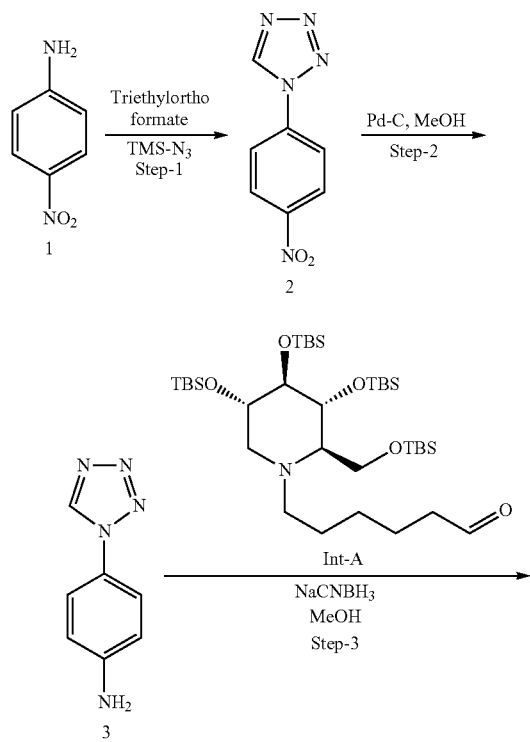

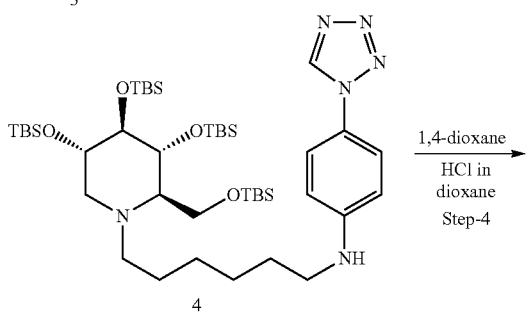

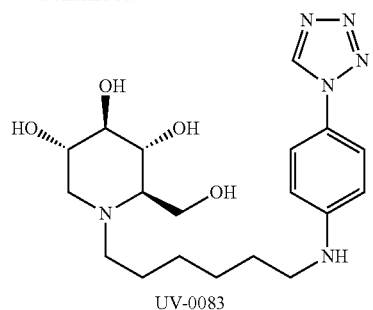

Preparation of 2:

1 (200 mg, 1.44 mmol), AcOH (5 mL), triethylorthoformate (5.0 eq), added TMS-N3 (5.0 eq), at 0° C. for 10 min; resulting reaction mixture was gradually warmed to 80° C. for 10 min and stirred for 4 h. Workup and column purification afforded 100 mg (37% yield) of 2. Repeat preparation with 1 (2.0 g, 14.49 mmol), AcOH (20 mL), triethylorthoformate (5.0 eq), added TMS-N3 (5.0 eq), at 0° C. for 10 min; resulting reaction mixture was gradually warmed to 80° C. for 10 min and stirred for 4 h. Workup and column purification afforded 1.2 g (40% yield) of 2.

Preparation of 3:

2 (1.0 g, 5.23 mmol), MeOH (20 mL), Pd/C (1.0 g), H2 (balloon pressure), RT, 24 h. Workup and column purification afforded 600 mg (71% yield) of 3.

Preparation of 4:

Int-A (see above, 700 mg, 0.97 mmol), MeOH (30 ml), 4 (0.8 eq), AcOH (Cat.), NaCNBH3 (1.5 eq), RT, 20 h. Work up and column purification afforded 410 mg (48% yield) of 4.

Preparation of UV-0083 (Also Called UV-83):

5 (410 mg, 0.50 mmol), 1,4-dioxane (4 ml), 4M HCl in 1,4-dioxane (5 mL), 0° C. for 10 min; gradually warmed to RT for 10 min and stirred for 16 h. Preparative HPLC purification [column Ascentis C-18 (250×21.2 mm, 10µ) (60 mg loading; CH3CN: 0.05% TFA; T/B %: 0.1/90, 2/90, 15/70, 25/30, 30/10, 35/10; as mobile phase; flow rate: 15 mL/min)] afforded 100 mg of UV-0083, 98.4% purity by UPLC [column: Acquity BEH C-18 {50×2.1 mm, 1.7µ}; RT 1.32 min; ACN: 0.025% TFA (Aq); 0.5 mL/min)], [M+H]1+ 407.6.

Example 12. Synthesis of UV-0084

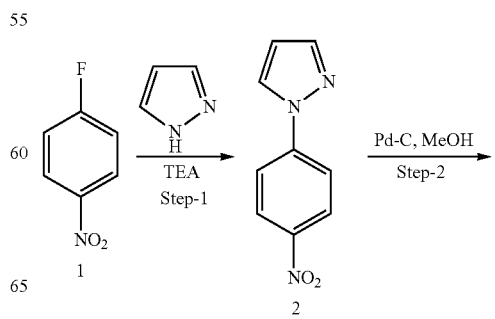

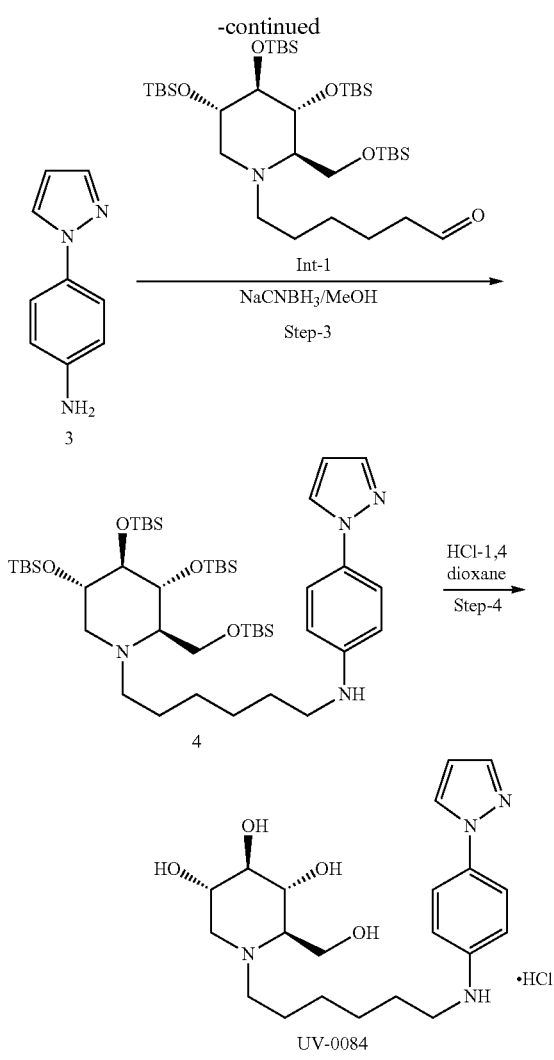

260 mg (46% yield) of UV-0084, purity 95.52% by UPLC [column: Acquity BEH C-18 {50×2.1 mm, 1.7µ}; RT 1.21 min; ACN: 0.025% TFA (Aq); 0.5 mL/min)], [M+H]⁺ 405.3.

Example 13. Synthesis of UV-0086

Preparation of 2:

1 (200 mg, 1.41 mmol), DMSO (3 mL), pyrazole (1.1 eq), K2CO3 (3.0 eq), at RT for 10 min; resulting reaction mixture was gradually warmed to 80° C. for 10 min and stirred for 16 h. Work up and column purification afforded 150 mg of 2. Repeat preparation with 1 (3.0 g, 21.5 mmol), DMSO (30 mL), pyrazole (1.1 eq), K2CO3 (3.0 eq), at RT for 10 min; resulting reaction mixture was gradually warmed to 80° C. for 10 min and stirred for 16 h. Purification afforded 2.1 g of 2.

Preparation of 3:

2 (2.0 g, 10.15 mmol), MeOH (40 mL), Pd/C (1.0 g), RT, hydrogen balloon pressure, 16 h. Purification afforded 1.5 g of 3.

Preparation of 4:

3 (160 mg, 1.00 mmol), MeOH (30 mL), Int-1 (900 mg, 1.25 mmol), AcOH (Cat.), NaCNBH3 (1.5 eq), RT, 20 h. Purification afforded 700 mg of 4.

Preparation of UV-0084 (Also Called UV-84):

4 (700 mg, 0.81 mmol), 1,4-dioxane (10 ml), 4M HCl in 1,4-dioxane (4 mL), 0° C. for 10 min; gradually warmed to RT for 10 min and stirred for 16 h. Crude material was triturated with EtOAc (60 mL) and Et2O (80 mL) to afford Preparation of 2:

Int-A (see above, 700 mg, 0.97 mmol), MeOH (30 ml), 1 (0.8 eq, desired isomer prepared as indicated for UV-0077), AcOH (Cat.), NaCNBH3 (1.5 eq), RT, 20 h. Work up and column purification afforded 250 mg of 2.

Preparation of UV-0086 (Also Called UV-86):

2 (250 mg, 0.29 mmol), 1,4-dioxane (2 ml), 4M HCl in 1,4-dioxane (3 mL), 0° C. for 10 min; gradually warmed to RT for 10 min and stirred for 16 h. Preparative HPLC purification [column Ascentis C-18 (250×21.2 mm, 10µ) (75 mg loading; CH₃CN: 0.05% TFA; T/B %: 0.1/90, 2/80, 15/70, 25/20, 30/10, 35/10; as mobile phase; flow rate: 15 mL/min)] afforded 8.0 mg of UV-0086, 98.29% purity by UPLC [(column: Acquity UPLC HSS-T3 {100×2.1 mm, 1.8µ}; RT 3.13 min; ACN: 0.025% TFA (Aq); 0.5 mL/min)], [M+H]⁺ 406.6.

Example 14. Synthesis of UV-0087

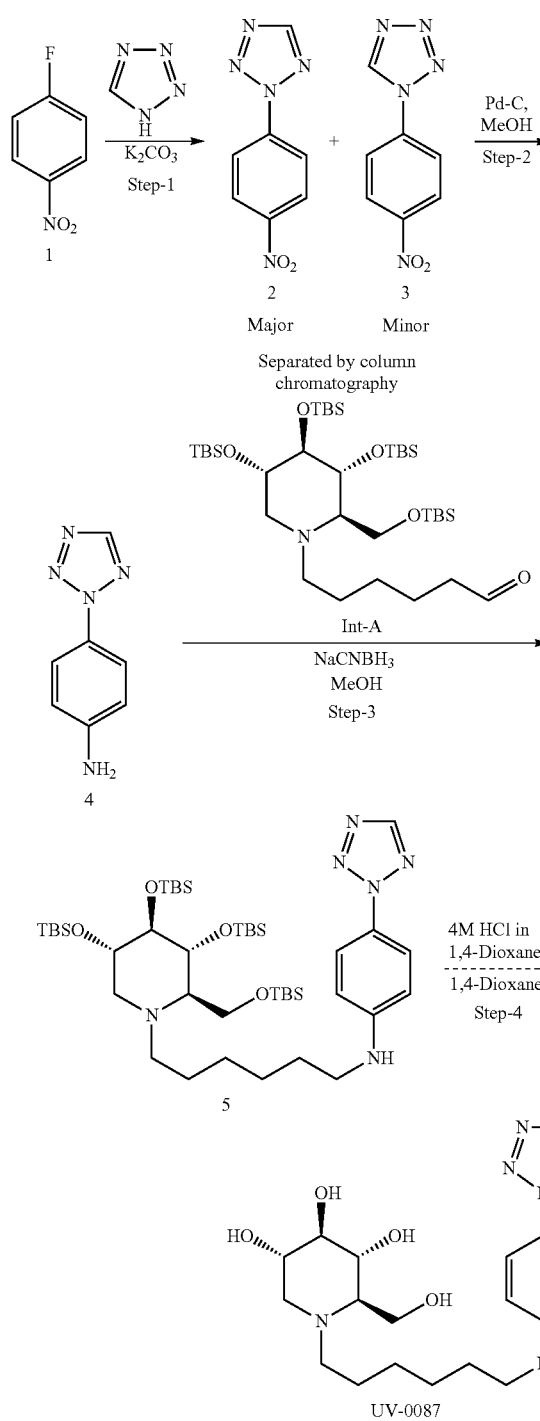

Preparation of 2:

1 (500 mg, 3.50 mmol), ACN (10 mL), K2CO3 (3.0 eq), 1H-tetrazole (1.5 eq), sealed tube, RT for 5 min; gradually warmed to 110° C. for 20 min and stirred for 16 h. Purification by column chromatography afforded 300 mg (44.3% yield) of 2 (confirmed by 1H-NMR and NOE). Repeat preparation of 2 used 1 (3.0 g, 21.00 mmol), ACN (60 mL), K2CO3 (3.0 eq), 1H-tetrazole (1.5 eq), sealed tube, RT for 5 min; gradually warmed to 110° C. for 20 min and stirred for 16 h. Purification by column chromatography afforded 1.90 g (47.5% yields) of 2.

Preparation of 4:

2 (1.0 g, 5.23 mmol), MeOH (20 mL), Pd/C (1.0 g), H2 (balloon pressure), RT, 24 h. After work up and column purification afforded 700 mg (83% yields) of 4.

Preparation of 5:

Int-A (see above, 700 mg, 0.97 mmol), MeOH (30 ml), 4 (0.8 eq), AcOH (Cat.), NaCNBH3 (1.5 eq), RT, 20 h. Work up and column purification afforded 400 mg (46% yield) of 5.

Preparation of UV-0087 (Also Called UV-87):

5 (400 mg, 0.44 mmol), 1,4-dioxane (4 ml), 4M HCl in 1,4-dioxane (5 mL), 0° C. for 10 min; gradually warmed to RT for 10 min and stirred for 16 h. Preparative HPLC purification [column Ascentis C-18 (250×21.2 mm, 10μ) (75 mg loading; CH$_3$CN: 0.05% TFA; T/B %: 0.1/95, 15/70, 25/50, 35/0, 45/0; as mobile phase; flow rate: 15 mL/min)] afforded 128 mg (65% yield) UV-0087, 99.9% purity by UPLC [(column: Acquity BEH C-18 {50×2.1 mm, 1.7μ}; RT 1.49 min; ACN: 0.025% TFA (Aq); 0.5 mL/min)], [M+H]$^+$ 407.1 by LCMS.

Example 15. Synthesis of UV-0089

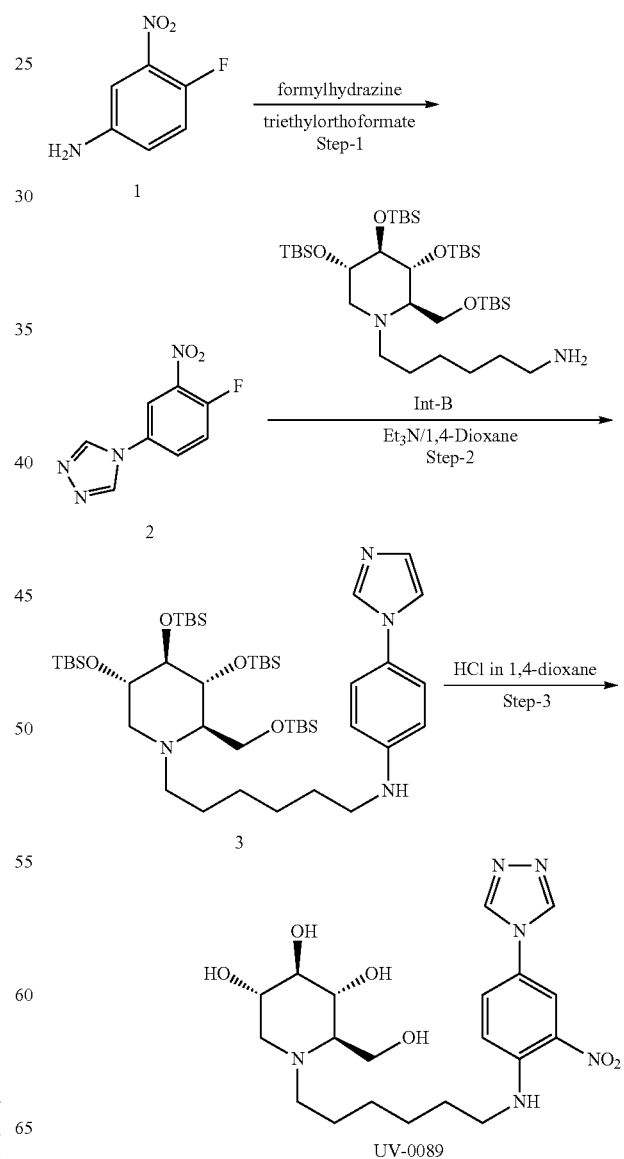

Preparation of Compound 2:

4-fluoro-3-nitro aminobenzene (200 mg, 1.28 mmol), AcOH (5 mL), triethylorthoformate (5.0 eq), formylhydrazine (5.0 eq), at 0° C. for 10 min; resulting reaction mixture was gradually warmed to 80° C. for 10 min and stirred at same temperature. After 24 h, starting material was completely consumed by TLC and two polar products were observed. The volatiles were removed under reduced pressure to obtain the crude. The obtained crude material was purified by silica gel (100-200 mesh) flash column chromatography by eluting with 5% MeOH-DCM to afford 100 mg (37.5% yield) of compound 2 as a red colour solid. Repeat preparation: 4-fluoro-3-nitro aminobenzene (2.0 g, 12.82 mmol), AcOH (15 mL), triethylorthoformate (5.0 eq), formylhydrazine (5.0 eq), at 0° C. for 10 min; resulting reaction mixture was gradually warmed to 80° C. for 10 min and stirred for 24 h. Starting material was completely consumed and two polar products were observed by TLC. The volatiles were removed under reduced pressure to obtain the crude product which was purified by silica gel (100-200 mesh) flash column chromatography by eluting with 5% MeOH-DCM to afford 1.1 g (41.3% yield) of compound 2 as a red colour solid.

Preparation of 3:

2 (300 mg, 0.41 mmol), Int-B (see below, 1.0 eq) 1,4-dioxane (10 mL), TEA (5.0 mL), at RT, resulting reaction mixture was gradually warmed to 80° C. for 10 min and stirred for 16 h. After 16 h, starting material was completely consumed by TLC and a new non-polar product was observed. The volatiles were removed under reduced pressure to afford the crude. The obtained crude material was purified by silica gel (100-200 mesh) flash column chromatography by eluting with 70% EtOAc-hexane to afford 200 mg (52.9% yield) of 3 as red color thick syrup.

Preparation of UV-0089 (Also Called UV-89):

3 (200 mg, 0.22 mmol), 1,4-dioxane (10 mL), 4M HCl in 1,4-dioxane (2.0 mL), 0° C. for 10 min; gradually warmed to RT for 10 min and stirred for 34 h. Reaction was monitored by LCMS. After 34 h, crude LCMS indicated 74% product formation. The volatiles were removed under reduced pressure to obtain 120 mg of crude material. The obtained crude material was purified by preparative HPLC [column Ascentis C-18 (250×20 mm, 5µ) (60 mg loading; CH$_3$CN: 0.05% TFA; T/B %: 0.1/95, 2/98, 15/70, 25/30, 30/10, 35/10; as mobile phase; flow rate: 15 mL/min)] to afford 20.5 mg (20.2% yield) of UV-0089 as orange-red thick syrup. 1H-NMR showed all the desired peaks along with traces amount of solvent peaks. 20 mg of pure UV-0089 was obtained after lyophilization as orange red syrup, purity 99.03% by HPLC [column: Eclipse-XDB-C18 (150×4.6 mm, 5.0 µm); RT 5.94 min; ACN: 0.025% TFA (Aq); 1.0 mL/min)], [M+H]$^+$ 451.1 by LCMS.

Synthesis of Int-B:

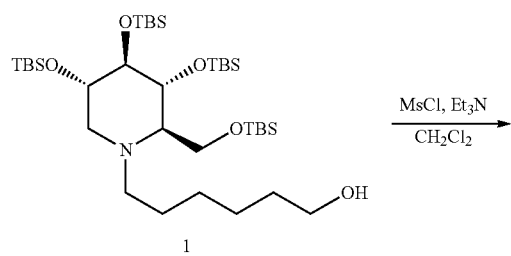

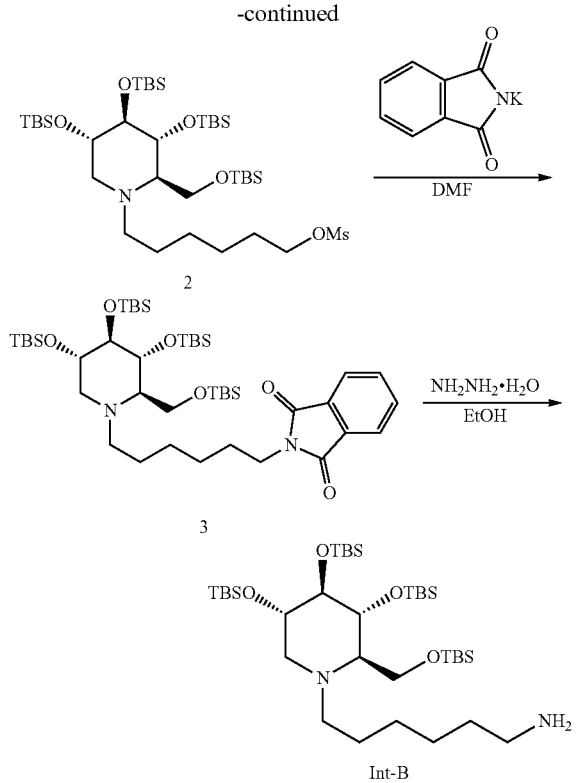

Preparation of 2:

To a stirred solution of 1 (20 g, 27.78 mmol, prepared as for Int-A) in CH$_2$Cl$_2$ (400 mL) were added triethylamine (16.64 mL, 119.44 mmol) at RT under argon atmosphere. The reaction mixture was cooled to 0° C. and added methanesulfonylchloride (2.82 mL, 36.11 mmol) drop wise. The reaction mixture was gradually warmed to RT for 15 min and stirred for 2 h. The reaction was monitored by TLC; after completion of the reaction, the reaction mixture was diluted with ice cold water (100 mL) and extracted with CH$_2$Cl$_2$ (3×100 mL). The combined organic extracts were dried over sodium sulfate, filtered and concentrated in vacuo to afford 2 (23 g) as colorless viscous syrup. This crude material was taken to the next step without further purification.

Preparation of 3:

To a stirred solution of 2 (23 g, crude) in DMF (150 mL) was added potassium phthalimide (8.13 g, 43.95 mmol) at RT under argon atmosphere. The reaction mixture was heated at 60° C. for 30 min and stirred for 16 h. The reaction was monitored by TLC; after completion of the reaction, the reaction was slowly cooled to RT for 30 min and diluted with ice cold water (100 mL). The product was extracted with EtOAc (3×100 mL) and organic layer was dried over sodium sulfate, filtered and concentrated in vacuo to obtain the crude. The crude was purified by silica gel column chromatography [using 100-200 mesh, eluting with 10% EtOAc-hexane] to afford 3 (18 g, 76% for two steps) as colorless viscous syrup.

Preparation of Int-B:

To a stirred solution of 3 (18 g, 19.74 mmol) in ethanol (360 mL) was added hydrazine hydrate (4.93 mL, 98.68 mmol) at RT under argon atmosphere and stirred for 16 h. Progress of reaction was monitored by TLC; after completion of the reaction, the reaction mixture was concentrated under reduced pressure. The obtained residue was diluted with ice cold water (100 mL) and extracted with EtOAc (3×100 mL). The combined organic extracts were dried over sodium sulfate, filtered and concentrated in vacuo to afford Int-B (13 g, 91%) as colorless viscous syrup. This material was taken to next step without further purification.

$^1$H NMR (500 MHz, CDCl$_3$): δ 3.97-3.95 (m, 1H), 3.75-3.61 (m, 4H), 3.49 (dd, J=9.8, 5.2 Hz, 1H), 2.88-2.72 (m, 3H), 2.71-2.63 (m, 4H), 1.49-1.40 (m, 3H), 1.35-1.22 (m, 4H), 0.90-0.86 (m, 36H), 0.09-0.01 (m, 24H).

Example 16. Synthesis of UV-0090

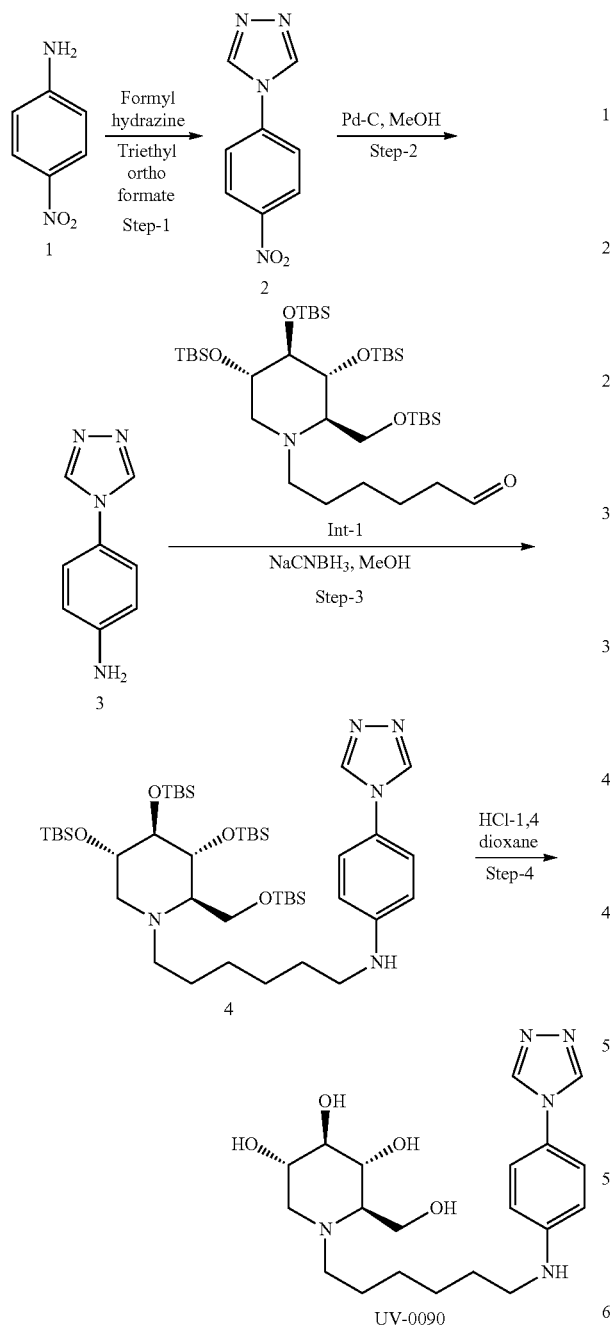

Preparation of 2:
1 (200 mg, 1.44 mmol), AcOH (5 mL), triethylorthoformate (5.0 eq), formylhydrazine (5.0 eq), at 0° C. for 10 min; resulting reaction mixture was gradually warmed to 80° C. for 10 min and stirred for 4 h. Workup and column purification afforded 120 mg (43% yield) of 2. Repeat preparation with 1 (2.0 g, 14.42 mmol), AcOH (20 mL), triethylorthoformate (5.0 eq), formylhydrazine (5.0 eq), at 0° C. for 10 min; resulting reaction mixture was gradually warmed to 80° C. for 10 min and stirred for 4 h. Workup and column purification afforded 1.2 g (43% yield) of 2.

Preparation of 3:
2 (1.2 g, 6.12 mmol), MeOH (20 mL), Pd/C (1.0 g), H2 (balloon pressure), RT, 16 h. Workup and column purification afforded 600 mg (47% yield) of 3.

Preparation of 4:
Int-1 (also called Int-A, see above, 700 mg, 0.97 mmol), MeOH (30 ml), 3 (0.8 eq), AcOH (Cat.), NaCNBH3 (1.5 eq), RT. Workup and column purification afforded 400 mg (47.6% yield) of 4.

Preparation of UV-0090 (Also Called UV-90):
4 (400 mg, 0.57 mmol), 1,4-dioxane (5 ml), 4M HCl in 1,4-dioxane (3 mL), 0° C. for 10 min; gradually warmed to RT for 10 min and stirred for 16 h. Preparative HPLC purification [column X-select CSH C-18 (250×19 mm, 5µ) (70 mg loading; CH$_3$CN: 5 mM NH$_4$OAc; T/B %: 0.1/95, 2/95, 10/70, 15/50, 25/10, 35/10; as mobile phase; flow rate: 15 mL/min)] followed by lyophilization afforded 20 mg of UV-0090, purity 99.42% by UPLC [column: Acquity UPLC HSS-T3 {100×2.1 mm, 1.8µ}; RT 2.87 min; ACN: 0.025% TFA (Aq); 0.5 mL/min], [M+H]$^+$ 406.6 by LCMS, $^1$H-NMR showed 3.4% NH4OAc after lyophilization.

Example 17. Synthesis of UV-0106

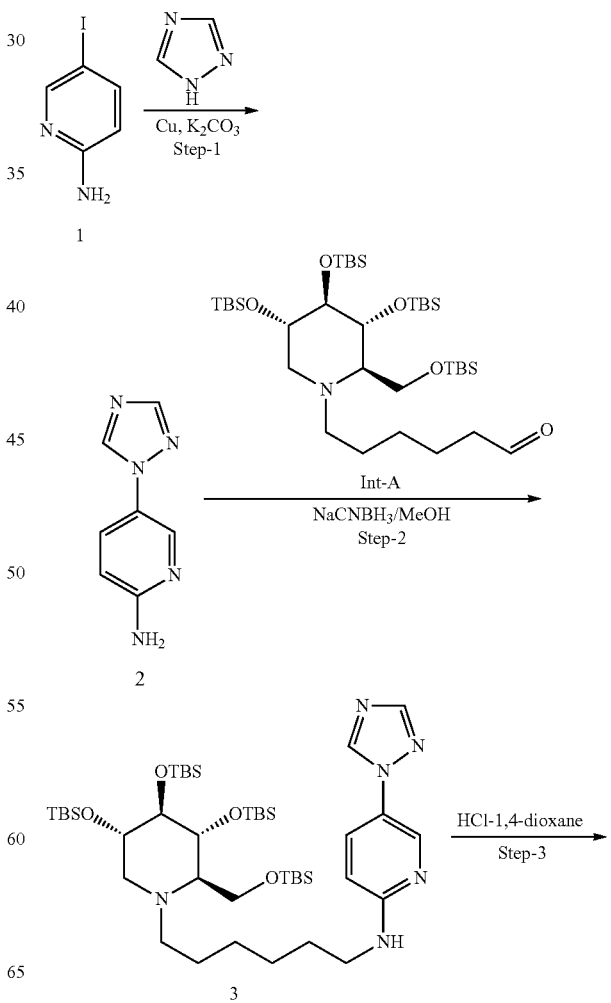

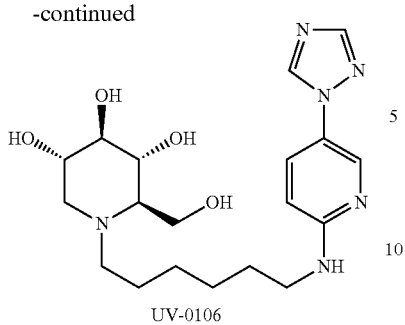

UV-0106

Preparation of 2:
1 (500 mg, 2.27 mmol), 1H-1,2,4-triazole (9.0 eq), Cu powder (2.1 eq), K2CO3 (2.0 eq), at RT; gradually warmed to 150° C. for 10 min and stirred for 4 h in a sealed tube. After 4 h, starting material was completely consumed and one polar product was observed by TLC. Reaction was diluted with ice-cold water and extracted with EtOAc (2×30 mL). The combined organic layer was dried over Na2SO4 filtered and concentrated under reduced pressure to afford the crude. The obtained crude material was purified by silica gel flash chromatography [using 100-200 mesh, eluting with 100% EtOAc] to afford 500 mg of 2 as white solid.

Preparation of 3:
Int-A (see above, 1.0 g, 1.30 mmol), MeOH (20 ml), 2 (2.0 eq), AcOH (cat.), NaCNBH3 (1.5 eq), RT, 16 h. One major non-polar product along with unreacted starting materials were observed by TLC. The volatiles were removed under reduced pressure; residue was quenched with ice-cold water (10 mL) and extracted with EtOAc (20 mL). The separated organic layer was dried over anhydrous Na2SO4, filtered and concentrated under reduced pressure to obtain the crude material. The major non-polar product was isolated by column chromatography 100-200 mesh silica gel by eluting with 20% EtOAc-hexane to afford 250 mg of 3 as thick syrup.

Preparation of UV-0106:
3 (250 mg, 0.29 mmol), 1,4-dioxane (5 mL), 4M HCl in 1,4-dioxane (2.5 mL), 0° C. for 10 min; gradually warmed to RT for 10 min and stirred for 16 h. After complete consumption of the starting material (monitored by TLC), the volatiles were removed under reduced pressure to afford the crude product which was purified by preparative HPLC [column YMC actus C-18 (250×20 mm, 5µ) (70 mg loading; CH3CN: 5 mM NH4HCO3; T/B %: 0.1/95, 3/95, 15/50, 25/30, 30/10, 35/10; as mobile phase; flow rate: 15 mL/min)] to afford 69.5 mg (60% yield) of UV-0106 as colorless thick syrup, purity 99.73% by UPLC [column: Acquity UPLC HSS-T3 {100×2.1 mm, 1.8µ)}; RT 3.45 min; ACN: 0.025% TFA (Aq); 0.5 mL/min)], [M+H]+ 407.1 by LCMS.

Example 18. Synthesis of UV-0107

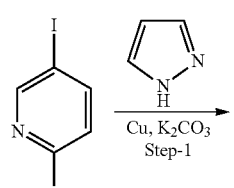

1

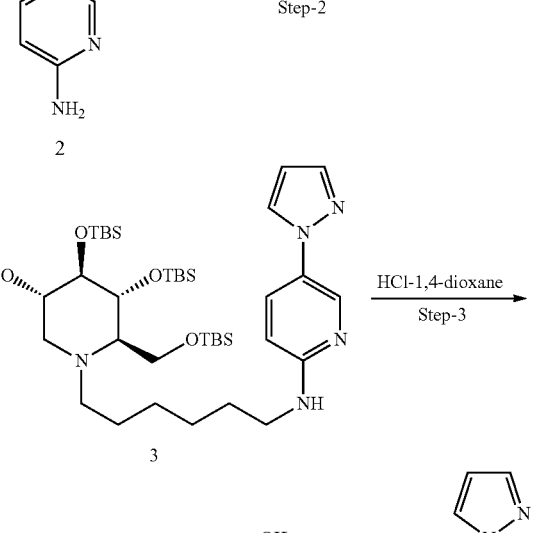

Preparation of 2:
1 (250 mg, 1.23 mmol), pyrazole (9.0 eq), Cu powder (2.1 eq), K2CO3 (2.0 eq), at RT; gradually warmed to 150° C. for 10 min and stirred for 4 h in a sealed tube. After 4 h, starting material was completely consumed and one polar product was observed by TLC. Reaction was diluted with ice-cold water and extracted with EtOAc (2×30 mL). The combined organic layer was dried over Na2SO4 filtered and concentrated under reduced pressure to afford the crude which was purified by silica gel flash chromatography [using 100-200 mesh, eluting with 100% EtOAc] to afford 100 mg (55% yield) of 2 as white solid.

Preparation of 3:
Int-A (600 mg, 0.83 mmol), MeOH (15 ml), 2 (0.8 eq), AcOH (cat.), NaCNBH3 (1.5 eq), RT, 16 h. One major non-polar product along with unreacted starting materials were observed by TLC. The volatiles were removed under reduced pressure; residue was quenched with ice-cold water (10 mL) and extracted with EtOAc (20 mL). The separated organic layer was dried over anhydrous Na2SO4, filtered and concentrated under reduced pressure to obtain the crude which was purified by silica gel column chromatography [using 100-200 mesh, eluting with 20% EtOAc-hexane] to afford 240 mg of 3 as thick syrup.

Preparation of UV-0107:

3 (240 mg, 1.0 eq), 1,4-dioxane (8 mL), 4M HCl in 1,4-dioxane (2.0 mL), 0° C. for 10 min; gradually warmed to RT for 10 min and stirred for 16 h. After complete consumption of the starting material (monitored by TLC), the volatiles were removed under reduced pressure to afford the crude material. Preparative HPLC purification [column YMC actus C-18 (250×20 mm, 5μ) (60 mg loading; CH$_3$CN: 0.05% TFA; T/B %: 0.1/98, 3/98, 15/80, 25/50, 30/10, 35/10; as mobile phase; flow rate: 15 mL/min)] afforded 44.9 mg (40% yield) of UV-0107 (as TFA salt based on chemical shift changes in 1H-NMR) as white solid with purity 99.77% by HPLC [column: Acquity UPLC HSS-T3 {100×2.1 mm, 1.8μ}; RT 3.55 min; ACN: 0.025% TFA (Aq); 0.5 mL/min], [M+H]$^+$ 406.2 by LCMS.

Example 19. Synthesis of UV-0109

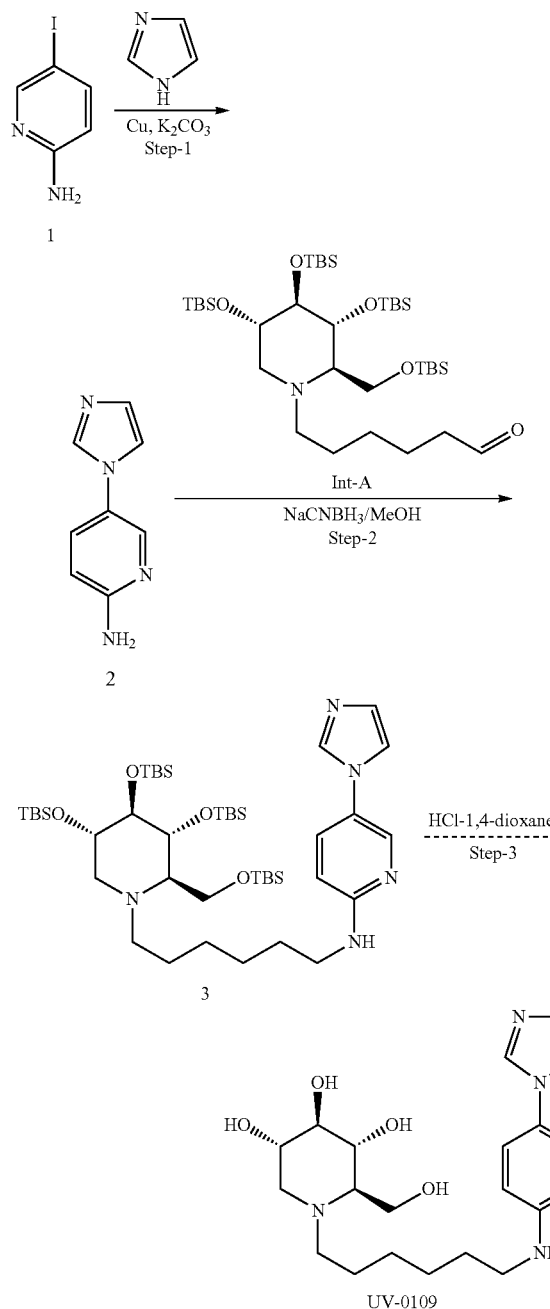

Preparation of 2:

1 (1 g, 4.54 mmol), imidazole (1 eq), Cu powder (2.1 eq), K2CO3 (2.0 eq), DMSO (4.0 mL), 150° C., sealed tube. After 4 h, starting material was completely consumed and one major-polar product was observed by TLC. The reaction was diluted with ice-cold water and extracted with EtOAc (2×50 mL). The combined organic layer was dried over Na2SO4 filtered and concentrated under reduced pressure to afford the crude. The obtained crude material was purified by silica gel flash chromatography [using 100-200 mesh, eluting with 5% MeOH-DCM] to afford 180 mg of 2 as white solid.

Preparation of 3:

Int-A (see above, 647 mg, 0.90 mmol), MeOH (15 ml), 2 (0.8 eq), AcOH (cat.), NaCNBH3 (1.5 eq), RT, 16 h. One major non-polar product along with both the unreacted starting materials were observed by TLC. The volatiles were removed under reduced pressure. The residue was quenched with ice-cold water (30 mL) and extracted with EtOAc (2×30 mL). The separated organic layer was dried over anhydrous Na2SO4, filtered and concentrated under reduced pressure to obtain the crude material. The major non-polar product was isolated by column chromatography [using 100-200 mesh, eluting with [3% MeOH-DCM] to afford 170 mg (22% yield) of 3 as thick syrup.

Preparation of UV-0109:

3 (170 mg, 0.19 mmol), 1,4-dioxane (3 mL), 4M HCl in 1,4-dioxane (2.0 mL), 0° C. for 10 min; gradually warmed to RT for 10 min and stirred. After 16 h, starting material was completely consumed and one polar product was observed by TLC. The volatiles were removed under reduced pressure to afford 100 mg of crude material which after preparative HPLC purification [column X-select CSH C-18 (250×19 mm, 5μ) (50 mg loading; CH$_3$CN: 0.05% TFA; T/B %: 0.1/98, 2/98, 10/85, 15/80, 20/10, 25/10; as mobile phase; flow rate: 15 mL/min)] afforded 50 mg (63% yield) of UV-0109 with 95.63% HPLC purity [column: Zorbax SB C-18 (150×4.6 mm, 3.5 μm); RT 1.86 min; ACN: 0.5% TFA (Aq); 1.0 mL/min)] and [M+H]$^+$ 406.1 by LCMS.

Example 20. Synthesis of UV-0110

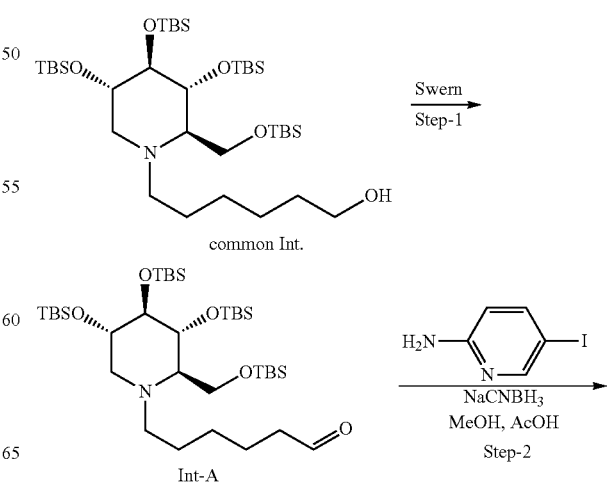

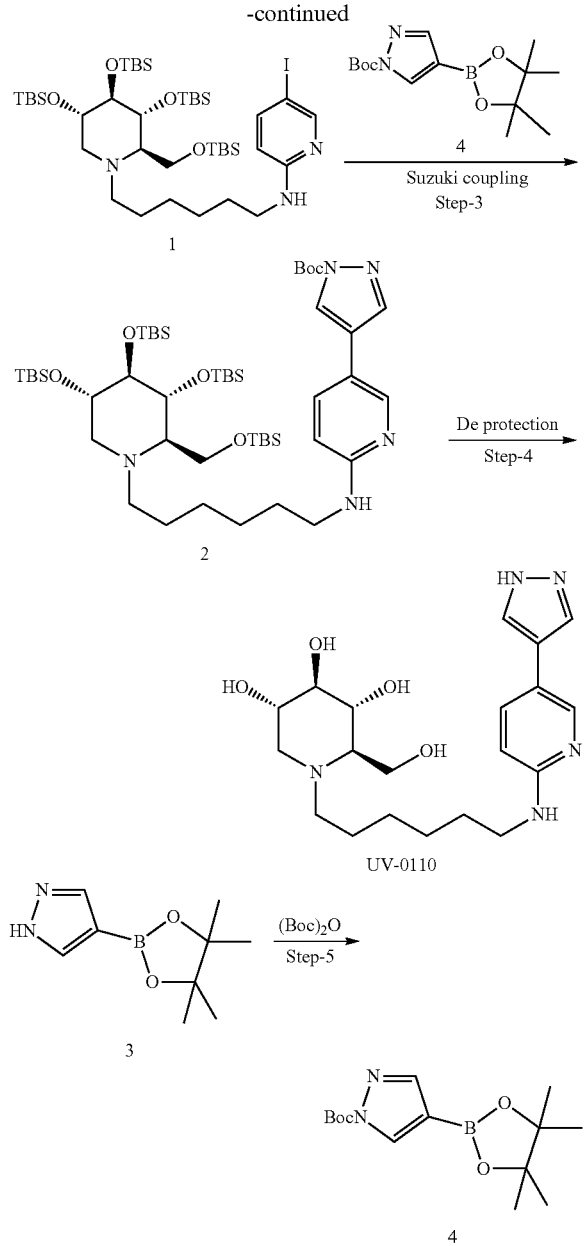

Preparation of 1:

Intermediate A (see above, Int-A, also called Int-1) was prepared by Swern oxidation of the indicated alcohol. Common intermediate alcohol (1.0 g, 1.30 mmol), MeOH (20 ml), 5-iodopyridin-2-amine (0.8 eq), AcOH (cat.), NaCNBH3 (1.5 eq), RT, 16 h. One major non-polar product along with both unreacted starting materials were observed by TLC. The volatiles were removed under reduced pressure. The residue was quenched with ice-cold water (10 mL) and extracted with EtOAc (20 mL). The separated organic layer was dried over anhydrous Na2SO4, filtered and concentrated under reduced pressure to obtain the crude material. The major non-polar product was isolated by column chromatography [using 100-200 mesh, eluting with 20% EtOAc-hexane] to afford 350 mg of 1 as thick syrup. Repeat preparation with Int-A (2.0 g, 2.60 mmol), MeOH (40 ml), 5-iodopyridin-2-amine (0.8 eq), AcOH (cat.), NaCNBH3 (1.5 eq), RT.

After 16 h, one major non-polar product along with unreacted starting materials were observed by TLC. The volatiles were removed under reduced pressure. The residue was quenched with ice-cold water (10 mL) and extracted with EtOAc (40 mL). The separated organic layer was dried over anhydrous Na2SO4, filtered and concentrated under reduced pressure to obtain the crude material. Column chromatography [using 100-200 mesh, eluting with 20% EtOAc-hexane] to afford 700 mg of 1 as thick syrup.

Preparation of 4:

3 (250 mg, 1.28 mmol), DCM (5 ml), TEA (3.0 eq), (Boc)2O (1.2 eq) DMAP (Cat.), RT. After 4 h, one major non-polar product was observed by TLC. The reaction was quenched with ice-cold water (10 mL) and extracted with DCM (20 mL). The separated organic layer was dried over anhydrous Na2SO4, filtered and concentrated under reduced pressure to afford 300 mg of 4 as thick syrup. Repeat preparatin with 3 (500 mg, 2.56 mmol), DCM (10 ml), TEA (3.0 eq), (Boc)2O (1.2 eq) DMAP (cat.), RT. After 4 h, one major non-polar product was observed by TLC. The reaction was quenched with ice-cold water (10 mL) and extracted with DCM (20 mL). The separated organic layer was dried over anhydrous Na2SO4, filtered and concentrated under reduced pressure to afford 500 mg of 4 as thick syrup. The obtained crude materials were used for next step without further purification.

Preparation of 2:

1 (50 mg, 0.05 mmol), 4 (1.0 eq), toluene (3.0 mL), EtOH (1.5 mL), sat. Na2CO3 (0.75 mL), degassed with argon for 30 min, Pd(dppf)Cl2 (0.1 eq), degassed with argon for 30 min, RT, resulting reaction mixture was gradually warmed to 80° C. for 10 min and stirred for 4 h. After 4 h, starting material was completely consumed and one major-polar product was observed by TLC. Reaction was diluted with ice-cold water and extracted with EtOAc (2×10 mL). The combined organic layer was dried over Na2SO4 filtered and concentrated under reduced pressure to afford the crude. The obtained crude material was purified by silica gel flash chromatography [using 100-200 mesh, eluting with 40% EtOAc in hexane] to afford 18 mg of 2 as color-less thick syrup. Repeat preparation with 1 (500 mg, 0.50 mmol), 4 (1.0 eq), toluene (10 mL), EtOH (5 mL), sat. Na2CO3 (2.5 mL), degassed with argon for 30 min, Pd(dppf)Cl2 (0.1 eq), degassed with argon for 30 min, RT, resulting reaction mixture was gradually warmed to 80° C. for 10 min and stirred for 4 h. After 4 h, starting material was completely consumed and one major-polar product was observed by TLC. Reaction was diluted with ice-cold water and extracted with EtOAc (2×20 mL). The combined organic layer was dried over Na2SO4 filtered and concentrated under reduced pressure to afford the crude. The obtained crude material was purified by silica gel flash chromatography [using 100-200 mesh, eluting with 40% EtOAc in hexane] to afford 320 mg of 2 as color-less thick syrup.

Preparation of UV-0110:

2 (330 mg, 0.34 mmol), 1,4-dioxane (3 mL), 4M HCl in 1,4-dioxane (3.0 mL), 0° C. for 10 min; gradually warmed to RT for 10 min and stirred for 16 h. The volatiles were removed under reduced pressure to afford 200 mg of crude material which after preparative HPLC purification [column X-select CSH C-18 (250×19 mm, (50 mg loading; CH3CN: 5 mM NH4HCO3; T/B %: 0.1/95, 2/95, 15/70, 25/55, 30/10, 35/10; as mobile phase; flow rate: 15 mL/min)] afforded 78 mg (56% yield) of UV-0110 as white solid with 99.62% purity by HPLC [column: YMC-Triart-C-18 (150×4.6 mm, 3.0 µm); RT 5.77 min; ACN: 0.05% TFA (Aq); 1.0 mL/min)] and [M+H]+ 406.1 by LCMS.

Example 21. Synthesis of UV-0125

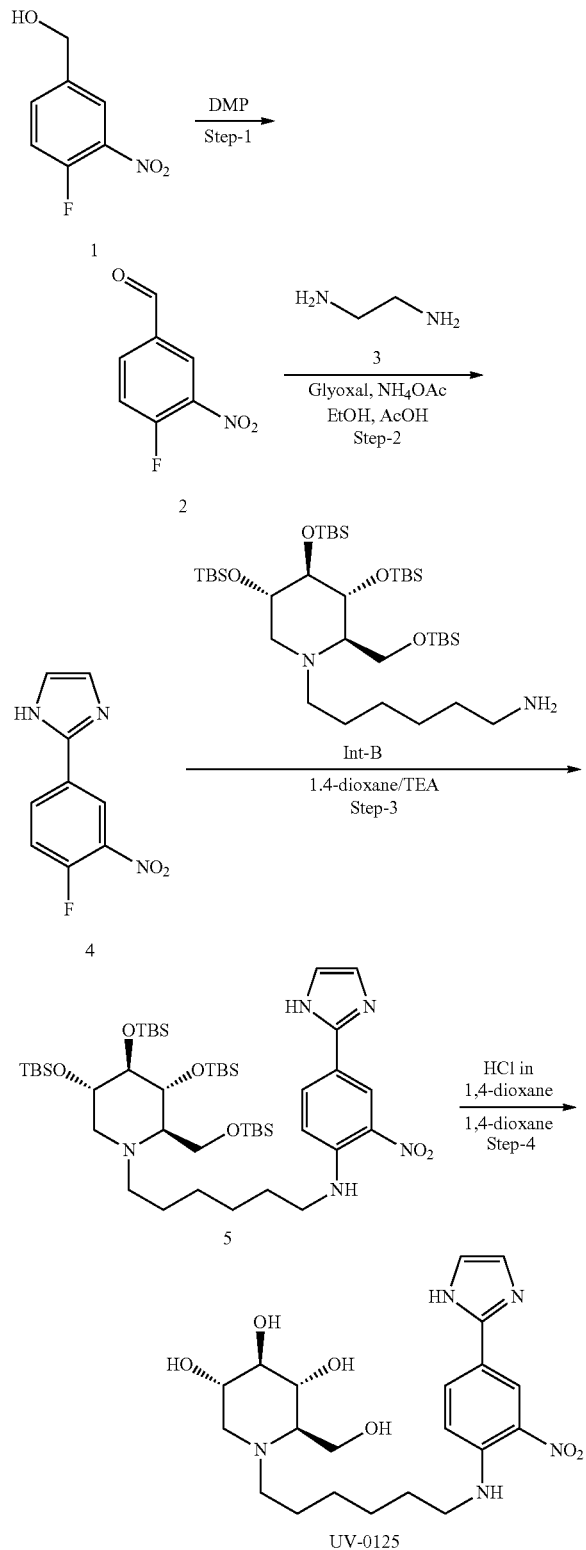

Preparation of 2:

1 (200 mg, 1.16 mmol), DCM (15 mL), DMP (1.5 eq), 0° C. for 20 min; gradually warmed to RT for 10 min and stirred for 2 h. After 2 h, a non-polar product was observed by TLC. The reaction was quenched with water and extracted with DCM (2×20 mL). The combined organic layer was washed with saturated NaHCO3, water and dried over anhydrous Na2SO4, filtered and concentrated under reduced pressure to afford the crude which was purified by silica gel column chromatography [using 100-200 mesh, eluting with 10% EtOAc-hexane] to afford 150 mg of 2. Repeat preparation with 1 (2 g, 11.6 mmol), DCM (100 mL), DMP (1.5 eq), 0° C. for 20 min; gradually warmed to RT for 10 min and stirred for 2 h. A non-polar product was observed by TLC. The reaction mixture was quenched with water and extracted with DCM (2×100 mL). The combined organic layer was washed with saturated NaHCO3, water and dried over anhydrous Na2SO4, filtered and concentrated under reduced pressure to afford the crude which was purified by silica gel column chromatography [using 100-200 mesh, eluting with 10% EtOAc-hexane] to afford 1.5 g of 2.

Preparation of 4:

2 (400 mg, 2.35 mmol), EtOH (4 mL), glyoxal (40% aq, 1.5 eq), NH4OAc (4 eq), AcOH (6 mL), RT for 10 min; then temperature was raised to 80° C. for 15 min and stirred for 8 h. After 8 h, a polar product along with starting material was observed by TLC. The volatiles were evaporated and the residue was quenched with sat. NaHCO3 and extracted with EtOAc (2×50 mL). The combined organic layer was washed with water and dried over anhydrous Na2SO4, filtered and concentrated under reduced pressure to afford the crude which was purified by silica gel column chromatography [using 100-200 mesh, eluting with 30% EtOAc-hexane] to afford 100 mg of 4.

Preparation of 5:

4 (100 mg, 0.48 mmol), 1, 4-dioxane (10 mL), TEA (2 mL), Int-B (1.2 eq), RT, resulting reaction mixture was gradually warmed to 80° C. for 10 min and stirred for 16 h. After 16 h, a polar product was observed by TLC. The volatiles were evaporated and the residue was quenched with water and extracted with EtOAc (2×50 mL). The combined organic layer was washed with water and dried over anhydrous Na2SO4, filtered and concentrated under reduced pressure to afford the crude which was purified by silica gel column chromatography [using 100-200 mesh, eluting with 30% EtOAc-hexane] to afford 300 mg of 5.

Preparation of UV-0125:

5 (300 mg, 0.33 mmol), 1, 4-dioxane (5 mL), 4M HCl in 1, 4-dioxane (2.0 mL), 0° C. for 20 min; gradually warmed to RT for 10 min and stirred for 16 h. After 16 h, crude LCMS indicated 60% product formation. The volatiles were removed under reduced pressure to obtain 200 mg of crude material. Preparative HPLC purification [column YMC actus C-18 (250×20 mm, 5µ) (75 mg loading; CH3CN: 5 mM NH4HCO3; T/B %: 0.1/95, 2/95, 8/70, 20/30, 20.01/0, 27/0; as mobile phase; flow rate: 15 mL/min)] afforded 25 mg of UV-0125 as orange red solid with 96.12% purity by HPLC [column: Zorbax SB C-18 (150×4.6 mm, 3.5 µm); RT 5.66 min; ACN: 0.5% TFA (Aq); 1.0 mL/min)], [M+H]+ 450.1 by LCMS.

Example 22. Synthesis of UV-0126

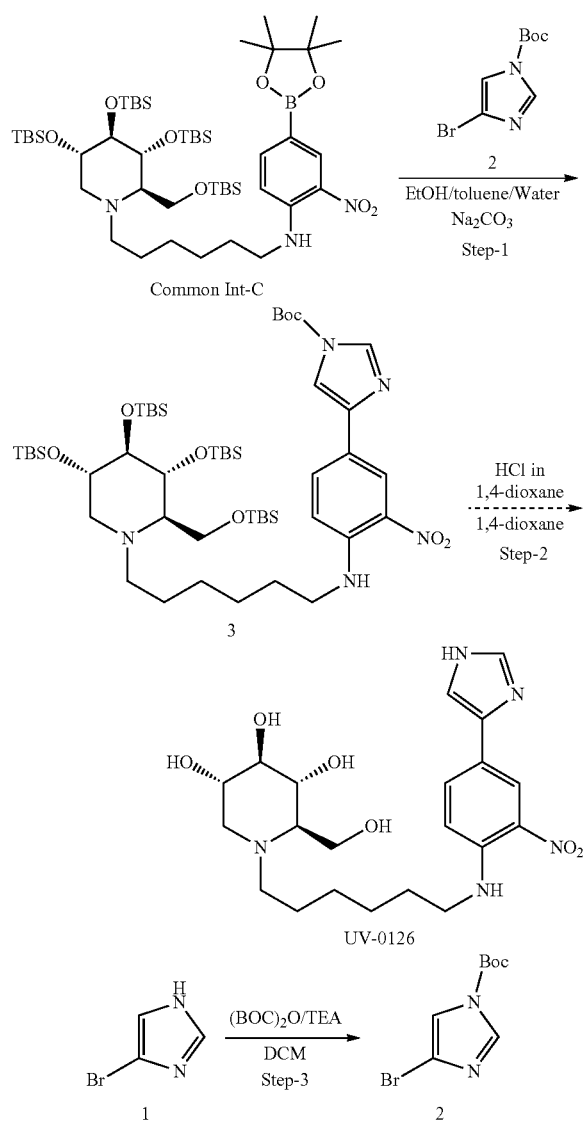

Preparation of 2:

1 (300 mg, 2.05 mmol), DCM (10 mL), TEA (3.0 eq), (Boc)2O (1.2 eq), 0° C. for 10 min; gradually warmed to RT for 10 min and stirred. After 16 h, a non-polar product was observed by TLC. The reaction was quenched with water and extracted with EtOAc (2×20 mL). The combined organic layer was washed with water and dried over anhydrous Na2SO4, filtered and concentrated under reduced pressure to afford the crude which was purified by silica gel column chromatography [using 100-200 mesh, eluting with 20% EtOAc-hexane] to afford 320 mg of 2 as white solid. Repeat preparation with 1 (1 g, 6.83 mmol), DCM (20 mL), TEA (3.0 eq), (Boc)2O (1.2 eq), 0° C.-RT. After 16 h, one non-polar product was observed by TLC. The reaction mixture was quenched with water and extracted with EtOAc (2×30 mL). The combined organic layer was washed with water and dried over anhydrous Na2SO4, filtered and concentrated under reduced pressure to afford the crude which was purified by silica gel column chromatography [using 100-200 mesh, eluting with 20% EtOAc-hexane] to afford 1.2 g of 2 as white solid.

Preparation of 3:

Common Int-C (150 mg, 0.15 mmol, see below), EtOH:toluene:water (1:1:1, 5 mL), 2 (1.0 eq), RT with degassing for 30 min, Na2CO3 (3.0 eq), Pd(dppf)Cl2 (0.1 eq), RT with degassing for 30 min, temperature increased to 80° C. over 15 mins and stirred.

After 4 h, a non-polar product was observed by TLC. The reaction was quenched with water and extracted with EtOAc (2×10 mL). The combined organic layer was washed with water and dried over anhydrous Na2SO4, filtered and concentrated under reduced pressure to afford the crude which was purified by silica gel column chromatography [using 100-200 mesh, eluting with 10% EtOAc-hexane] to afford 30 mg of 3 as yellow color thick syrup. Repeat preparation with Common Int-C (1.0 g, 1.03 mmol), EtOH:toluene:water (1:1:1, 20 mL), 2 (1.0 eq), RT, degassing, 30 min, Na2CO3 (3.0 eq), Pd(dppf)Cl2 (0.1 eq), RT, degassing, 30 min, temperature increased to 80° C. over 15 mins and stirred for 4 h. A non-polar product was observed by TLC. The reaction was quenched with water and extracted with EtOAc (2×10 mL). The combined organic layer was washed with water and dried over anhydrous Na2SO4, filtered and concentrated under reduced pressure to afford the crude which was purified by silica gel column chromatography [using 100-200 mesh, eluting with 10% EtOAc-hexane] to afford 130 mg of 3 as yellow color thick syrup.

Preparation of UV-0126

3 (150 mg, 0.14 mmol), 1,4-Dioxane (5 mL), 4M HCl in 1,4-Dioxane (1.5 mL), 0° C. for 15 min; gradually warmed to RT for 10 min and stirred for 24 h. After 24 h the volatiles were removed under reduced pressure to obtain 100 mg of crude material. Prep HPLC purification [column X-select CSH C-18 (250×19 mm, 5μ) (75 mg loading; $CH_3CN$: 5 mM $NH_4HCO_3$; T/B %: 0.1/95, 2/95, 8/70, 22/30, 25/10, 35/10; as mobile phase; flow rate: 15 mL/min)] afforded ~10 mg of UV-0126 as orange red thick syrup (96.649% purity by HPLC [column: X SELECT CSH C18 (150×4.6 mm, 3.5 μm); RT 7.17 min; ACN: 5 mM NH4OAC (Aq); 1.0 mL/min)], $[M+H]^+$ 450.4 by LCMS.

Preparation of Common Intermediate C (Int-C):

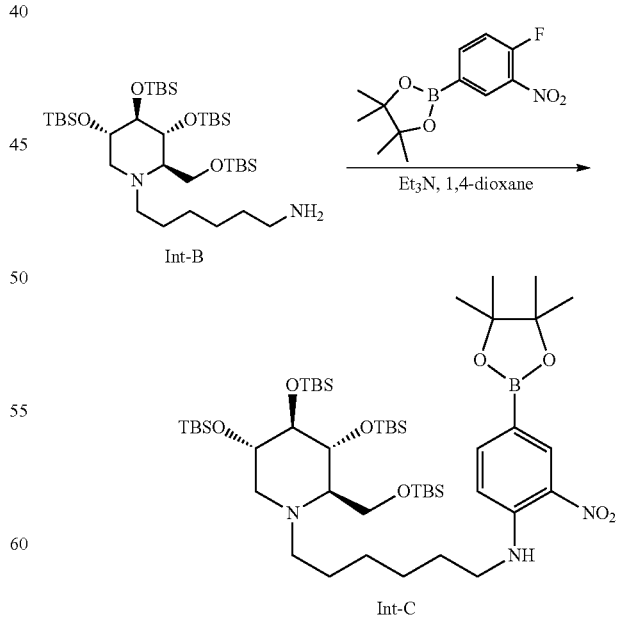

A stirred solution of 2-(4-fluoro-3-nitrophenyl)-4,4,5,5-tetramethyl-1,3,2-dioxaborolane (1.48 g, 5.56 mmol) and Int-B (5.0 g, 6.95 mmol) in 1,4-dioxane (100 mL) and triethylamine (25 mL) under argon atmosphere was heated to 60° C. for 30 min and stirred for 16 h. The reaction was monitored by TLC. After completion of the reaction the volatiles were removed in vacuo. The residue was diluted with water (50 mL) and extracted with EtOAc (3×50 mL). The combined organic extracts were dried over sodium sulfate, filtered and concentrated in vacuo to afford Int-C (5.0 g) as yellow viscous syrup. This crude material was taken to the next step without further purification.

$^1$H NMR (500 MHz, CDCl$_3$): δ 8.64 (d, J=1.4 Hz, 1H), 8.17 (brs, 1H), 7.81 (dd, J=8.5, 1.3 Hz, 1H), 6.81 (d, J=8.7 Hz, 1H), 4.59-4.54 (m, 1H), 4.26-4.24 (m, 1H), 4.09-3.99 (m, 1H), 3.94-3.84 (m, 3H), 3.81-3.60 (m, 3H), 3.55-3.28 (m, 5H), 3.24-3.13 (m, 1H), 1.99-1.88 (m, 1H), 1.79-1.72 (m, 2H), 1.55-1.48 (m, 2H), 1.34 (s, 12H), 0.93-0.90 (m, 36H), 0.17-0.11 (m, 24H)

Example 23. Synthesis of UV-0127

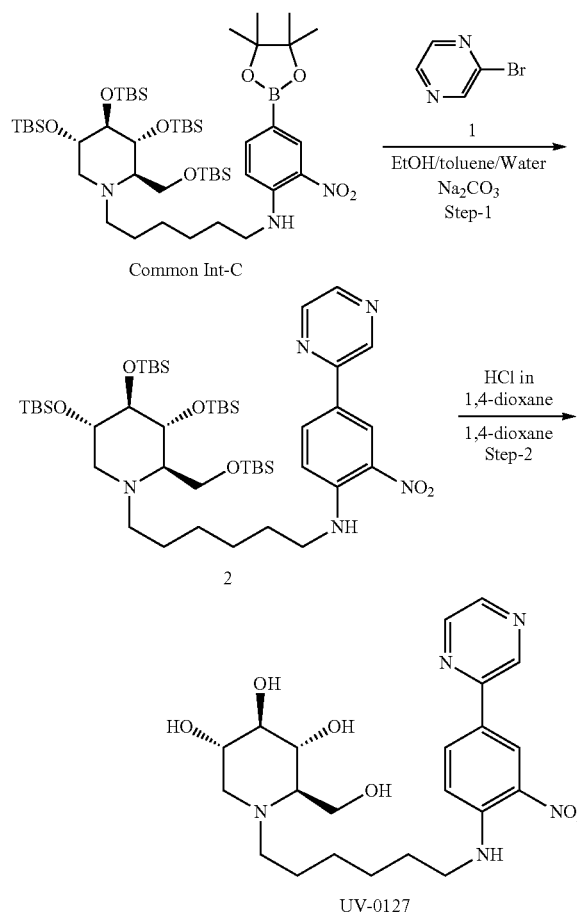

Preparation of 2:

Common Int-C (700 mg, 0.72 mmol), EtOH:toluene:water (1:1:1, 15 mL), 2 (1.0 eq), RT, degassing, 30 min, Na2CO3 (3.0 eq), Pd(dppf)Cl2 (0.1 eq), reaction mixture was purged under argon at RT for 30 min; resulting reaction mixture was gradually warmed to 80° C. for 10 min and stirred for 7 h; Starting material was completely consumed and a polar product was observed by TLC. The reaction was diluted with ice-cold water and extracted with DCM (2×30 mL). The combined organic layer was dried over Na2SO4 filtered and concentrated under reduced pressure to afford crude. The obtained crude material was purified by silica gel column chromatography [using 100-200 mesh, eluting with 20% EtOAc-hexane] to afford 300 mg of 2.

Preparation of UV-0127:

2 (200 mg, 0.21 mmol), 1,4-Dioxane (5 mL), 4M HCl in 1,4-Dioxane (2.0 mL), 0° C. for 15 min; gradually warmed to RT for 10 min and stirred. After 24 h, crude LCMS indicated 85% product formation. The volatiles were removed under reduced pressure to afford 150 mg of crude material which after preparative HPLC purification [column X-select CSH C-18 (250×19 mm, 5μ) (75 mg loading; CH$_3$CN: 5 mM NH$_4$HCO$_3$; T/B %: 0.1/95, 2/95, 10/65, 22/30, 25/10, 35/10; as mobile phase; flow rate: 15 mL/min)] afforded 36 mg of UV-0127 as yellow color solid with 98.77% purity by HPLC [column: Zorbax SB C-18 (150×4.6 mm, 3.5 μm); RT 6.15 min; ACN: 0.5% TFA (Aq); 1.0 mL/min)], [M+H]$^+$ 462.1 by LCMS.

Example 24. Synthesis of UV-0128

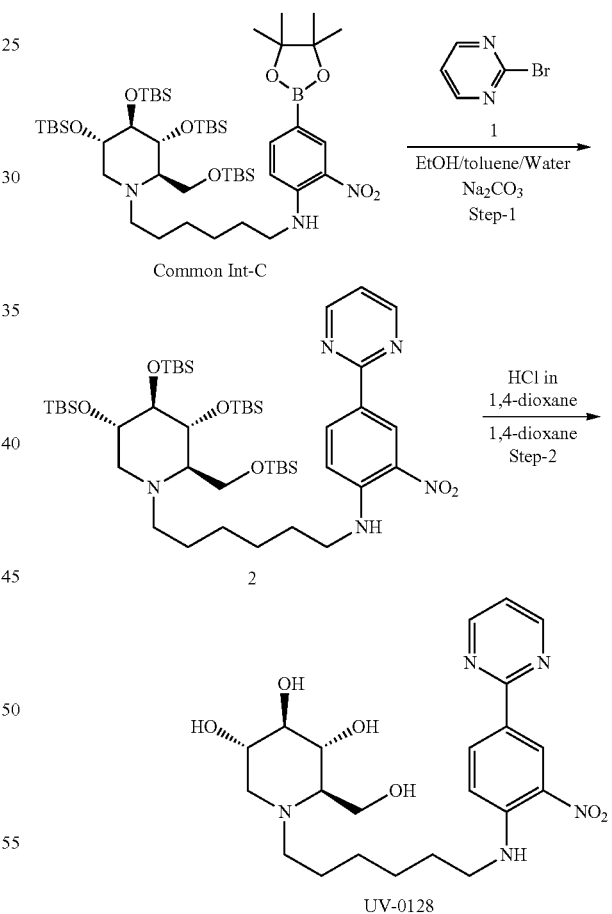

Preparation of 2:

Common Int-C (350 mg, 0.36 mmol, see above), EtOH:toluene:water (1:1:1, 10 mL), 1 (1.0 eq), RT and the reaction mixture was purged under argon for 30 min, Na2CO3 (3.0 eq), Pd(dppf)Cl2 (0.1 eq) was added and purged again under argon at RT for 30 min; resulting reaction mixture was gradually warmed to 80° C. for 15 min and stirred for 7 h. After 7 h, starting material was completely consumed and one polar product was observed by TLC. The reaction was diluted with ice-cold water and extracted with DCM (2×30 mL). The combined organic layer was dried over Na2SO4 filtered and concentrated under reduced pressure to afford crude. The obtained crude material was purified by silica gel column chromatography [using 100-200 mesh, eluting with 20% EtOAc-hexane] to afford 200 mg of 2.

Preparation of UV-0128:

2 (200 mg, 0.21 mmol), 1,4-Dioxane (5 mL), 4M HCl in 1,4-Dioxane (2.0 mL), 0° C. for 15 min; gradually warmed to RT for 10 min and stirred for 24 h. After 24 h, crude LCMS indicated 90% product formation. The volatiles were removed under reduced pressure to obtain 120 mg of crude material. Prep HPLC purification [column X-select CSH C-18 (250×19 mm, 5µ) (75 mg loading; CH$_3$CN: 5 mM NH$_4$HCO$_3$; T/B %: 0.1/95, 2/95, 10/65, 22/30, 25/10, 35/10; as mobile phase; flow rate: 15 mL/min)] afforded 42.2 mg of UV-0128 as yellow color solid (purity 97.61% by HPLC [(column: Zorbax SB C-18 (150×4.6 mm, 3.5 µm); RT 6.35 min; ACN: 0.5% TFA (Aq); 1.0 mL/min)], [M+H]$^+$ 462.1 by LCMS).

Example 25. Synthesis of UV-0128 (Alternative)

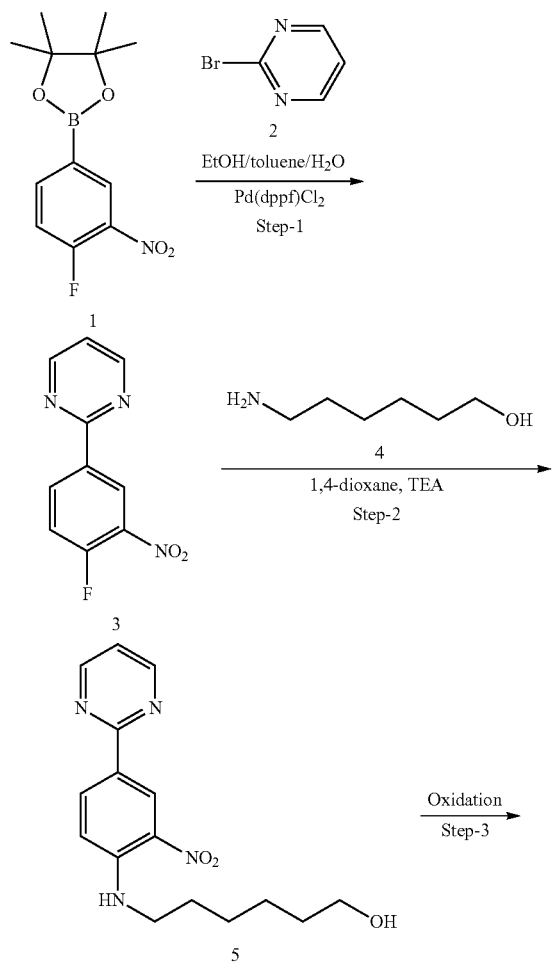

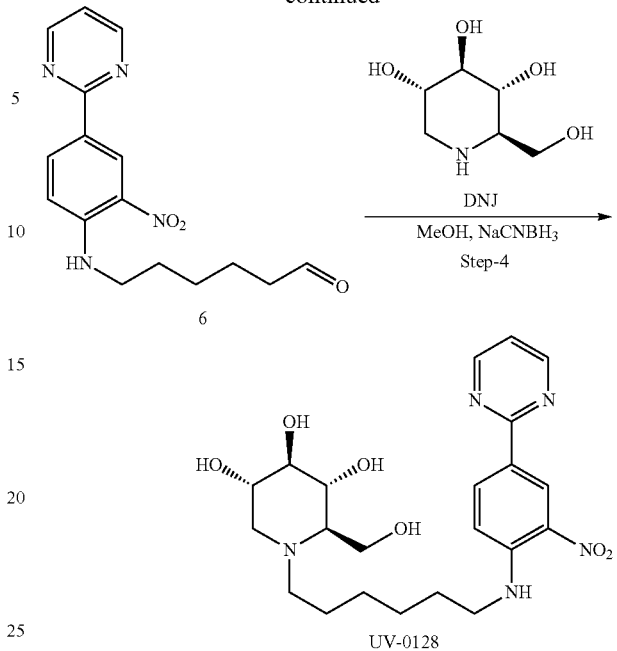

Preparation of 3:

1 (500 mg, 1.87 mmol), EtOH:toluene:water (1:1:1, 15 mL), 2 (1.2 eq), RT, degassing, 30 min, Na2CO3 (3.0 eq), Pd(dppf)2Cl2 (0.1 eq), RT, degassing, 30 min, resulting reaction mixture was gradually warmed to 80° C. for 15 min and stirred for 2 h. After 2 h, one non-polar product was observed by TLC. The reaction was quenched with water and extracted with EtOAc (2×30 mL). The combined organic layer was washed with water and dried over anhydrous Na2SO4, filtered and concentrated under reduced pressure to afford the crude which was purified by silica gel column chromatography [using 100-200 mesh, eluting with 30% EtOAc-hexane] to afford 380 mg of 3 as yellow color solid.

Preparation of 5:

3 (380 mg, 1.73 mmol), 1,4-dioxane (15 mL), TEA (3.0 eq), 4 (1.5 eq), RT, resulting reaction mixture was gradually warmed to 80° C. for 15 min and stirred for 4 h. After 4 h, one polar product was observed by TLC. The reaction was quenched with water and extracted with EtOAc (2×30 mL). The combined organic layer was washed with water and dried over anhydrous Na2SO4, filtered and concentrated under reduced pressure to afford the crude which was purified by silica gel column chromatography [using 100-200 mesh, eluting with 50% EtOAc-hexane] to afford 400 mg of 5 as yellow color solid.

Preparation of 6:

[Oxalyl chloride (2.0 eq), THF (5.0 ml), DMSO (4.0 eq), −78° C., 10 min, 5 (200 mg, 0.63 mmol), −78° C., 20 min, TEA (4.0 eq), −78° C. for 1 h, temperature raised to RT for 1 h and stirred for 2 h. After 3 h, starting material was completely consumed and a non-polar product was observed by TLC. Reaction was diluted with ice-cold water and extracted with EtOAc (2×20 mL). The combined organic layer was washed with water and dried over Na2SO4 filtered and concentrated under reduced pressure to afford crude material which was purified by silica gel (100-200) flash column chromatography by eluting with 20% EtOAc-hexane to afford 180 mg of 6 as colorless thick syrup.

Preparation of UV-0128:

6 (180 mg, 0.57 mmol), MeOH (10 mL), THF (5 mL), DNJ (0.8 eq), AcOH (cat), NaCNBH3 (1.5 eq), RT, 16 h. Crude LCMS indicated 87% product formation. The volatiles were removed under reduced pressure to obtain 250 mg of crude material with purity 87.27% by HPLC before purification, [column: X SELECT CSH C18 (150×4.6 mm, 3.5 μm); RT 8.52 min; ACN: 5 mM NH4HCO3 (Aq); 1.0 mL/min)], [M+H]$^+$ 462.2 by LCMS.

Example 26. Synthesis of UV-0129

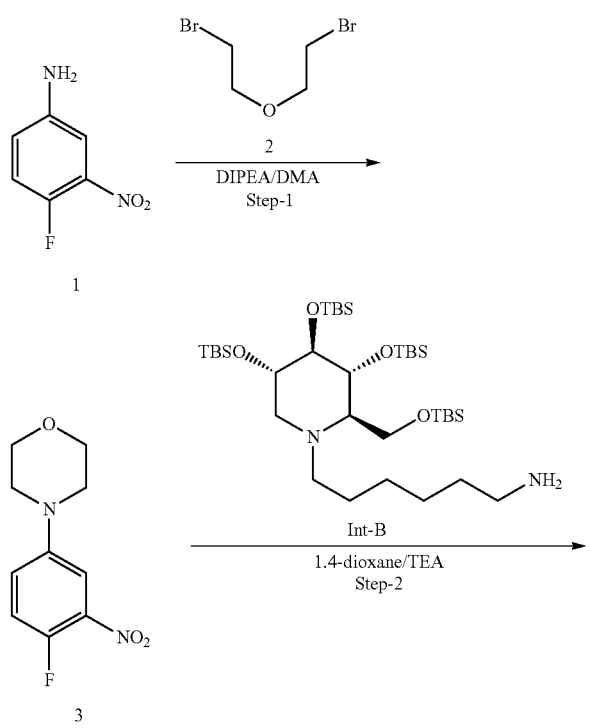

Preparation of 3:

1 (1.0 g, 6.41 mmol), 2 (1.5 eq), DIPEA (5 mL), DMA (10 mL), RT, resulting reaction mixture was gradually warmed to 100° C. for 10 min and stirred for 16 h. After 16 h a non-polar product was observed by TLC. The reaction was quenched with water and extracted with EtOAc (2×30 mL). The combined organic layer was washed with water and dried over anhydrous Na2SO4, filtered and concentrated under reduced pressure to afford the crude material. The obtained crude material was purified by silica gel column chromatography [using 100-200 mesh, eluting with 50% EtOAc-hexane] to afford 500 mg of 3 as yellow color solid.

1HNMR data complies.

Preparation of 4:

3 (100 mg, 0.44 mmol), TEA (5 mL), Int-B (1.2 eq), sealed tube, RT, resulting reaction mixture was gradually warmed to 100° C. for 10 min and stirred. After 16 h, a non-polar product along with starting material (1:1) was observed by TLC. The reaction mixture was quenched with water and extracted with EtOAc (2×30 mL). The combined organic layer was washed with water and dried over anhydrous Na2SO4, filtered and concentrated under reduced pressure to afford crude material which was purified by silica gel column chromatography [using 100-200 mesh, eluting with 20% EtOAc-hexane] to afford 250 mg of 4 as yellow color thick syrup.

Preparation of UV-0129:

4 (250 mg, 0.27 mmol), 1,4-dioxane (5 mL), 4M HCl in 1, 4-dioxane (2.5 mL), 0° C. for 15 min; gradually warmed to RT for 10 min and stirred for 24 h. Crude LCMS indicated 88% product formation. The volatiles were removed under reduced pressure to afford 180 mg of crude material. Preparative HPLC purification [column X-select CSH C-18 (250×19 mm, 5μ) (75 mg loading; CH3CN: 5 mM NH4HCO3; T/B %: 0.1/95, 2/95, 10/65, 20/30, 25/10, 35/10; as mobile phase; flow rate: 15 mL/min)] afforded 53.4 mg of UV-0129 as orange red thick syrup with 99.27% purity by HPLC [column: Zorbax SB C-18 (150×4.6 mm, 3.5 μm); RT 4.88 min; ACN: 0.5% TFA (Aq); 1.0 mL/min)], [M+H]$^+$ 469.1 by LCMS).

Example 27. Synthesis of UV-0131

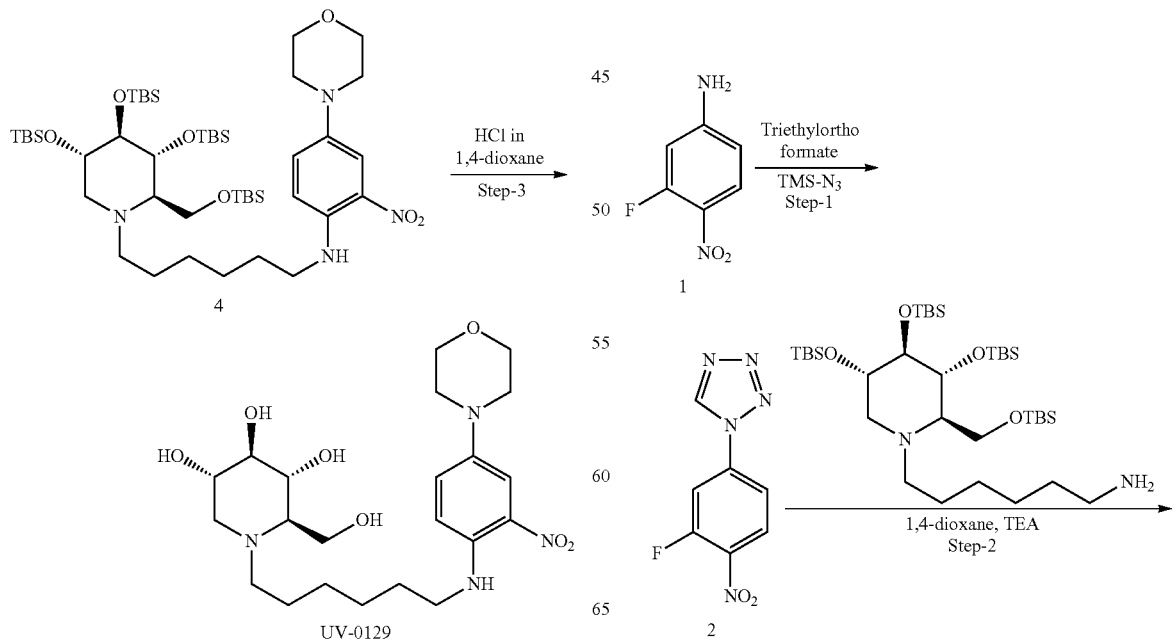

Example 28. Synthesis of UV-0132

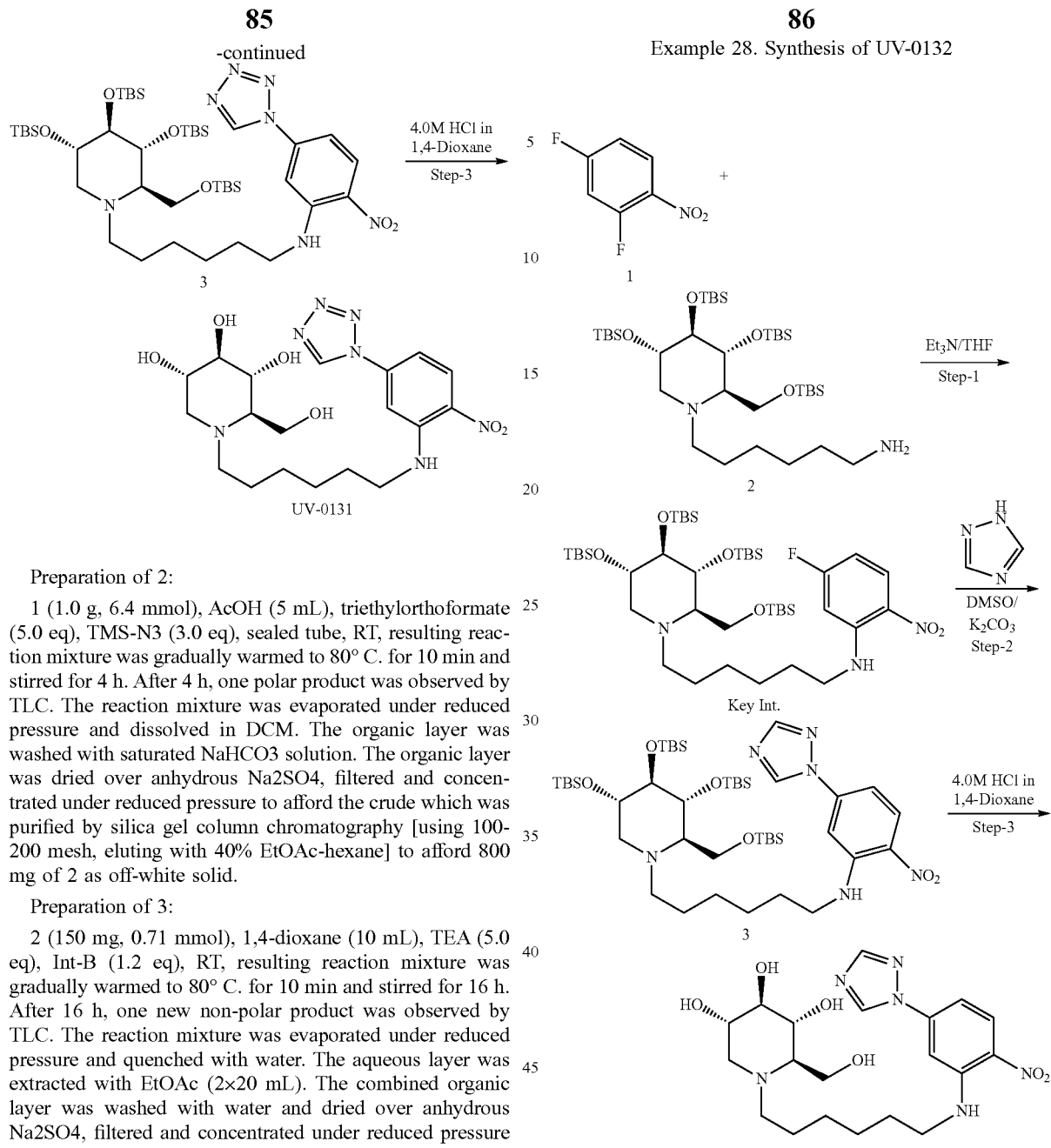

Preparation of 2:

1 (1.0 g, 6.4 mmol), AcOH (5 mL), triethylorthoformate (5.0 eq), TMS-N3 (3.0 eq), sealed tube, RT, resulting reaction mixture was gradually warmed to 80° C. for 10 min and stirred for 4 h. After 4 h, one polar product was observed by TLC. The reaction mixture was evaporated under reduced pressure and dissolved in DCM. The organic layer was washed with saturated NaHCO3 solution. The organic layer was dried over anhydrous Na2SO4, filtered and concentrated under reduced pressure to afford the crude which was purified by silica gel column chromatography [using 100-200 mesh, eluting with 40% EtOAc-hexane] to afford 800 mg of 2 as off-white solid.

Preparation of 3:

2 (150 mg, 0.71 mmol), 1,4-dioxane (10 mL), TEA (5.0 eq), Int-B (1.2 eq), RT, resulting reaction mixture was gradually warmed to 80° C. for 10 min and stirred for 16 h. After 16 h, one new non-polar product was observed by TLC. The reaction mixture was evaporated under reduced pressure and quenched with water. The aqueous layer was extracted with EtOAc (2×20 mL). The combined organic layer was washed with water and dried over anhydrous Na2SO4, filtered and concentrated under reduced pressure to afford the crude which was purified by silica gel column chromatography [using 100-200 mesh, eluting with 20% EtOAc-hexane] to afford 300 mg of 3 as yellow colored thick syrup.

Preparation of UV-0131:

3 (300 mg, 0.31 mmol), 1, 4-Dioxane (5 mL), 4M HCl in 1,4-dioxane (3.0 mL), 0° C. for 15 min; gradually warmed to RT for 10 min and stirred for 24 h. After 24 h crude LCMS indicated 73% product formation. The volatiles were removed under reduced pressure to obtain 150 mg of crude material. Preparative HPLC purification [column YMC actus C-18 (250×20 mm, 5μ) (75 mg loading; CH3CN: 5 mM NH4HCO3; T/B %: 0.1/95, 2/95, 8/60, 20/30, 30/10, 35/10; as mobile phase; flow rate: 15 mL/min)] afforded 35 mg of UV-0131 as yellow color solid, purity 97.49% by HPLC [column: Zorbax SB C-18 (150×4.6 mm, 3.5 μm); RT 6.72 min; ACN: 0.5% TFA (Aq); 1.0 mL/min)], [M+H]+ 452.2 by LCMS.

Preparation of Key Fluorinated Intermediate:

1 (800 mg, 0.78 mmol), THF:TEA (1:1, 40 mL), 2 (Int-B, as shown in scheme as 2, 1.2 eq), RT; resulting reaction mixture was gradually warmed to 70° C. for 10 min and stirred for 16 h. A non-polar product was observed by TLC. The reaction was quenched with water and extracted with EtOAc (2×30 mL). The combined organic layer was washed with water, dried over anhydrous Na2SO4, filtered and concentrated under reduced pressure to afford crude which was purified by silica gel column chromatography [100-200 mesh, eluting with 10% EtOAc-hexane] to afford 1.6 g of fluorinated intermediate as yellow color thick syrup.

Preparation of 3:

Key Int (also referred as key fluorinated intermediate, 300 mg, 0.35 mmol), DMSO (5 mL), 1H-1,2,4 triazole (1.5 eq), K2CO3 (2.5 eq), RT, resulting reaction mixture was gradually warmed to 130° C. for 10 min and stirred for 16 h. A polar product was observed by TLC. The reaction was quenched with water and extracted with EtOAc (2×20 mL). The combined organic layer was washed with water and dried over anhydrous Na2SO4, filtered and concentrated under reduced pressure to afford crude material which was purified by silica gel column chromatography [100-200 mesh, eluting with 10% EtOAc-hexane] to afford 150 mg of 3 as yellow color thick syrup.

Preparation of UV-0132:

3 (150 mg, 0.35 mmol), 1,4-dioxane (5 mL), 4M HCl in 1,4-dioxane (2.0 mL), 0° C. for 15 min; gradually warmed to RT for 10 min and stirred for 24 h. Crude LCMS indicated 83% product formation. The volatiles were removed under reduced pressure to obtain 100 mg of crude material. Preparative HPLC purification [column YMC actus C-18 (250× 20 mm, 5μ) (50 mg loading; CH$_3$CN: 5 mM NH$_4$OAc; T/B %: 0.1/95, 2/95, 10/55, 22/30, 22.01/0, 30/0; as mobile phase; flow rate: 15 mL/min)] afforded 18.9 mg of UV-0132 as yellow solid with 99.87% purity by HPLC [column: ATLANTIS T3 (150×4.6 mm, 3.0 μm); RT 7.65 min; ACN: 5 mM NH4OAC (Aq); 1.0 mL/min)], [M+H]$^+$ 451.1 by LCMS.

Example 29. Synthesis of UV-0133

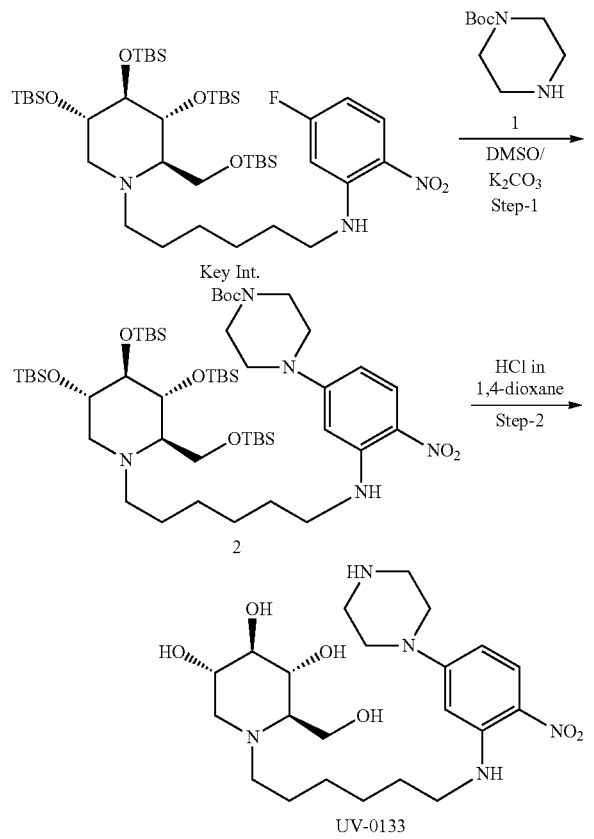

Preparation of 2

Key fluorinated intermediate prepared as for UV-0132 (300 mg, 0.35 mmol), DMSO (5 mL), 3 (1.5 eq), K2CO3 (2.5 eq), RT; resulting reaction mixture was gradually warmed to 130° C. for 10 min and stirred for 16 h. One polar product was observed by TLC. The reaction was quenched with water and extracted with EtOAc (2×20 mL). The combined organic layer was washed with water and dried over anhydrous Na2SO4, filtered and concentrated under reduced pressure to afford crude which was purified by silica gel column chromatography [100-200 mesh, eluting with 30% EtOAc-hexane] to afford 200 mg of 2 as yellow color thick syrup.

Preparation of UV-0133:

2 (200 mg, 0.19 mmol), 1,4-dioxane (5 mL), 4M HCl in 1,4-dioxane (3.0 mL), 0° C. for 15 min; gradually warmed to RT for 10 min and stirred for 24 h. After 24 h crude LCMS indicated 70% product formation. The volatiles were removed under reduced pressure to afford 150 mg of crude material. Preparative HPLC purification [column X-select CSH C-18 (250×19 mm, 5μ) (50 mg loading; CH$_3$CN: 5 mM NH$_4$HCO$_3$; T/B %: 0.1/95, 2/95, 15/65, 25/30, 30/10, 35/10; as mobile phase; flow rate: 15 mL/min)] afforded 71.5 mg of UV-0133 as yellow colored solid, 99.25% purity by HPLC [column: X SELECT CSH C18 (150×4.6 mm, 3.5 μm); RT 6.76 min; ACN: 5 mM NH4OAC (Aq); 1.0 mL/min)], [M+H]+ 468.1 by LCMS.

Example 30. Synthesis of UV-0136

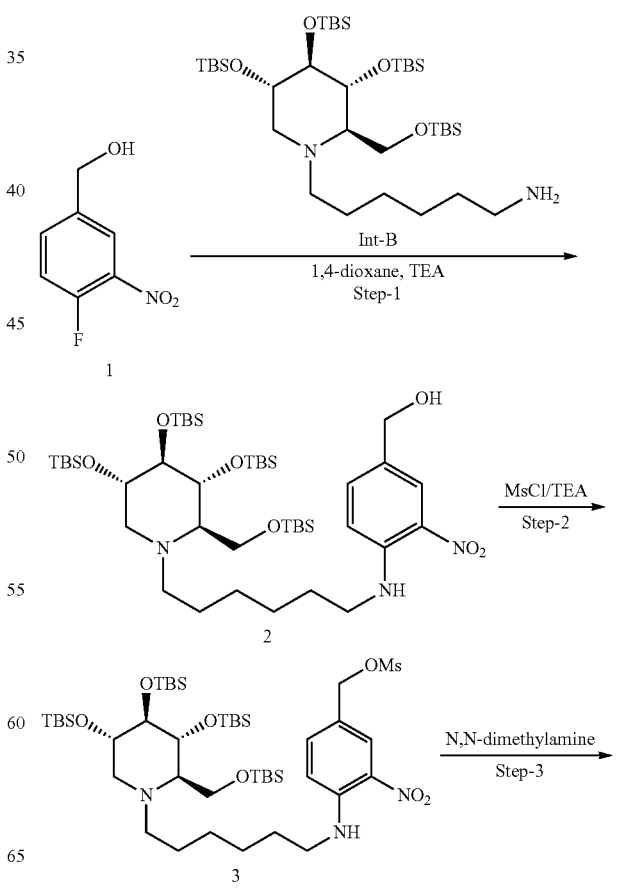

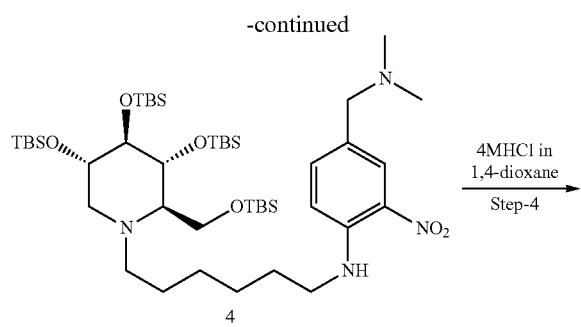

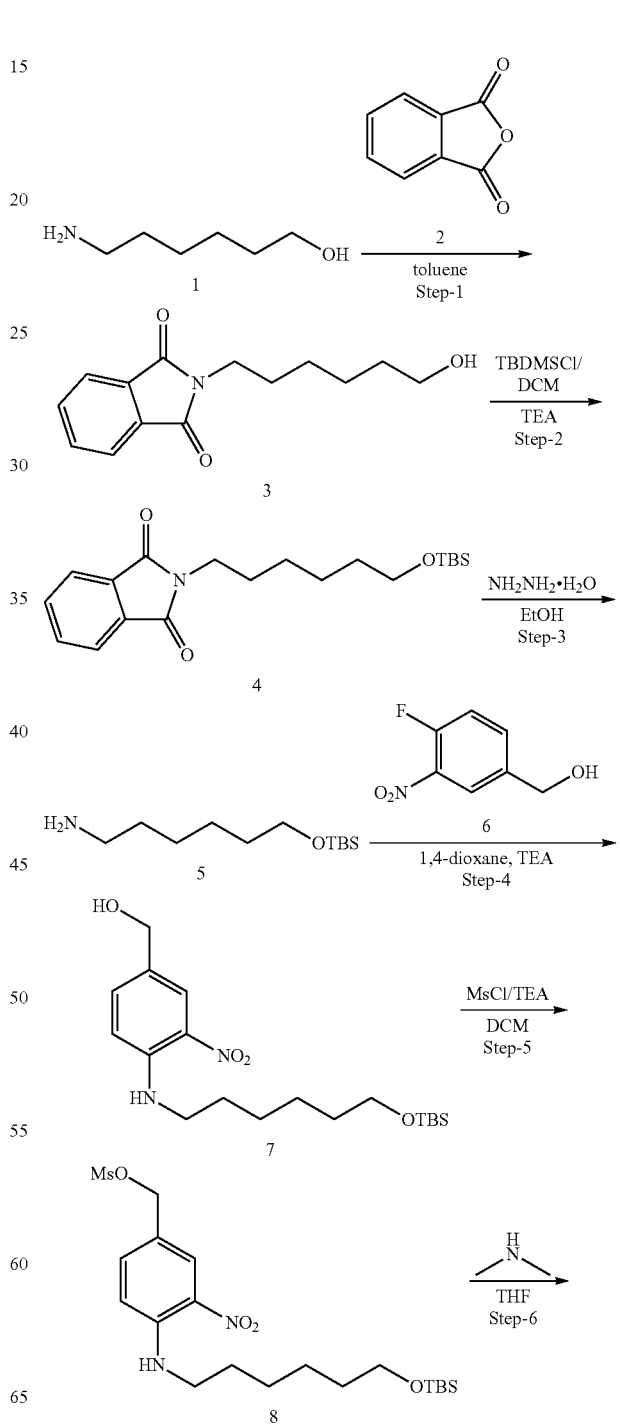

Preparation of 2:

To a stirred solution of Int-B (4 g, 5.55 mmol) in 1,4-dioxane (30 mL) were added triethylamine (TEA, 20 mL) and (4-fluoro-3-nitrophenyl)methanol (665 mg, 3.89 mmol) at RT under argon atmosphere. The reaction mixture was heated to 70° C. for 30 and maintained for 6 h. The reaction was monitored by TLC. After completion of the reaction the volatiles were removed in vacuo to obtain the crude material which was purified by silica gel column chromatography [using 100-200 mesh, eluting with 20% EtOAc-hexane] to afford compound 2 (2 g, 42%) as an orange syrup.

Preparation of 3:

To a stirred solution of compound 2 (1.2 g, 1.38 mmol) in $CH_2Cl_2$ (30 mL) were added triethylamine (0.57 mL, 4.13 mmol) and methanesulfonylchloride (0.13 mL, 1.65 mmol) drop wise at 0° C. under argon atmosphere. The reaction mixture was gradually warmed to RT for 15 min and stirred for 2 h. The reaction was monitored by TLC; after completion of the reaction, the reaction mixture was quenched with water (30 mL) and extracted with $CH_2Cl_2$ (3×30 mL). The combined organic extracts were dried over sodium sulfate, filtered and concentrated in vacuo to afford mesyl intermediate 3 (1.2 g) as yellow viscous syrup. This material was taken to the next step without further purification.

Preparation of 4:

Mesyl intermediate 3 (500 mg) was added 2.0 M N,N-dimethylamine solution in THF (5 mL) at RT; resulting reaction mixture in a sealed tube was gradually warmed to 60° C. for 10 min and stirred for 4 h. One polar product was observed by TLC. The reaction mixture was quenched with water and extracted with EtOAc (2×30 mL). The combined organic layer was washed with water and dried over anhydrous Na2SO4, filtered and concentrated under reduced pressure to afford the crude material which was purified by silica gel column chromatography [using 100-200 mesh, eluting with 30% EtOAc-hexane] to afford 300 mg of 4 as yellow thick syrup.

Preparation of UV-0136:

4 (300 mg, 0.33 mmol), 1,4-Dioxane (5 mL), 4M HCl in 1,4-Dioxane (3.0 mL), 0° C. for 15 min; gradually warmed to RT for 10 min and stirred for 24 h. After 24 h crude LCMS indicated 67% product formation. The volatiles were removed under reduced pressure to obtain 150 mg of crude material. Preparative HPLC purification [column YMC actus C-18 (250×20 mm, 5μ) (75 mg loading; $CH_3CN$: 5 mM $NH_4HCO_3$; T/B %: 0.1/90, 2/90, 10/65, 20/30, 30/10, 35/10; as mobile phase; flow rate: 15 mL/min)] afforded 39.7 mg of UV-0136 as yellow color thick syrup, purity 95.03% by HPLC [column: Zorbax SB C-18 (150×4.6 mm, 3.5 μm); RT 5.91 min; ACN: 0.5% TFA (Aq); 1.0 mL/min)], $[M+H]^+$ 441.2 by LCMS.

Example 31. Synthesis of UV-0136 (Alternative)

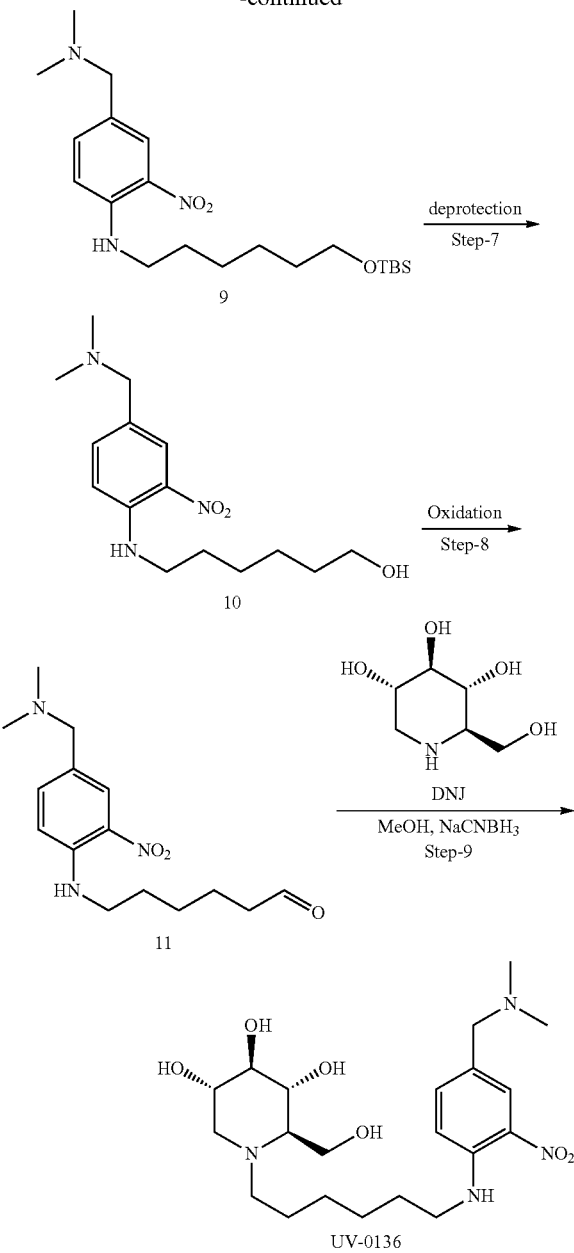

layer was washed with water and dried over anhydrous Na2SO4, filtered and concentrated under reduced pressure to afford crude material which was purified by silica gel column chromatography [100-200 mesh, eluting with 20% EtOAc-hexane] to afford 4.0 g of 4 as colorless thick syrup.

Preparation of 5:

4 (4.0 g, 11.08 mmol), EtOH (80 mL), NH2NH2.H2O (5.0 eq), RT, 16 h. Starting material was completely consumed and a polar product was observed by TLC. The volatiles were concentrated under reduced pressure and obtained residue was diluted with ice-cold water and extracted with EtOAc (2×60 mL). The combined organic layer was dried over Na2SO4, filtered and concentrated under reduced pressure to afford 2.0 g of 5 as colorless thick syrup.

Preparation of 7:

5 (2.0 g, 8.65 mmol), 1,4-dioxane (30 mL), TEA (3.0 eq), 6 (0.8 eq) at RT; resulting reaction mixture was gradually warmed to 80° C. for 10 min and stirred for 16 h. One polar product was observed by TLC. The reaction was quenched with water and extracted with EtOAc (2×50 mL). The combined organic layer was washed with water and dried over anhydrous Na2SO4, filtered and concentrated under reduced pressure to afford crude material which was purified by silica gel column chromatography [100-200 mesh, eluting with 50% EtOAc-hexane] to afford 600 mg of 7 as yellow color thick syrup.

Preparation of 8:

7 (600 mg, 1.57 mmol), DCM (15 mL), TEA (3.0 eq), MsCl (1.2 eq), 0° C. for 10 min; gradually warmed to RT for 10 min and stirred for 2 h. After 2 h, starting material was completely consumed and a non-polar product was observed by TLC. The reaction was diluted with ice-cold water and extracted with DCM (2×20 mL). The combined organic layer was dried over Na2SO4, filtered and concentrated under reduced pressure to afford 700 g of 8 (crude) as yellow color thick syrup.

Preparation of 9:

8 (700 mg) in THF (5 mL), dimethyl amine (5 mL, 2M in THF), RT; resulting reaction mixture was gradually warmed to 60° C. for 10 min and stirred for 2 h in a sealed tube. Starting material was completely consumed and a polar product was observed by TLC. Reaction was diluted with ice-cold water and extracted with EtOAc (2×20 mL). The combined organic layer was dried over Na2SO4, filtered and concentrated under reduced pressure to afford crude material which was purified by silica gel column chromatography [100-200 mesh, eluting with 80% EtOAc-hexane] to afford 400 mg of 9 as yellow color thick syrup.

Preparation of 10:

To 9 (400 mg, 0.97 mmol) in THF (10 mL) was added TBAF (1.2 eq, 1.0 M in THF) at RT and stirred. After 4 h, starting material was completely consumed and major polar product was observed by TLC. The reaction was diluted with ice-cold water and extracted with EtOAc (2×30 mL). The combined organic layer was washed with water and dried over Na2SO4 filtered and concentrated under reduced pressure to afford 300 mg of crude 10.

Preparation of 11:

Oxalylchloride (2.0 eq), THF (5.0 ml), DMSO (4.0 eq), −78° C., 10 min, 10 (300 mg, 1.02 mmol), −78° C., 20 min, TEA (4.0 eq), −78° C., 1 h, warmed to RT. After 3 h, starting material was completely consumed and a non-polar product was observed by TLC. Reaction was diluted with ice-cold water and extracted with EtOAc (2×20 mL). The combined organic layer was washed with water and dried over Preparation of 3:

1 (10 g, 86.20 mmol), toluene (200 mL) was added 2 (1.0 eq) at RT; resulting reaction mixture was gradually warmed to 100° C. for 15 min and stirred for 4 h. A non-polar product was observed by TLC. The reaction was quenched with water and extracted with EtOAc (2×100 mL). The combined organic layer was washed with water and dried over anhydrous Na2SO4, filtered and concentrated under reduced pressure to afford crude material which was purified by silica gel column chromatography [using 100-200 mesh, eluting with 50% EtOAc-hexane] to afford 10 g of 3 as white solid.

Preparation of 4:

3 (5.0 g, 20.24 mmol), DCM (100 mL), TEA (3.0 eq), TBDMS-Cl (1.2 eq), 0° C. for 20 min; gradually warmed to RT for 15 min and stirred for 4 h. A non-polar product was observed by TLC. The reaction was quenched with water and extracted with DCM (2×60 mL). The combined organic Na2SO4 filtered and concentrated under reduced pressure to afford 200 mg of 11 as yellow color thick syrup.

Preparation of UV-0136:

11 (200 mg, 0.68 mmol), MeOH (10 mL), DNJ (0.8 eq), AcOH (cat), NaCNBH3 (1.5 eq), RT. After 16 h, crude LCMS indicated 77% product formation. The volatiles were removed under reduced pressure to obtain 200 mg of crude material with purity 77.26% by HPLC [column: X SELECT CSH C18 (150×4.6 mm, 3.5 μm); RT 7.88 min; ACN: 5 mM NH4HCO3 (Aq); 1.0 mL/min)], [M+H]+ 441.1 by LCMS.

Example 32. Synthesis of UV-0139

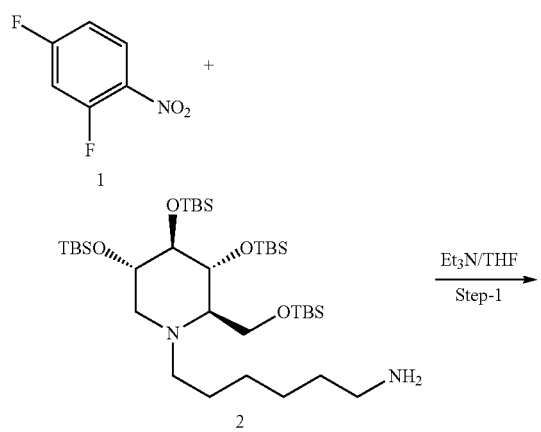

Preparation of 4:

Key fluorinated intermediate (prepared as for UV-0132, 800 mg, 0.85 mmol), DMSO (10 mL), 3 (1.5 eq), K2CO3 (2.5 eq), RT; resulting reaction mixture was gradually warmed to 60° C. for 10 min and stirred for 2 h. After 2 h a polar spot along with un reacted starting material was observed by TLC. The reaction was quenched with water and extracted with EtOAc (2×30 mL). The combined organic layer was washed with water and dried over anhydrous Na2SO4, filtered and concentrated under reduced pressure to afford crude material which was purified by silica gel column chromatography [using 100-200 mesh, eluting with 70% EtOAc-hexane to afford 400 mg of 4 as yellow color thick syrup.

Preparation of UV-0139:

4 (400 mg, 0.42 mmol), 1,4-dioxane (5 mL), 4M HCl in 1,4-dioxane (4.0 mL) at 0° C. for 10 min; gradually warmed to RT for 10 min and stirred for 48 h. Crude LCMS indicated 78% product formation. The volatiles were removed under reduced pressure to obtain 200 mg of crude material. Preparative HPLC purification [column X-select CSH C-18 (250×19 mm, 5μ) (75 mg loading; CH3CN: 5 mM NH4HCO3; T/B %: 0.1/95, 2/95, 8/65, 20/30, 25/10, 35/10; as mobile phase; flow rate: 15 mL/min)] afforded 41 mg of UV-0139 as orange red thick syrup and 30 mg after lyophilizaton, with 98.29% purity by HPLC [column: X SELECT CSH C18 (150×4.6 mm, 3.5 μm); RT 4.16 min; ACN: 5 mM NH4OAC (Aq); 1.0 mL/min)], [M+H]+ 482.2, [M+Na]+504.2 as base peak.

Example 33. Synthesis of UV-0142

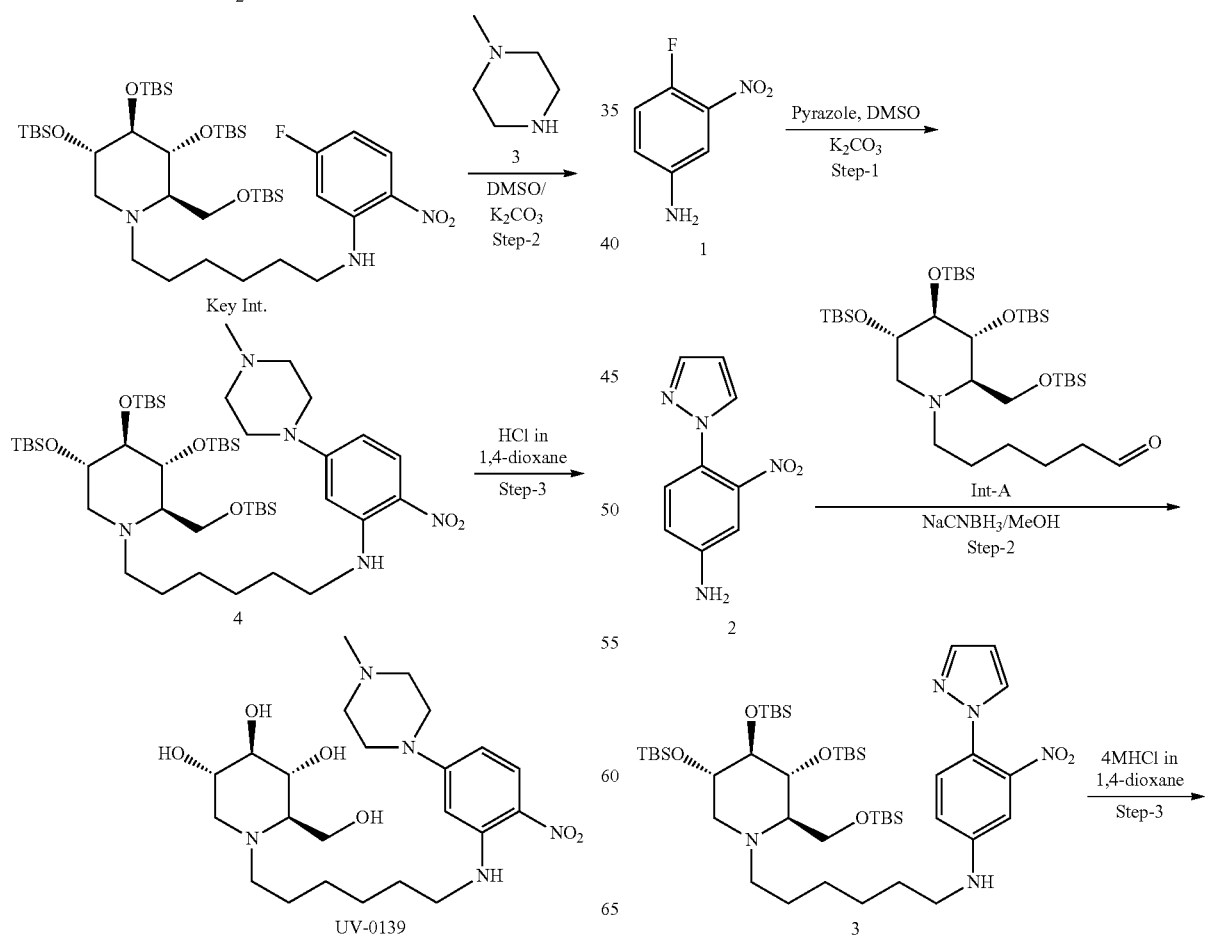

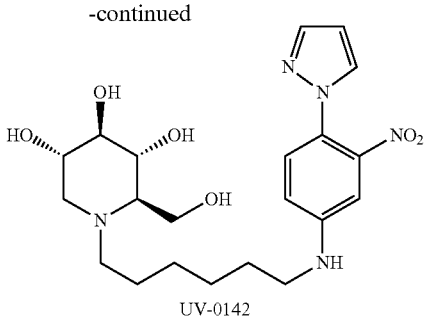

UV-0142

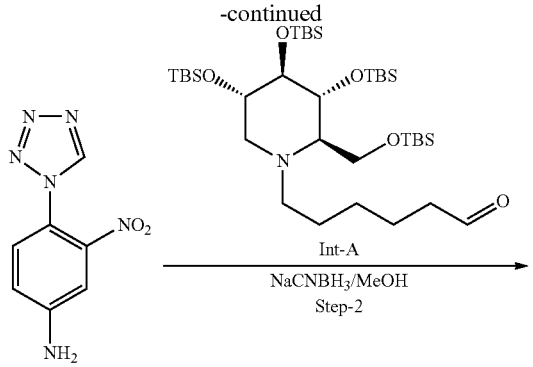

Preparation of 2:

1 (1.0 g, 6.40 mmol), DMSO (10 mL), K2CO3 (3.0 eq), pyrazole (2.0 eq) at RT, resulting reaction mixture was gradually warmed to 150° C. for 20 min and stirred for 16 h. One polar product was observed by TLC. The reaction mixture was quenched with water and extracted with EtOAc (2×30 mL). The combined organic layer was washed with water and dried over anhydrous Na2SO4, filtered and concentrated under reduced pressure to afford crude material which was purified by silica gel column chromatography [100-200 mesh, eluting with 30% EtOAc-hexane] to afford 800 mg of 2 as off-white solid.

Preparation of 3:

Int-A (see above, 750 mg, 1.04 mmol), MeOH (20 mL), 2 (0.8 eq), AcOH (Cat.), NaCNBH3 (1.5 eq), RT. After 16 h, one non-polar product was observed by TLC. The volatiles were removed under reduced pressure; residue was quenched with water and extracted with EtOAc (2×30 mL). The combined organic layer was washed with water and dried over anhydrous Na2SO4, filtered and concentrated under reduced pressure to afford crude material which was purified by silica gel column chromatography [using 100-200 mesh, eluting with 10% EtOAc-hexane] to afford 350 mg of 3 as yellow thick syrup.

Preparation of UV-0142:

3 (350 mg, 0.38 mmol) in 1,4-dioxane (5 mL), 4M HCl in 1, 4-dioxane (4.0 mL) at 0° C. for 10 min; gradually warmed to RT for 10 min and stirred for 24 h. Crude LCMS indicated 85% product formation. The volatiles were removed under reduced pressure to obtain 180 mg of crude material. Preparative HPLC purification [column X-select CSH C-18 (250×19 mm, 5µ) (75 mg loading; CH$_3$CN: 5 mM NH$_4$HCO$_3$; T/B %: 0.1/95, 2/95, 10/60, 20/30, 30/10, 35/10; as mobile phase; flow rate: 15 mL/min)] afforded 62.1 mg of UV-0142 as yellow color thick syrup with 99.71% purity by HPLC [column: X SELECT CSH C18 (150×4.6 mm, 3.5 µm); RT 7.73 min; ACN: 5 mM NH4OAC (Aq); 1.0 mL/min)], [M+H]$^+$ 450.0 by LCMS.

Example 34. Synthesis of UV-0143

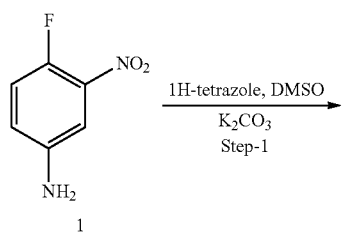

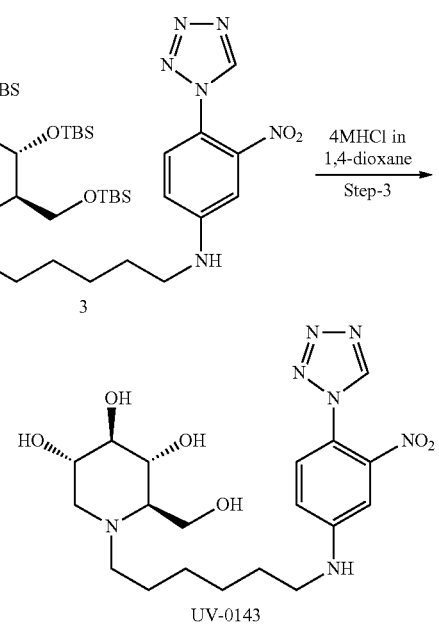

UV-0143

Preparation of 2:

1 (500 mg, 3.20 mmol), DMSO (5 mL) was added K$_2$CO$_3$ (3.0 eq), 1H-tetrazole (2.0 eq), at RT; resulting reaction mixture was gradually warmed to 150° C. for 20 min and stirred for 48 h. One polar product was along with starting material was observed by TLC. The reaction mixture was quenched with water and extracted with EtOAc (2×30 mL). The combined organic layer was washed with water and dried over anhydrous Na2SO4, filtered and concentrated under reduced pressure to afford crude material which was purified by silica gel column chromatography [using 100-200 mesh, eluting with 30% EtOAc-hexane] to afford 160 mg of 2 as off-white solid.

Preparation of 3:

Int-A (750 mg, 1.04 mmol), MeOH (20 mL), 2 (0.8 eq), AcOH (Cat.), NaCNBH3 (1.5 eq), RT. After 16 h one non-polar product was observed by TLC. The volatiles were concentrated under reduced pressure; residue was quenched with water and extracted with EtOAc (2×30 mL). The combined organic layer was washed with water and dried over anhydrous Na2SO4, filtered and concentrated under reduced pressure to afford crude material which was purified by silica gel column chromatography [using 100-200 mesh, eluting with 10% EtOAc-hexane] to afford 250 mg of 3 as yellow thick syrup.

Preparation of UV-0143:

3 (350 mg, 0.38 mmol), 1,4-Dioxane (5 mL), 4M HCl in 1,4-Dioxane (4.0 mL), 0° C. for 10 min; gradually warmed to RT for 10 min and stirred for 24 h. Crude LCMS indicated 83% product formation. The volatiles were removed under reduced pressure to obtain 162 mg of crude material. Preparative HPLC purification [column X-select CSH C-18 (250×19 mm, 5μ) (75 mg loading; CH$_3$CN: 5 mM NH$_4$HCO$_3$; T/B %: 0.1/95, 2/95, 10/60, 20/30, 30/10, 35/10; as mobile phase; flow rate: 15 mL/min)] afforded 23.8 mg of UV-0143 as yellow color thick syrup with 98.79% purity by HPLC [column: X SELECT CSH C18 (150×4.6 mm, 3.5 μm); RT 7.17 min; ACN: 5 mM NH4OAC (Aq); 1.0 mL/min)], [M+H]$^+$ 452.1 by LCMS.

Example 35. Synthesis of UV-0153

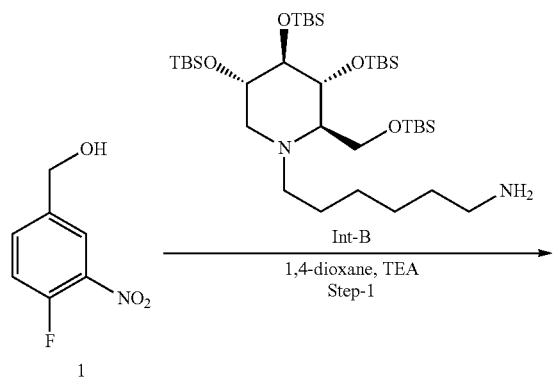

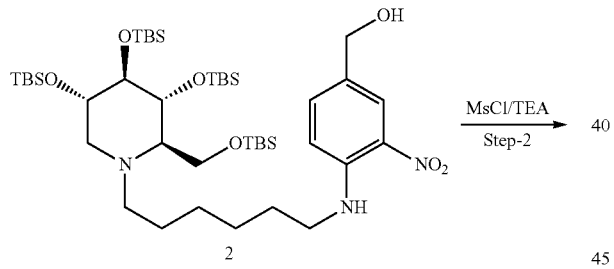

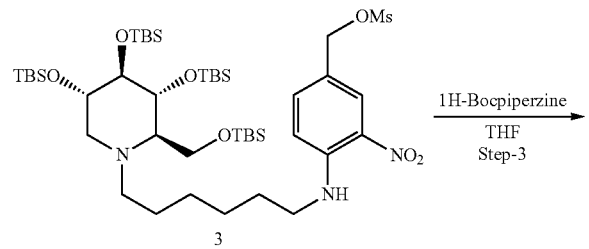

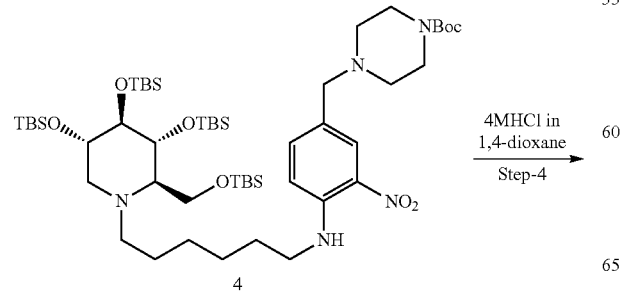

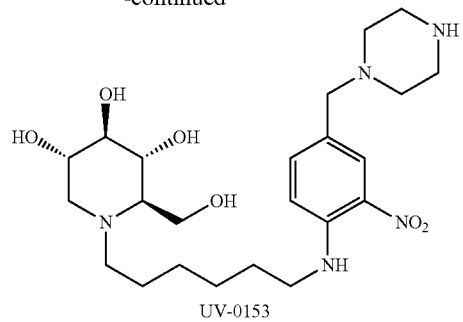

UV-0153

Preparation of 4:

Mesyl intermediate 3 (650 mg), Boc-piperazine (excess equivalents), THF (10 mL), RT; resulting reaction mixture was gradually warmed to 60° C. for 10 min and stirred for 6 h. One polar product was observed by TLC. The reaction mixture was quenched with water and extracted with EtOAc (2×30 mL). The combined organic layer was washed with water and dried over anhydrous Na2SO4, filtered and concentrated under reduced pressure to afford crude material which was purified by silica gel column chromatography [100-200 mesh, eluting with 30% EtOAc-hexane] to afford 350 mg of 4 as yellow thick syrup.

Preparation of UV-0153:

4 (350 mg, 0.33 mmol), 1,4-dioxane (5 mL), 4M HCl in 1,4-dioxane (4.0 mL), 0° C. for 10 min; gradually warmed to RT for 10 min and stirred for 24 h. Crude LCMS indicated 73% product formation. The volatiles were removed under reduced pressure to obtain 200 mg of crude material. Preparative HPLC purification [column X-select CSH C-18 (250×19 mm, 5μ) (75 mg loading; CH$_3$CN: 5 mM NH$_4$HCO$_3$; T/B %: 0.1/95, 2/95, 10/65, 20/35, 30/10, 35/10; as mobile phase; flow rate: 15 mL/min)] afforded ~35 mg of UV-0153 as yellow color thick syrup, 99.26% purity by HPLC [column: Zorbax SB C-18 (150×4.6 mm, 3.5 μm); RT 5.39 min; ACN: 0.5% TFA (Aq); 1.0 mL/min)], [M+H]$^+$ 482.2 by LCMS.

Example 36. Synthesis of UV-0154

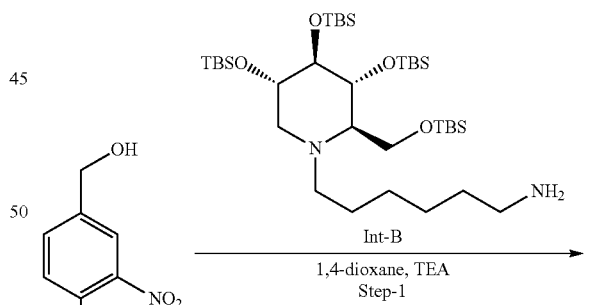

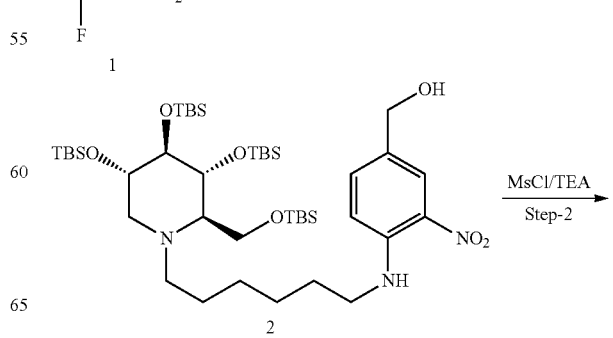

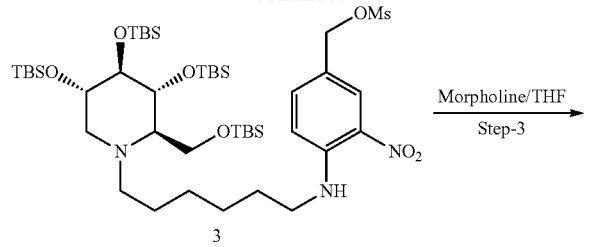
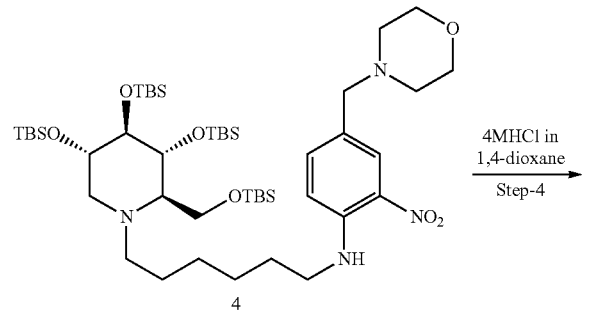

Preparation of 4:

Mesyl intermediate 3 (650 mg) in THF was added morpholine (excess eq, 10 mL) at RT; resulting reaction mixture was gradually warmed to 60° C. for 10 min and stirred for 6 h. One polar product was observed by TLC. The reaction was quenched with water and extracted with EtOAc (2×30 mL). The combined organic layer was washed with water and dried over anhydrous Na2SO4, filtered and concentrated under reduced pressure to afford crude material which was purified by silica gel column chromatography [using 100-200 mesh, eluting with 30% EtOAc-hexane] to afford 250 mg of 4 as yellow thick syrup.

Preparation of UV-0154:

4 (250 mg, 0.26 mmol) in 1,4-dioxane (5 mL) was added 4M HCl in 1, 4-dioxane (4.0 mL) at 0° C. for 10 min; gradually warmed to RT for 10 min and stirred. After 24 h, crude LCMS indicated 78% product formation. The volatiles were removed under reduced pressure to obtain 200 mg of crude material. Preparative HPLC purification [column X-select CSH C-18 (250×19 mm, 5µ) (75 mg loading; CH3CN: 5 mM NH4HCO3; T/B %: 0.1/95, 2/95, 10/65, 20/35, 30/10, 35/10; as mobile phase; flow rate: 15 mL/min)] afforded ~35 mg of UV-0154 as yellow color thick syrup, purity 99.58% by HPLC (column: Zorbax SB C-18 (150×4.6 mm, 3.5 µm); RT 5.66 min; ACN: 0.5% TFA (Aq); 1.0 mL/min)], [M+H]+ 483.1 by LCMS.

Example 37. Synthesis of UV-0157

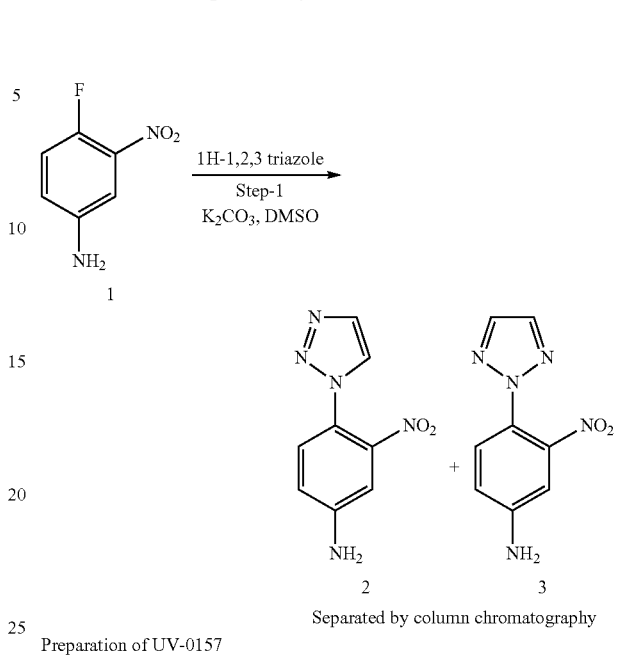

Preparation of UV-0157

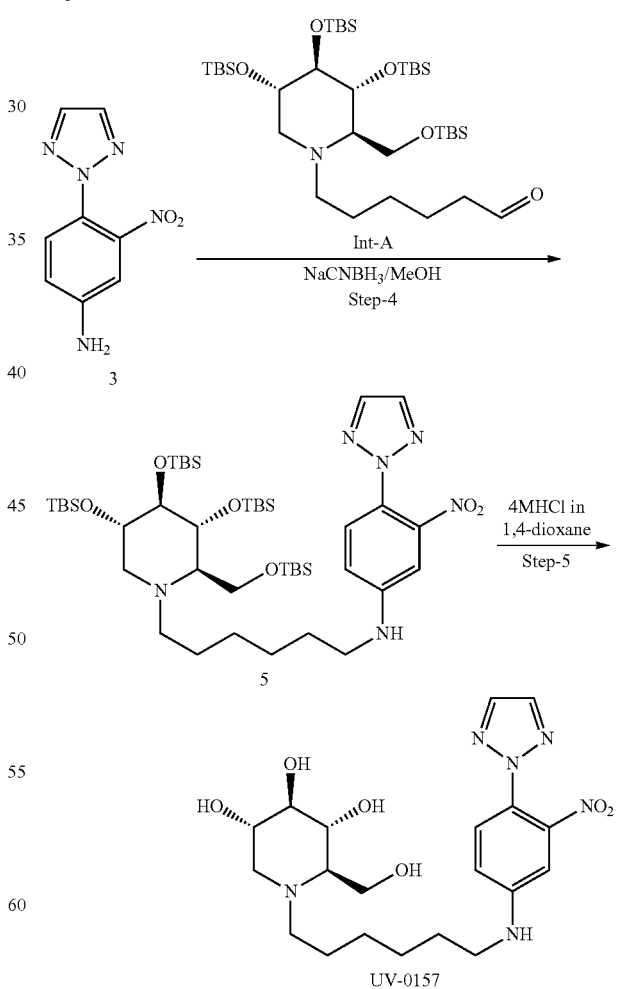

Preparation of 2 and 3:

1 (1.0 g, 6.40 mmol), DMSO (10 mL) was added K2CO3 (3.0 eq), 1H-1,2,3 triazole (1.2 eq) at RT; resulting reaction mixture was gradually warmed to 150° C. for 20 min and stirred for 24 h. Two polar products were observed by TLC. The reaction was quenched with water and extracted with EtOAc (2×40 mL). The combined organic layer was washed with water and dried over anhydrous Na2SO4, filtered and concentrated under reduced pressure to afford the crude material. Two polar products were isolated by silica gel column chromatography [100-200 mesh, eluting with 20% and 50% EtOAc-hexane] to afford 300 mg and 320 mg of respective isomers as off-white solids.

Preparation of 5:

Int-A (see above, 800 mg, 1.11 mmol), MeOH (20 mL), 2 (0.8 eq less polar isomer), AcOH (Cat.), NaCNBH3 (1.5 eq), RT. After 16 h, one non-polar product was observed by TLC. The volatiles were concentrated under reduced pressure; residue was quenched with water and extracted with EtOAc (2×30 mL). The combined organic layer was washed with water and dried over anhydrous Na2SO4, filtered and concentrated under reduced pressure to afford crude material which was purified by silica gel column chromatography [using 100-200 mesh, eluting with 10% EtOAc-hexane] to afford 300 mg of 5 as yellow thick syrup.

Preparation of UV-0157:

5 (300 mg, 0.32 mmol) in 1,4-dioxane (5 mL) was added 4M HCl in 1,4-dioxane (3.0 mL), 0° C. for 10 min; gradually warmed to RT for 10 min and stirred for 24 h. Crude LCMS indicated 80% product formation. The volatiles were removed under reduced pressure to obtain 170 mg of crude material. Preparative HPLC purification [column X-select CSH C-18 (250×19 mm, 5µ) (100 mg loading; CH3CN: 5 mM NH4HCO3; T/B %: 0.1/95, 2/95, 10/70, 25/30, 30/10, 35/10; as mobile phase; flow rate: 15 mL/min)] afforded 69.9 mg of UV-0157 as yellow color thick syrup with 99.57% purity by HPLC [column: X SELECT CSH C18 (150×4.6 mm, 3.5µ); RT 7.77 min; ACN: 5 mM NH4OAC (Aq); 1.0 mL/min)], [M+H]+ 451.1 by LCMS.

Example 38. Synthesis of UV-0158

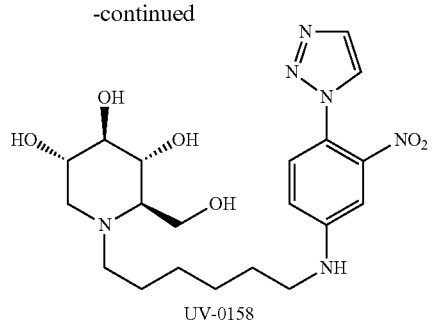

UV-0158

Preparation of 4:

Int-A (see above, 800 mg, 1.11 mmol), MeOH (20 mL), 1 (0.8 eq of the more polar isomer purified from isomer mixture as described for UV-0157), AcOH (Cat.), NaCNBH3 (1.5 eq), RT. After 16 h, one non-polar product was observed by TLC. The volatiles were concentrated under reduced pressure; residue was quenched with water and extracted with EtOAc (2×30 mL). The combined organic layer was washed with water and dried over anhydrous Na2SO4, filtered and concentrated under reduced pressure to afford crude material which was purified by silica gel column chromatography [using 100-200 mesh, eluting with 10% EtOAc-hexane] to afford 200 mg of 2 as yellow thick syrup.

Preparation of UV-0158:

2 (200 mg, 0.21 mmol, more polar product of triazole reaction) in 1,4-dioxane (5 mL) was added 4M HCl in 1,4-dioxane (3.0 mL) at 0° C. for 10 min; gradually warmed to RT for 10 min and stirred for 24 h. Crude LCMS indicated 83% product formation. The volatiles were removed under reduced pressure to obtain 120 mg of crude material. Preparative HPLC purification [column X-select CSH C-18 (250×19 mm, 5µ) (75 mg loading; CH3CN: 5 mM NH4HCO3; T/B %: 0.1/95, 2/95, 10/70, 20/35, 25/10, 35/10; as mobile phase; flow rate: 15 mL/min)] afforded 22.2 mg of UV-0158 as yellow solid, 98.15% purity by HPLC [column: X SELECT CSH C18 (150×4.6 mm, 3.5µ); RT 7.09 min; ACN: 5 mM NH4OAC (Aq); 1.0 mL/min)], [M+H]+ 451.2 by LCMS.

Example 39. Synthesis of UV-0160

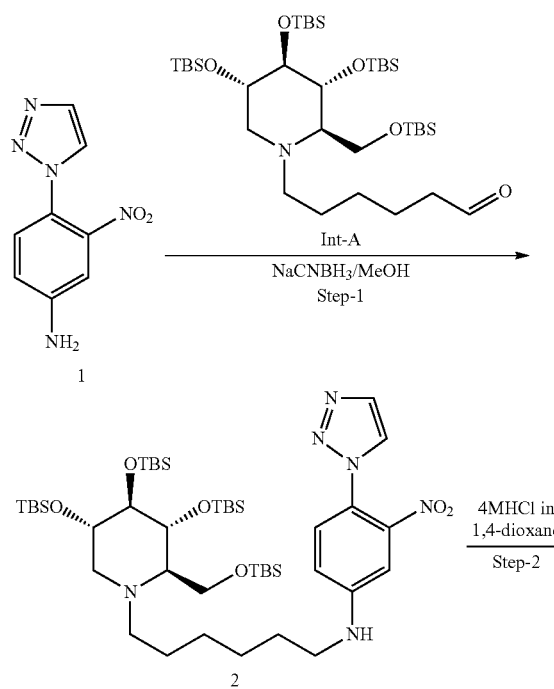

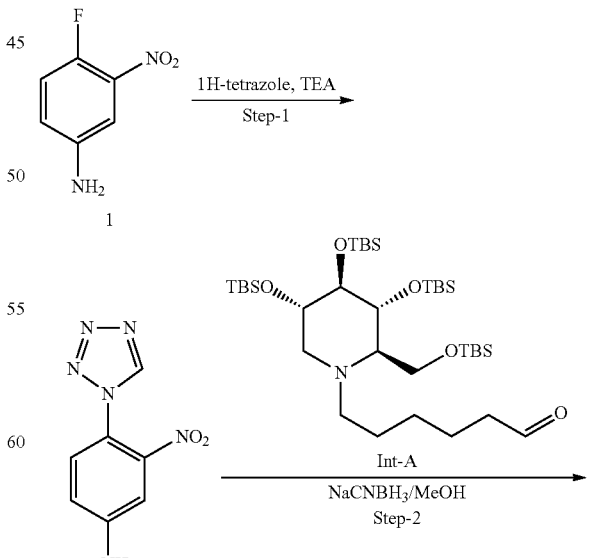

103

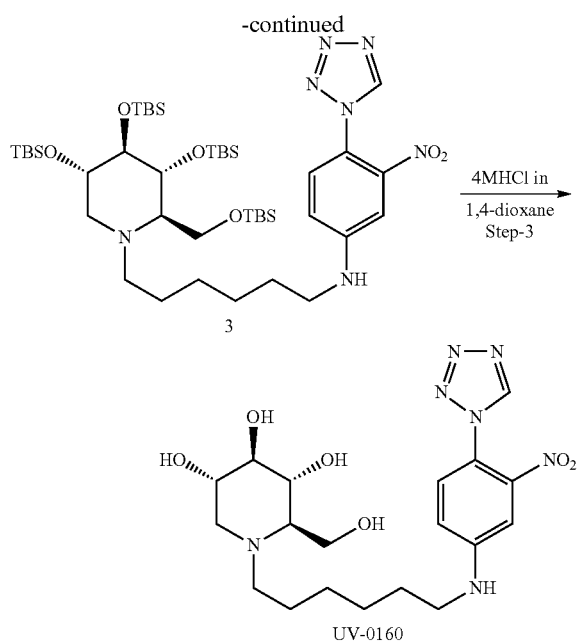

UV-0160

Preparation of 2:

1 (500 mg, 2.56 mmol), TEA (10 mL), 1H-tetrazole (10 eq), sealed tube, RT; reaction mixture was gradually warmed to 120° C. for 20 min and stirred for 48 h. Two polar products along with small amount of starting material was observed by TLC. The reaction was quenched with water and extracted with EtOAc (2×30 mL). The combined organic layer was washed with water and dried over anhydrous Na2SO4, filtered and concentrated under reduced pressure to afford crude material which was purified by silica gel column chromatography [100-200 mesh, eluting with 50-70% EtOAc-hexane] to afford 180 mg of 2 as off-white solid.

Preparation of 3:

2 (180 mg, 0.87 mmol), MeOH (20 mL), Int-A (1.0 eq), AcOH (Cat.), NaCNBH3 (1.5 eq), RT. After 16 h, a nonpolar product along with unreacted amine (2) was observed by TLC. The volatiles were concentrated under reduced pressure; residue was quenched with water and extracted with EtOAc (2×50 mL). The combined organic layer was washed with water and dried over anhydrous Na2SO4, filtered and concentrated under reduced pressure to afford crude material which was purified by silica gel column chromatography [using 100-200 mesh, eluting with 20% EtOAc-hexane] to afford 200 mg of 3.

Preparation of UV-0160:

3 (200 mg, 0.22 mmol) in 1,4-dioxane (5 mL) was added 4M HCl in 1,4-dioxane (2.0 mL) at 0° C. for 10 min; gradually warmed to RT for 10 min and stirred for 24 h. Crude LCMS indicated 85% desired product. The volatiles were removed under reduced pressure to obtain 120 mg of crude material. Preparative HPLC purification [column X-select CSH C-18 (250×19 mm, 5μ) (50 mg loading; CH3CN: 5 mM NH4HCO3; T/B %: 0.1/95, 2/95, 10/70, 20/35, 28/10, 35/10; as mobile phase; flow rate: 15 mL/min)] afforded ~20 mg of UV-0160 as yellow color thick syrup, purity by HPLC 97.77% [column: X SELECT CSH C18 (150×4.6 mm, 3.5 μm); RT 7.96 min; ACN: 5 mM NH4OAC (Aq); 1.0 mL/min)], [M+H]+ 452.1 by LCMS.

104

Example 40. Synthesis of UV-0162

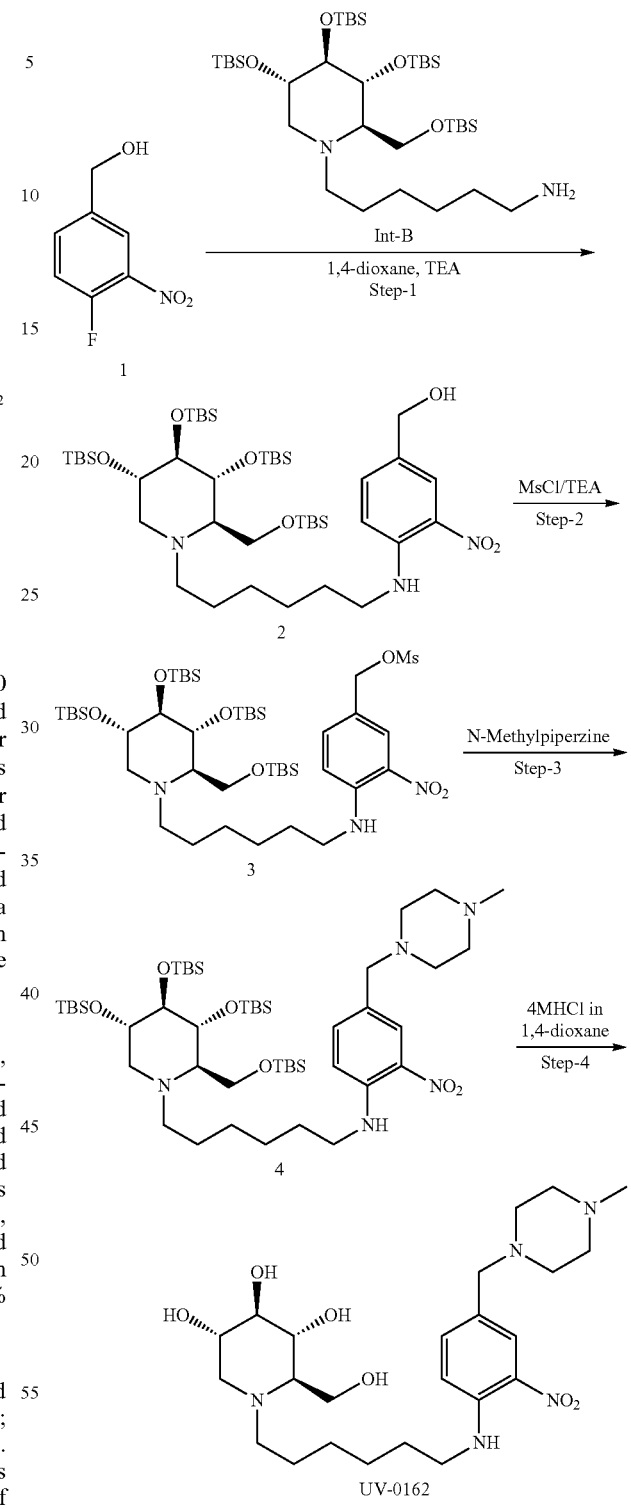

Preparation of 4:

Mesyl intermediate 3 (660 mg), THF (4 mL), N-methyl piperizine (2 mL), in a sealed tube, RT; resulting reaction mixture was gradually warmed to 60° C. for 10 min and stirred for 4 h. A polar product was observed by TLC. The reaction was quenched with water and extracted with EtOAc (2×50 mL). The combined organic layer was washed with water and dried over anhydrous Na2SO4, filtered and concentrated under reduced pressure to afford crude material which was purified by silica gel column chromatography [100-200 mesh, eluting with 30% EtOAc-hexane] to afford 400 mg of 4 as yellow thick syrup.

Preparation of UV-0162:

4 (400 mg, 0.42 mmol), 1,4-dioxane (10 mL), 4M HCl in 1,4-dioxane (2.0 mL), 0° C. for 10 min; gradually warmed to RT for 10 min and stirred for 16 h. Crude LCMS indicated 70% product formation. The volatiles were removed under reduced pressure to obtain 300 mg of crude material. Preparative HPLC purification [column X-select CSH C-18 (250×19 mm, 5µ) (100 mg loading; CH₃CN: 5 mM NH₄HCO₃; T/B %: 0.1/90, 2/90, 8/70, 20/40, 30/10, 35/10; as mobile phase; flow rate: 15 mL/min)] afforded 60 mg of UV-0162, purity 99.42% by HPLC (column: ATLANTIS T3 (150×4.6 mm, 3.0 µm); RT 7.20 min; ACN: 5 mM NH4OAC (Aq); 1.0 mL/min)], [M+H]⁺ 496.2 by LCMS.

Example 41. Synthesis of UV-0163

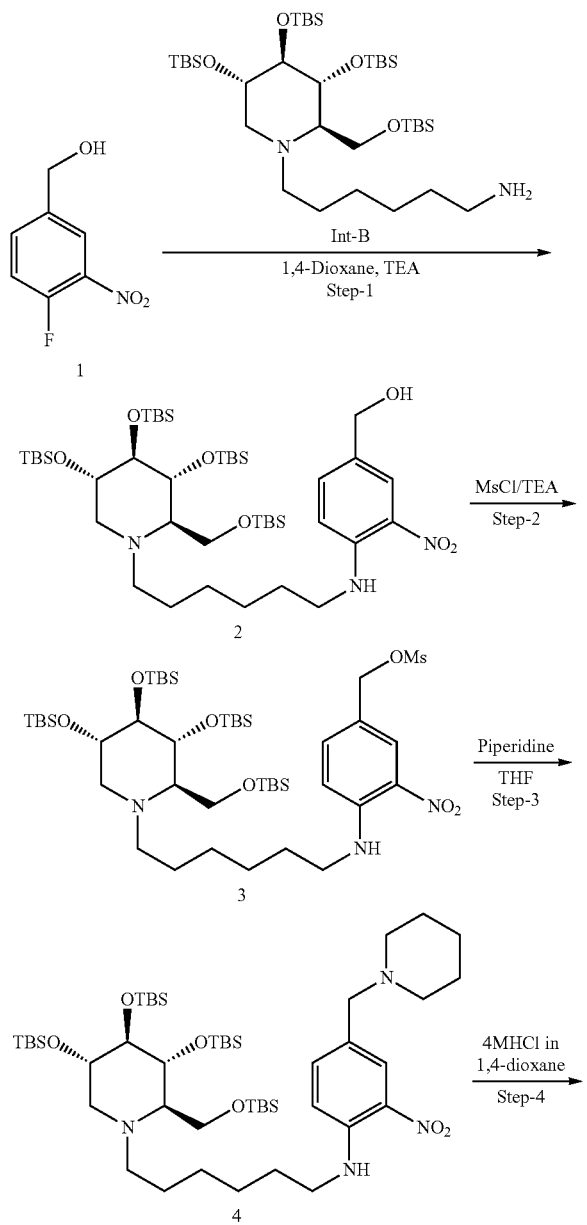

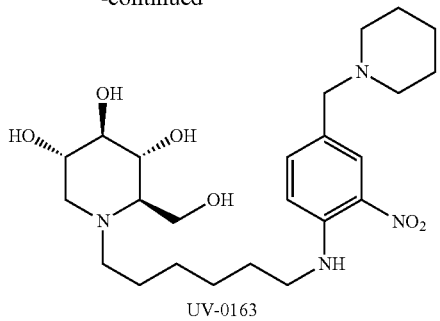

Preparation of 4:

Mesyl intermediate 3 (600 mg) in THF (20 mL) was added piperidine (2 mL) at RT; resulting reaction mixture was gradually warmed to 60° C. for 10 min and stirred for 3 h. After 3 h, starting material was completely consumed and a new polar product was observed by TLC. Reaction was diluted with ice-cold water and extracted with EtOAc (2×20 mL). The combined organic layer was dried over Na₂SO₄ filtered and concentrated under reduced pressure to afford crude. The obtained crude material was purified by silica gel (100-200) flash column chromatography by eluting with 10% EtOAc-hexane to afford 300 mg of 4 as yellow color thick syrup.

Preparation of UV-0163:

4 (300 mg, 0.32 mmol), 1,4-Dioxane (5 mL), 4M HCl in 1,4-dioxane (2.0 mL), 0° C. for 10 min; gradually warmed to RT for 10 min and stirred for 16 h. Crude LCMS indicated 87% product formation. The volatiles were removed under reduced pressure to obtain 250 mg of crude material. Preparative HPLC purification [column YMC actus C-18 (250× 20 mm, 5µ) (75 mg loading; CH₃CN: 5 mM NH₄HCO₃; T/B %: 0.1/95, 2/95, 8/70, 25/35, 30/10, 35/10; as mobile phase; flow rate: 15 mL/min)] afforded 35 mg of UV-0163, 99.18% purity by HPLC [column: X SELECT CSH C18 (150×4.6 mm, 3.5 µm); RT 7.97 min; ACN: 5 mM NH4OAC (Aq); 1.0 mL/min)], [M+H]⁺ 481.1 by LCMS.

Example 42. Synthesis of UV-0165

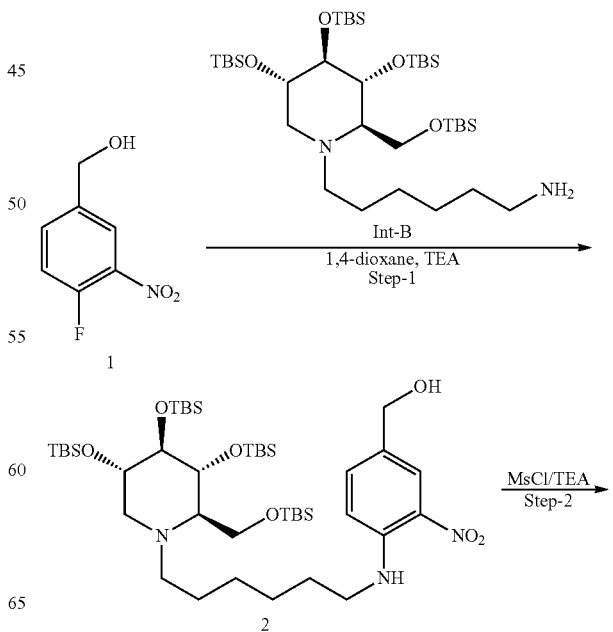

Example 43. Synthesis of UV-0168

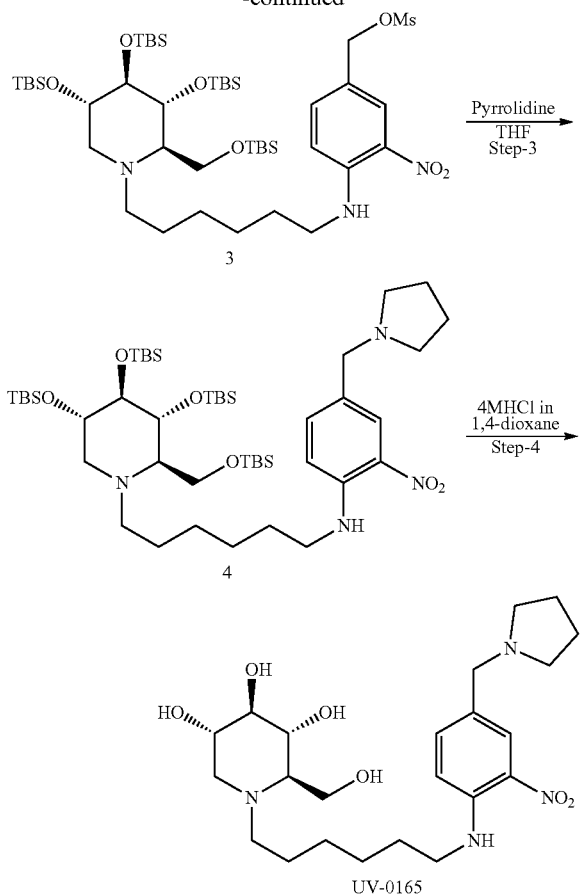

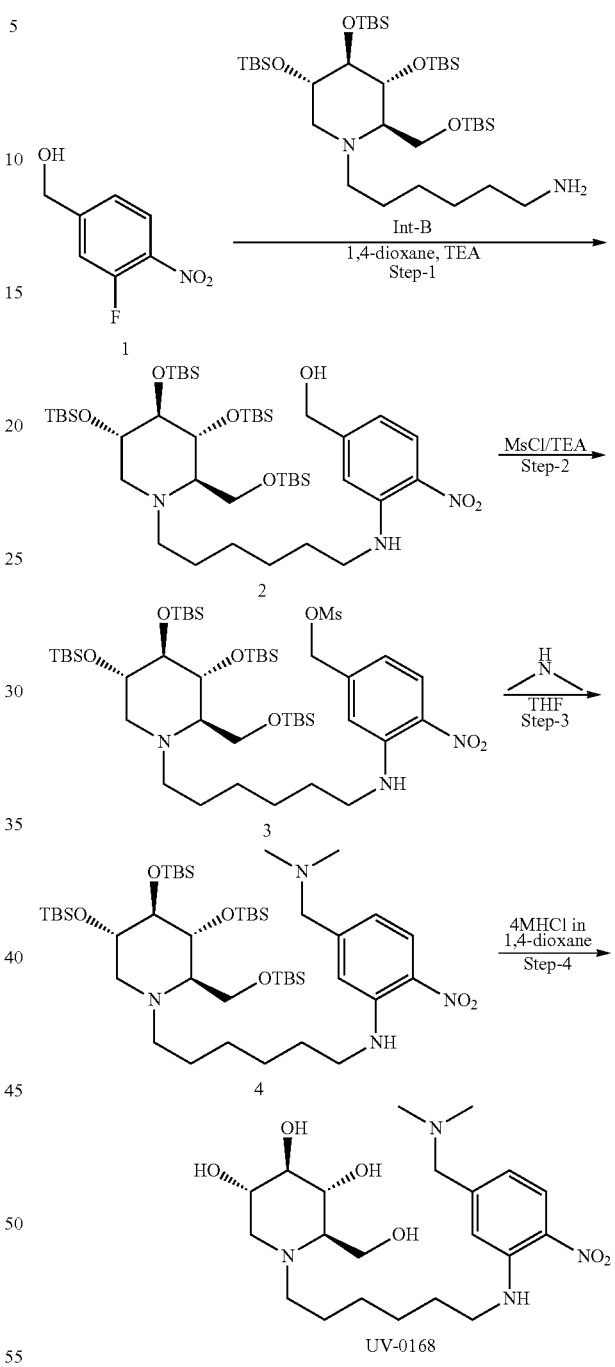

Preparation of 4:

Mesyl intermediate 3 (600 mg) in THF (20 mL) was added pyrrolidine (2 mL) at RT; resulting reaction mixture was gradually warmed to 60° C. for 10 min and stirred for 3 h. Starting material was completely consumed and a new polar product was observed by TLC. Reaction was diluted with ice-cold water and extracted with EtOAc (2×20 mL). The combined organic layer was dried over Na2SO4 filtered and concentrated under reduced pressure to afford crude. The obtained crude material was purified by silica gel (100-200) flash column chromatography by eluting with 10% EtOAc-hexane to afford 320 mg of 4 as yellow color thick syrup.

Preparation of UV-0165:

4 (320 mg, 0.34 mmol) in 1, 4-dioxane (5 mL) was added 4M HCl in 1, 4-dioxane (2.0 mL) at 0° C. for 10 min; gradually warmed to RT for 10 min and stirred for 16 h. Crude LCMS indicated 78% desired mass. The volatiles were removed under reduced pressure to obtain 300 mg of crude material. Preparative HPLC purification [column YMC actus C-18 (250×20 mm, 5μ) (75 mg loading; CH$_3$CN: 5 mM NH$_4$HCO$_3$; T/B %: 0.1/95, 2/95, 8/70, 25/35, 30/10, 35/10; as mobile phase; flow rate: 15 mL/min)] afforded 35 mg of UV-0165 with purity 98.22% by HPLC 98.22% [column: X SELECT CSH C18 (150×4.6 mm, 3.5 μm); RT 7.25 min; ACN: 5 mM NH4OAC (aq); 1.0 mL/min)]; [M+H]$^+$ 467.1 by LCMS.

Preparation of 2:

Int-B (see above, 1.2 g, 1.66 mmol) in 1,4-dioxane (20 mL) was added TEA (10 mL), 1 (0.8 eq) at RT; resulting reaction mixture was gradually warmed to 80° C. for 10 min and stirred for 16 h. After 16 h, a non-polar product was observed by TLC. The reaction was quenched with water and extracted with EtOAc (2×50 mL). The combined organic layer was washed with water and dried over anhydrous Na2SO4, filtered and concentrated under reduced pressure to afford crude material which was purified by silica gel column chromatography [using 100-200 mesh, eluting with 20% EtOAc-hexane] to afford 600 mg of 2 as yellow color thick syrup.

Preparation of 3:

2 (600 mg, 0.68 mmol) in DCM (15 mL) was added TEA (3.0 eq), MsCl (1.2 eq) at 0° C. for 10 min; gradually warmed to RT for 10 min and stirred for 2 h. After 2 h, starting material was completely consumed and a new non-polar product was observed by TLC. Reaction was diluted with ice-cold water and extracted with DCM (2×20 mL). The combined organic layer was dried over Na2SO4 filtered and concentrated under reduced pressure to afford 700 mg of 3 as yellow color thick syrup which was used without purification in the next reaction.

Preparation of 4:

3 (700 mg, crude) in THF (5 mL) was added N,N-dimethylamine (3 mL, 1M in THF) at RT; resulting reaction mixture was gradually warmed in sealed tube to 60° C. for 10 min and stirred for 3 h. Starting material was completely consumed and one new polar product was observed by TLC. Reaction was diluted with ice-cold water and extracted with EtOAc (2×20 mL). The combined organic layer was dried over Na2SO4 filtered and concentrated under reduced pressure to afford the crude. The obtained crude material was purified by silica gel (100-200) flash column chromatography by eluting with 20% EtOAc-hexane to afford 400 mg of 4 as yellow color thick syrup.

Preparation of UV-0168:

4 (400 mg, 0.42 mmol) in 1,4-dioxane (6 mL) was added 4M HCl in 1,4-dioxane (4.0 mL) at 0° C. for 10 min; gradually warmed to RT for 10 min and stirred for 16 h. LCMS indicated 81% desired mass. The volatiles were removed under reduced pressure to obtain 300 mg of crude material. Preparative HPLC purification [X-select CSH C-18 (250×19 mm, 5µ) (75 mg loading; CH$_3$CN: 5 mM NH$_4$HCO$_3$; T/B %: 0.1/95, 2/95, 8/75, 22/35, 28/10, 35/10; as mobile phase; flow rate: 15 mL/min)] yielded 50 mg of UV-0168, 97.930% purity by HPLC [column: X SELECT CSH C18 (150×4.6 mm, 3.5 µm); RT 8.17 min; ACN: 5 mM NH4OAC (Aq); 1.0 mL/min)], [M+H]$^+$ 441.1, 463.1 [M+Na]$^+$ base peak.

Example 44. Synthesis of UV-0246

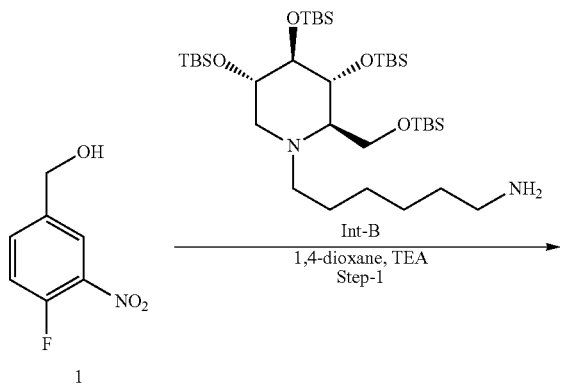

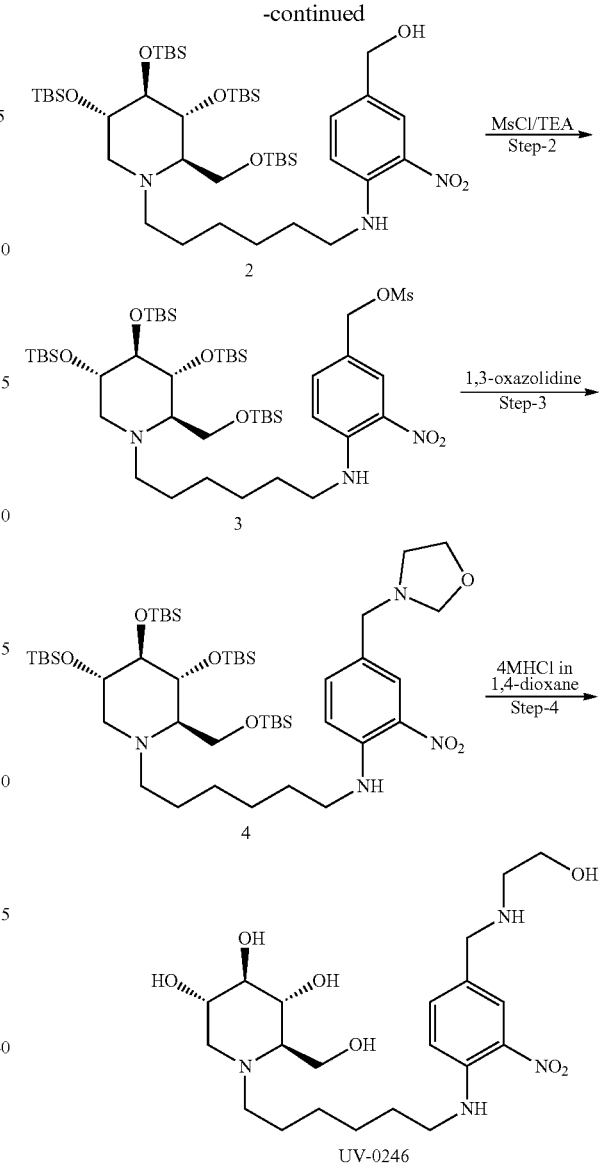

Preparation of 4:

Mesyl intermediate 3 (660 mg) in THF (4 ml) 1,3-oxazolidine.HCl (1.2 eq), DIPEA (2 ml) in a sealed tube at RT; resulting reaction mixture was gradually warmed to 60° C. for 10 min and stirred for 4 h. After 4 h, one polar spot was observed by TLC along with other non-polar impurities. The reaction mass was quenched with water and extracted with EtOAc (2×50 mL). The combined organic layer was washed with water and dried over anhydrous Na2SO4, filtered and concentrated under reduced pressure to afford crude material which was purified by silica gel column chromatography [using 100-200 mesh, eluting with 30% EtOAc-hexane] to afford 150 mg of 4 as yellow thick syrup.

Preparation of UV-0246:

4 (150 mg, 0.16 mmol), 1,4-dioxane (5 mL), 4M HCl in 1,4-dioxane (2.0 mL), 0° C. for 10 min; gradually warmed to RT for 10 min and stirred for 16 h. After 16 h, crude LCMS indicated 80% product formation. The volatiles were removed under reduced pressure to obtain 125 mg of crude material. Preparative HPLC purification [column X-select CSH C-18 (250×19 mm, 5µ) (100 mg loading; CH$_3$CN: 5 mM NH4HCO3; T/B %: 0.1/95, 2/95, 10/70, 20/35, 25/10, 35/10; as mobile phase; flow rate: 15 mL/min)] afforded ~20 mg of UV-0246, purity 98.17% by HPLC, [M+H]+ 457.1 by LCMS.

Example 45. Synthesis of UV-0178

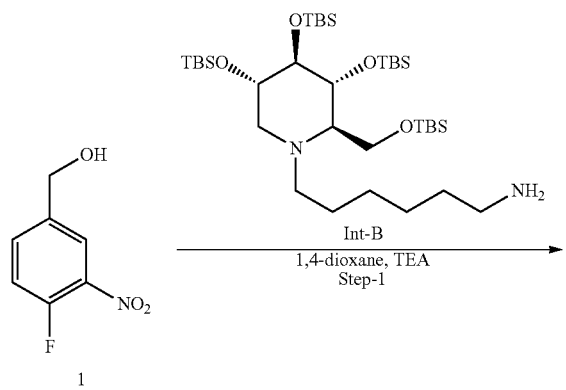
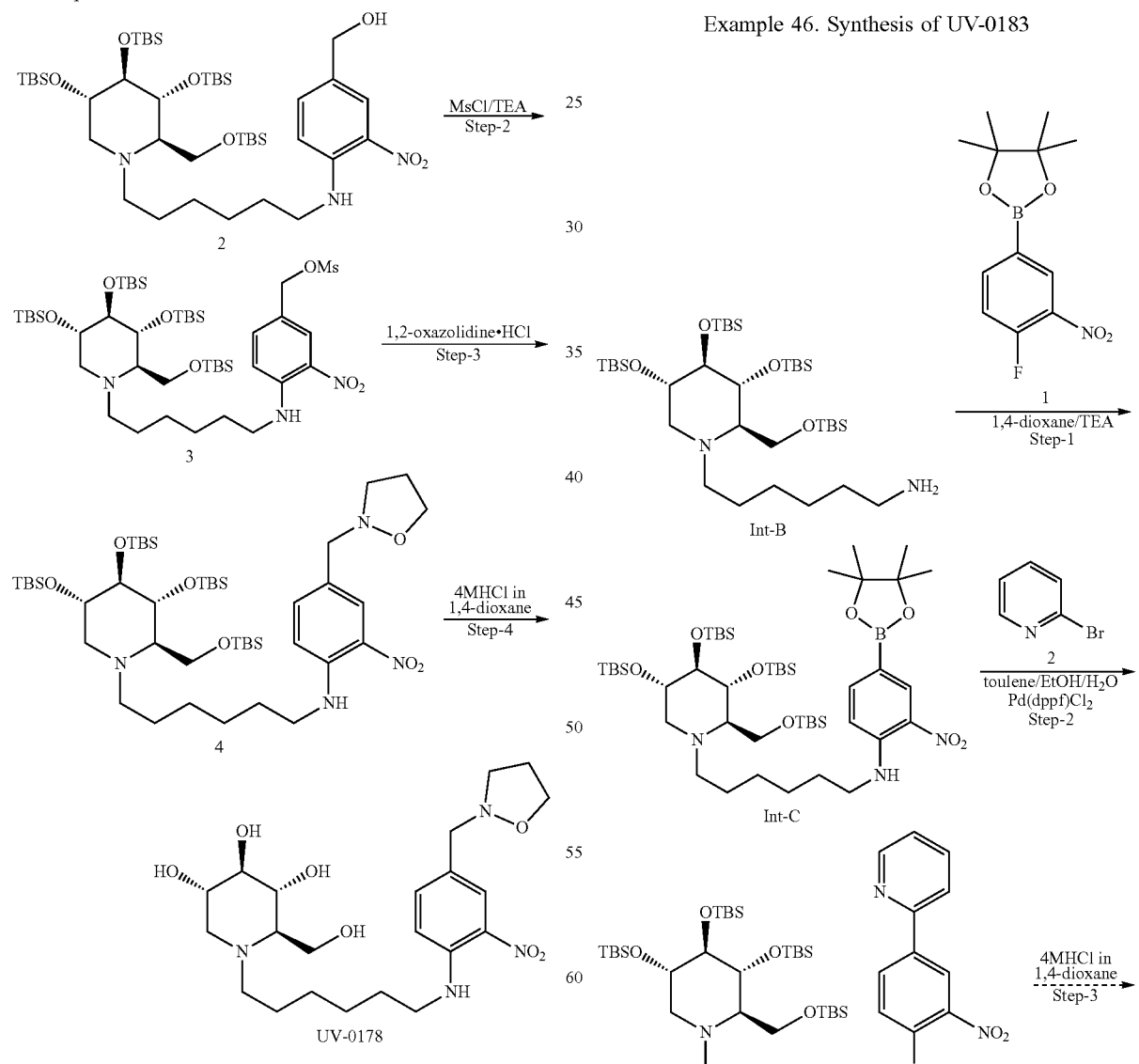

Preparation of 4:
3 (660 mg crude), THF (4 ml), 1,2-oxazolidine.HCl (1.2 eq), DIPEA (2 ml) in a sealed tube, RT; resulting reaction mixture was gradually warmed to 60° C. for 10 min and stirred for 4 h. A polar product spot was observed by TLC. The reaction was quenched with water and extracted with EtOAc (2×50 mL). The combined organic layer was washed with water and dried over anhydrous Na2SO4, filtered and concentrated under reduced pressure to afford the crude.

The obtained crude material was purified by silica gel column chromatography [using 100-200 mesh, eluting with 30% EtOAc-hexane] to afford 250 mg of 4 as yellow thick syrup.

Preparation of UV-0178:
4 (250 mg, 0.26 mmol) in 1,4-dioxane (10 mL), 4M HCl in 1,4-dioxane (2.0 mL), 0° C. for 10 min; gradually warmed to RT for 10 min and stirred. After 16 h, crude LCMS indicated 88% product formation. The volatiles were removed under reduced pressure to obtain 200 mg of crude material. Preparative HPLC purification [column X-select CSH C-18 (250×19 mm, 5µ) (100 mg loading; CH3CN: 5 mM NH4HCO3; T/B %: 0.1/90, 2/90, 8/70, 20/30, 30/10, 35/10; as mobile phase; flow rate: 15 mL/min)] afforded 20 mg of UV-0178, purity 99.45% by HPLC [column: ATLANTIS T3 (150×4.6 mm, 3.0 µm); RT 7.81 min; ACN: 5 mM NH4OAC (Aq); 1.0 mL/min)], [M+H]+ 469.1 by LCMS.

Example 46. Synthesis of UV-0183

-continued

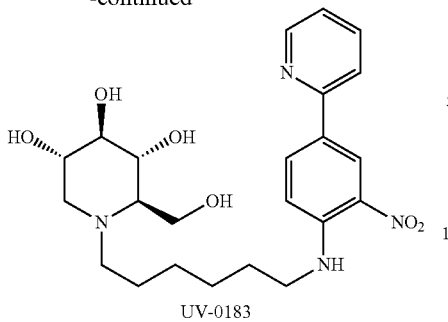

UV-0183

Preparation of 3:

Int-C (see above, 800 mg, crude), EtOH:toluene:water (1:1:1, 20 mL), 2 (1.5 eq), RT; reaction mixture was purged under argon at RT for 30 min; Na2CO3 (3.0 eq), Pd(dppf)2Cl2 (0.1 eq), RT and again purged again under argon for 30 min, the reaction mixture was heated to 60° C. and stirred for 4 h. One major polar product was observed by TLC. The reaction was quenched with water and extracted with EtOAc (2×30 mL). The combined organic layer was washed with water and dried over anhydrous Na2SO4, filtered and concentrated under reduced pressure to afford crude material which was purified by silica gel column chromatography [100-200 mesh, eluting with 10% EtOAc-hexane] to afford 500 mg of 3 as yellow color thick syrup.

Preparation of UV-0183:

3 (500 mg, 0.54 mmol), 1,4-dioxane (8 mL), 4M HCl in 1,4-dioxane (5.0 mL), 0° C. for 10 min; gradually warmed to RT for 10 min and stirred for 16 h. LCMS indicated 80% desired mass. The volatiles were removed under reduced pressure to obtain 350 mg of the crude material. Preparative HPLC purification [column: X-select CSH C-18 (250×19 mm, 5µ) (100 mg loading; CH3CN: 5 mM NH4HCO3; T/B %: 0.1/95, 2/95, 8/75, 22/35, 28/10, 35/10; as mobile phase; flow rate: 15 mL/min)] afforded 50 mg of UV-0183 with 95.765% purity by HPLC (column: X SELECT CSH C18 (150×4.6 mm, 3.5 µm); RT 8.60 min; ACN: 5 mM NH4OAC (Aq); 1.0 mL/min)], [M+H]+ 461.1, [M+Na]+483.1 base peak.

Example 47. Synthesis of UV-0241

-continued

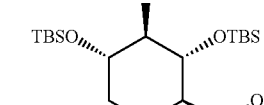

HCl in 1,4-dioxane
1,4-dioxane
Step-2

2

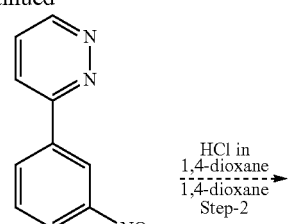

UV-0241

Preparation of 2:

Common Int-C (800 mg, 0.82 mmol), EtOH:toluene:water (1:1:1, 20 mL), 1 (3-bromopyridazine, 1.0 eq), and purged under argon at RT for 30 min; Na2CO3 (3.0 eq), Pd(dppf)2Cl2 (0.1 eq) was added at RT, degassing under argon, 30 min, RT, resulting reaction mixture was gradually warmed to 60° C. for 10 min and stirred for 4 h. One polar product spot was observed by TLC. The reaction mass was quenched with water and extracted with EtOAc (2×30 mL). The combined organic layer was washed with water and dried over anhydrous Na2SO4, filtered and concentrated under reduced pressure to afford crude material which was purified by silica gel column chromatography [using 100-200 mesh, eluting with 30% EtOAc-hexane] to afford 300 mg of 2 as yellow thick syrup.

Preparation of UV-0241:

2 (300 mg, 0.32 mmol), 1,4-dioxane (5 mL), 4M HCl in 1,4-dioxane (3.0 mL), 0° C. for 20 min, gradually warmed to RT for 15 min, stirred for 16 h. The reaction was monitored by TLC. LCMS indicated 81% product formation. The volatiles were removed under reduced pressure to obtain 130 mg of crude material. HPLC purification (column X-select CSH C-18 (250×19 mm, 5µ) (130 mg loading; CH3CN: 5 mM NH4HCO3; T/B %: 0.1/90, 2/90, 10/70, 20/35, 25/10, 35/10; as mobile phase; flow rate: 15 mL/min) afforded 25 mg of UV-0241 as tan solid, purity 97.16% by HPLC (column; X-select CSH C-18 (150×4.6 mm, 3.5 µm); RT 7.85 min; ACN:NH4OAc; 1.0 mL/min), [M+H]+ 462.1 by LCMS.

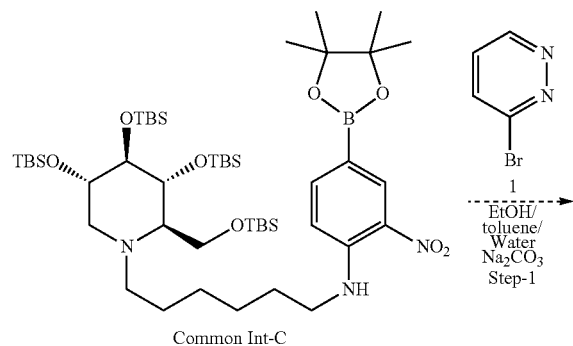

Common Int-C

Example 48. Synthesis of UV-0243

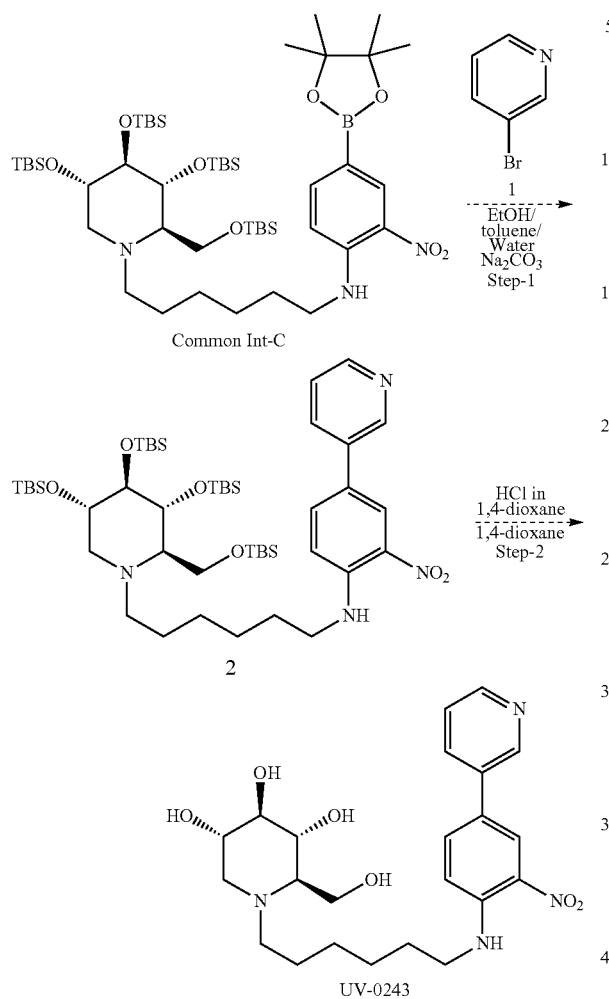

Preparation of 2:

Common Int-C (800 mg, 0.82 mmol), EtOH:toluene: water (1:1:1, 20 mL), 1 (1.0 eq), RT; reaction mixture was purged under argon at RT for 30 min; Na2CO3 (3.0 eq), Pd(dppf)2Cl2 (0.1 eq), was added and again purged under argon for 30 min; gradually warmed to 60° C. for 10 min and stirred for 4 h. A polar spot was observed by TLC. The reaction mixture was quenched with water and extracted with EtOAc (2×30 mL). The combined organic layer was washed with water and dried over anhydrous Na2SO4, filtered and concentrated under reduced pressure to afford crude material which was purified by silica gel column chromatography [using 100-200 mesh, eluting with 30% EtOAc-hexane] to afford 320 mg of 2 as yellow thick syrup.

Preparation of UV-0243:

2 (320 mg, 0.34 mmol) in 1,4-dioxane (5 mL) was added 4M HCl in 1,4-dioxane (3.2 mL), 0° C. for 20 min; gradually warmed to RT for 20 min and stirred for 16 h. The reaction was monitored by TLC. LCMS indicated 93% product formation. The volatiles were removed under reduced pressure to obtain 150 mg of crude material which was triturated with diethylether (2×50 mL) and dried to afford 50 mg of UV-0243. HPLC purity before trituration (column; X-select CSH C-18 (150×4.6 mm, 3.5 µm); RT 8.19 min; ACN: 5 mM NH4HCO3; 1.0 mL/min) 93.49% with [M+H]+ 461.2 by LCMS.

Example 49. Synthesis of UV-0244

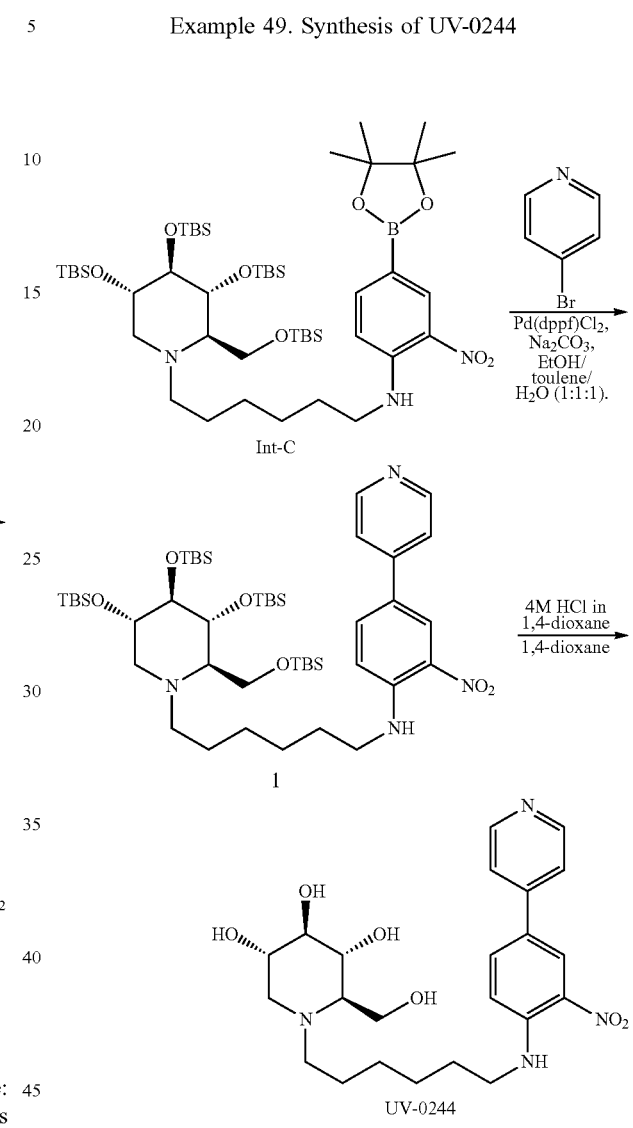

Preparation of 1:

To a stirred solution of Int-C (800 mg, 0.82 mmol) in EtOH:toluene:water (1:1:1, 20 mL), was added 4-bromopyridine (1.0 eq) at RT, reaction mixture was purged under argon at RT for 30 min, Na2CO3 (3.0 eq), Pd(dppf) 2Cl2 (0.1 eq), was added and again purged under argon for 30 min; gradually warmed to 60° C. for 10 min and stirred for 4 h. One polar product was observed by TLC. The reaction mass was quenched with water and extracted with EtOAc (2×30 mL). The combined organic layer was washed with water and dried over anhydrous Na2SO4, filtered and concentrated under reduced pressure to afford crude material which was purified by silica gel column chromatography [using 100-200 mesh, eluting with 30% EtOAc-hexane] to afford 300 mg of 1 as yellow viscous syrup.

Preparation of UV-0244:

To a stirred solution of 1 (300 mg, 0.32 mmol) in 1,4-dioxane (5 mL) was added 4M HCl in 1,4-dioxane (3.0 mL), 0° C. for 20 min under argon atmosphere; gradually warmed to RT for 20 min and stirred for 16 h. The reaction was monitored by TLC. LCMS indicated 95% product formation. The volatiles were removed under reduced pressure to obtain 150 mg of crude material which was triturated with diethylether (2×50 mL) and dried to afford 50 mg of UV-0244. HPLC purity before trituration (column; X-select CSH C-18 (150×4.6 mm, 3.5 µm); RT 8.12 min; ACN: 5 mM NH4HCO3; 1.0 mL/min) 95.08% with [M+H]+ 461.2 by LCMS.

Example 50. Synthesis of UV-0098

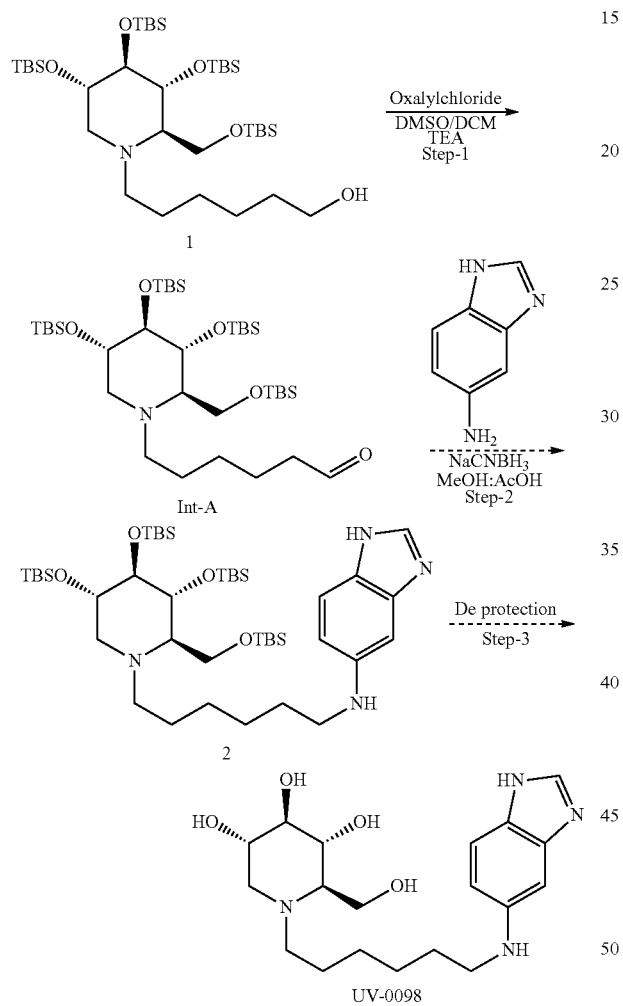

Preparation of 2:

Int-A (prepared from hydroxyl precursor as described above, 500 mg, 0.69 mmol), MeOH (15 ml), 3H-Benzoimidazol-5-ylamine (0.8 eq), AcOH (Cat.), NaCNBH3 (1.5 eq), reacted at RT. After 16 h, starting material was consumed and one major non-polar product spot was observed by TLC. The volatiles were removed under reduced pressure to afford crude material which was purified by silica gel (100-200 mesh) flash column chromatography [eluting with 20% EtOAc-hexane] to afford 200 mg of 2 as colorless thick syrup. Another preparation by similar process yielded 90 mg. These were used without further purification for the subsequent step.

Preparation of UV-0098:

2 (90 mg, 0.10 mmol), 1,4-dioxane (3 ml), 4M HCl in 1,4-dioxane (1.0 mL), mixed at 0° C. then raised to RT. After 16 h, LCMS suggested 30% product formation. The volatiles were removed under reduced pressure to afford 35 mg of crude. Another preparation with 2 (200 mg), 1,4-dioxane (10 ml), 4M HCl in 1,4-dioxane (3.0 mL) afforded 150 mg of crude.

Purification of combined lots by preparative HPLC afforded 15 mg of UV-0098 as a white solid with 96.18% purity by HPLC, [M+H]+ 379.4 by LCMS.

Example 51. Synthesis of UV-0099

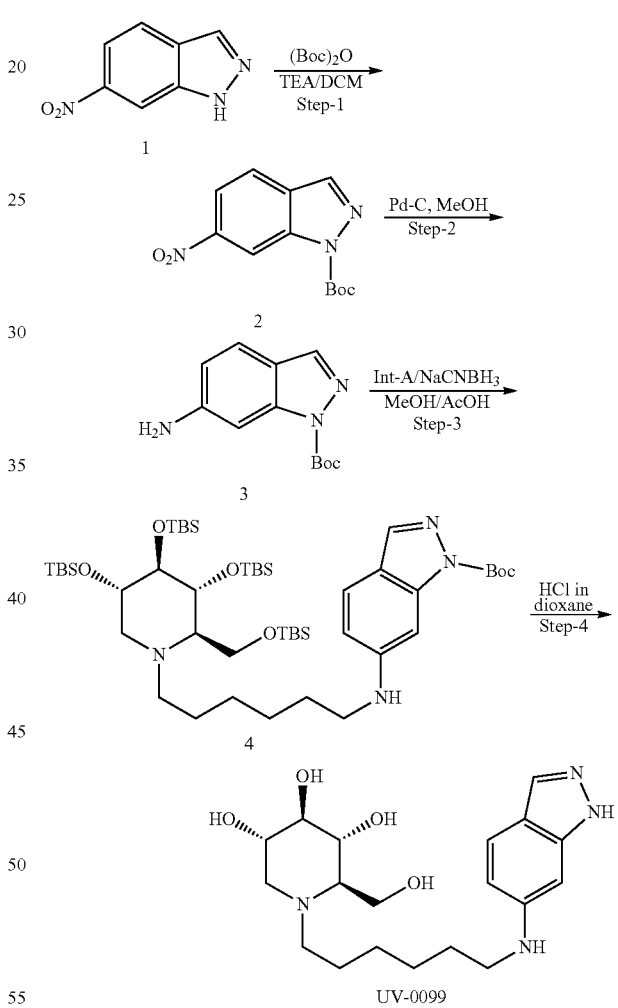

Preparation of Int-A

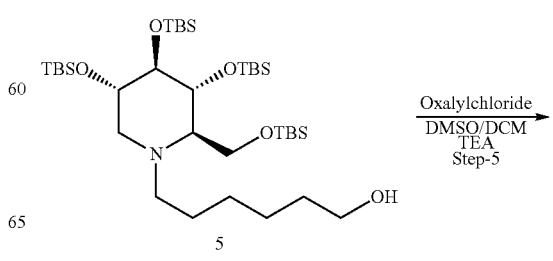

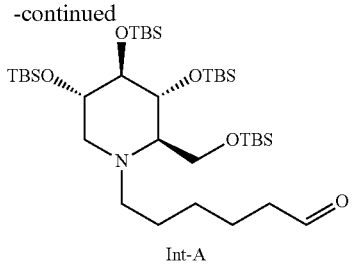

Preparation of 2:

1 (1.0 g, 6.13 mmol), DCM (30 mL), DMAP (cat.), TEA (3 eq), (Boc)2O (1.2 eq), reacted at RT. After 16 h a non-polar product was observed by TLC. The reaction was quenched with ice cold water and extracted with DCM (2×10 mL). The organic layer was dried over anhydrous Na2SO4, filtered and concentrated under reduced pressure to afford crude material which was purified by silica gel column chromatography [using 100-200 mesh, eluting with 10% EtOAc-hexane] to afford 1 g of 2.

Preparation of 3:

2 (500 mg, 1.90 mmol), MeOH (15 mL), 10% Pd/C (200 mg), hydrogen gas balloon pressure, was reacted at RT. After 6 h a polar product was observed by TLC. The reaction was filtered and the filtrate was concentrated to afford 300 mg of 3.

Preparation of 4:

Int-A (prepared from hydroxyl precursor as described above, 929 mg, 1.29 mmol), MeOH (20 mL), 3 (0.8 eq), AcOH (Cat.), NaCNBH3 (1.5 eq), was reacted at RT. After 16 h, a non-polar product was observed by TLC. The volatiles were concentrated under reduced pressure; residue was quenched with water and extracted with EtOAc (2×30 mL). The combined organic layer was washed with water and dried over anhydrous Na2SO4, filtered and concentrated under reduced pressure to afford crude material which was purified by silica gel column chromatography [using 100-200 mesh, eluting with 10% EtOAc-hexane] to afford 300 mg of 4.

Preparation of UV-0099:

4 (300 mg, 0.32 mmol), 1,4-Dioxane (5 mL), 4M HCl in 1,4-Dioxane (2 mL), mixed at 0° C. then raised to RT. After 16 h, crude LCMS showed 95% product formation. The volatiles were removed under reduced pressure to obtain 200 mg of crude material. Preparative HPLC afforded 47.3 mg of UV-0099 as a brown thick syrup with 96.87% purity by HPLC, [M+H]+ 379.1 by LCMS.

Example 52. Synthesis of UV-0100

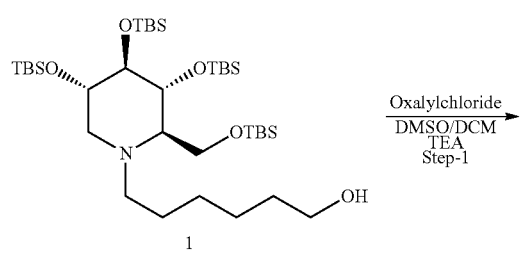

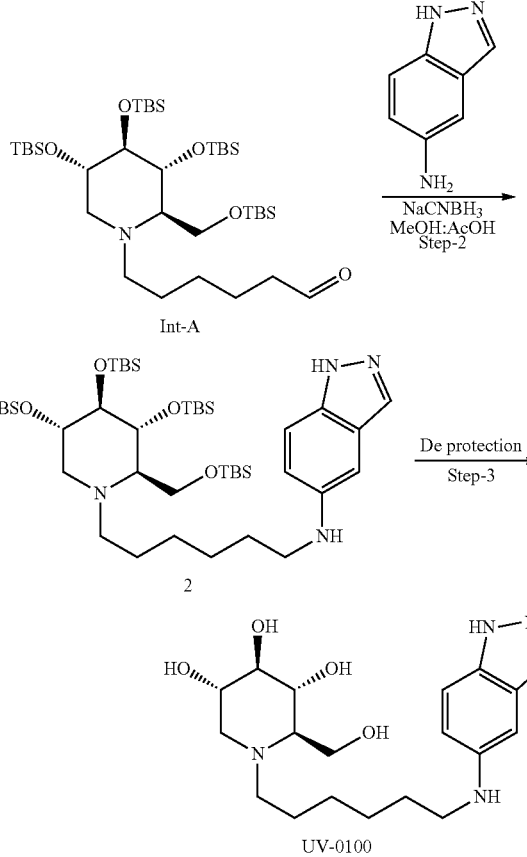

Preparation of 2:

Int-A (prepared from hydroxyl precursor, 1.2 eq), MeOH (5 ml), 1H-indazol-5-amine (0.03 g, 0.22 mmol), AcOH (Cat.), NaCNBH3 (1.5 eq) were reacted at RT. After 16 h, starting material was consumed and one major non-polar product was observed by TLC. The volatiles were removed under reduced pressure to afford crude material which was purified by silica gel (100-200 mesh) flash column chromatography [eluting with 20% EtOAc-hexane] to afford 80 mg of 2 as colorless thick syrup.

Preparation of UV-0100:

2 (80 mg, 0.09 mmol), 1,4-dioxane (3 ml), 4M HCl in 1,4-dioxane (1.0 mL), mixed at 0° C. then raised to RT. After 16 h, LCMS indicated 75% product formation. The volatiles were removed under reduced pressure. Preparative HPLC afforded 25.0 mg of UV-0100 as white solid with 97.52% purity by HPLC, [M+H]+ 379.5 by LCMS.

Example 53. Synthesis of UV-0101

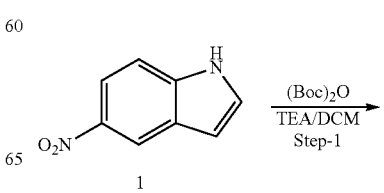

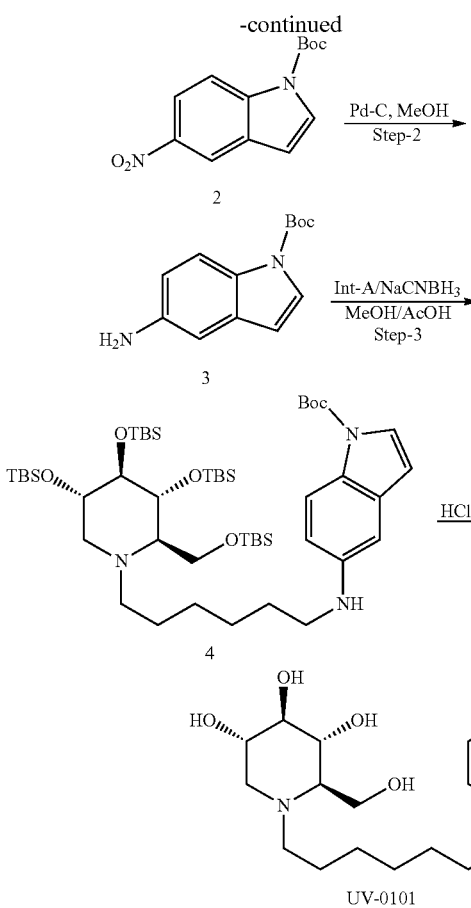

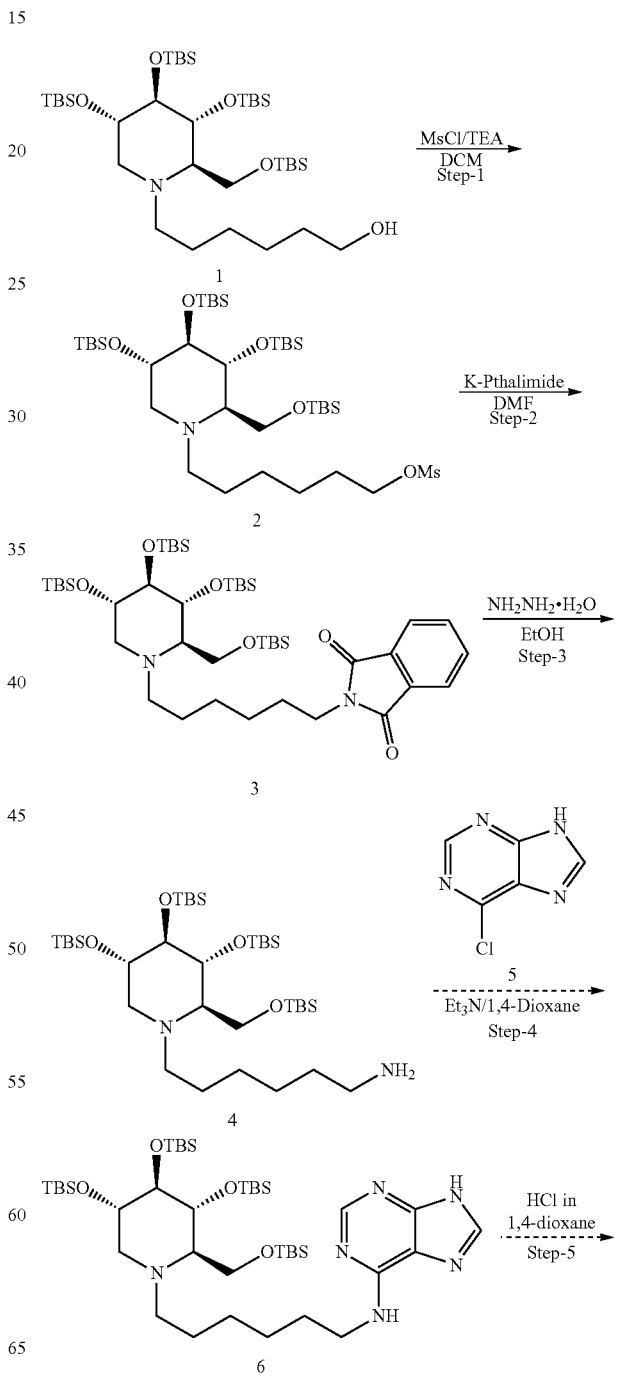

Preparation of 2:

1 (1.0 g, 6.17 mmol), DCM (30 mL), DMAP (cat.), TEA (3 eq), (Boc)2O (1.2 eq) reacted at RT. After 16 h a non-polar product was observed by TLC. The reaction was quenched with ice cold water and extracted with DCM (2×10 mL). The organic layer was dried over anhydrous Na2SO4, filtered and concentrated under reduced pressure to afford crude material which was purified by silica gel column chromatography [using 100-200 mesh, eluting with 10% EtOAc-hexane] to afford 1 g of 2.

Preparation of 3:

2 (100 mg, 0.38 mmol), ETOH:H2O (1; 1, 5 mL), Fe powder (3 eq), NH4Cl (5 eq), mixed at RT then raised to 80° C. After 2 h, a polar product was observed by TLC. The reaction was quenched with ice cold water and extracted with EtOAc (2×10 mL). The organic layer was dried over anhydrous Na2SO4, filtered and concentrated under reduced pressure to afford crude material which was purified by silica gel column chromatography [using 100-200 mesh, eluting with 15% EtOAc-hexane] to afford 50 mg of 3. Repeat preparation with 500 mg of 2 yielded 250 mg of 3.

Preparation of 4:

Int-A (929 mg, 1.29 mmol), MeOH (20 mL), 3 (0.8 eq), AcOH (cat.), NaCNBH3 (1.5 eq) reacted at RT. After 16 h a non-polar product spot was observed by TLC. The volatiles were concentrated under reduced pressure. The residue was quenched with water and extracted with EtOAc (2×50 mL). The combined organic layer was washed with water and dried over anhydrous Na2SO4, filtered and concentrated under reduced pressure to afford crude material which was purified by silica gel column chromatography [using 100-200 mesh, eluting with 10% EtOAc-hexane] to afford 220 mg of 4.

Preparation of UV-0101:

4 (220 mg, 0.23 mmol), 1,4-dioxane (4 mL), 4M HCl in 1,4-dioxane (2 mL), mixed at 0° C. then raised to RT. After 16 h, crude LCMS suggested 85% product formation. The volatiles were removed under reduced pressure to obtain 200 mg of crude material. Preparative HPLC afforded 12.0 mg of UV-0101 as brown syrup with 97.20% purity by HPLC, [M+H]+ 378.3 by LCMS.

Example 54. Synthesis of UV-0102

123

-continued

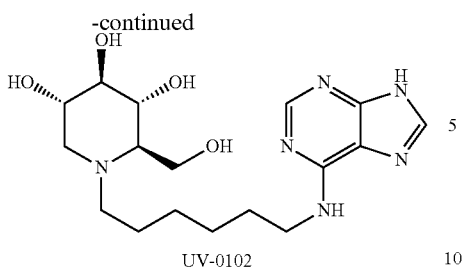

UV-0102

Preparation of 6:

Int-B (indicated in scheme as 4, prepared as described, 100 mg, 0.13 mmol), 1,4-dioxane (5 mL), TEA (1.0 mL), 5 (1.0 eq) mixed at RT and temperature raised to 90° C. After 24 h, a polar product was observed by TLC. Reaction was diluted with ice-cold water and extracted with EtOAc (2×10 mL). The combined organic layers were dried over Na2SO4 filtered and concentrated under reduced pressure to afford 50 mg (crude) of 6 as colorless thick syrup. A repeat preparation with 300 mg of 4 (Int-B, 0.39 mmol) afforded 300 mg of 6. Products were combined and preparative HPLC afforded 130 mg of 6.

Preparation of UV-0102:

2 (130 mg, 0.15 mmol), 1,4-dioxane (5 ml), 4M HCl in 1,4-dioxane (1.3 mL) mixed at 0° C. and raised to RT. After 16 h, crude LCMS suggested 85% product formation. The volatiles were removed under reduced pressure to afford 90 mg of crude material which was purified by preparative HPLC to afford 23.2 mg of UV-0102 as white solid with 99.42% purity by HPLC, [M+H]+ 381.4 by LCMS.

Example 55. Synthesis of UV-0104

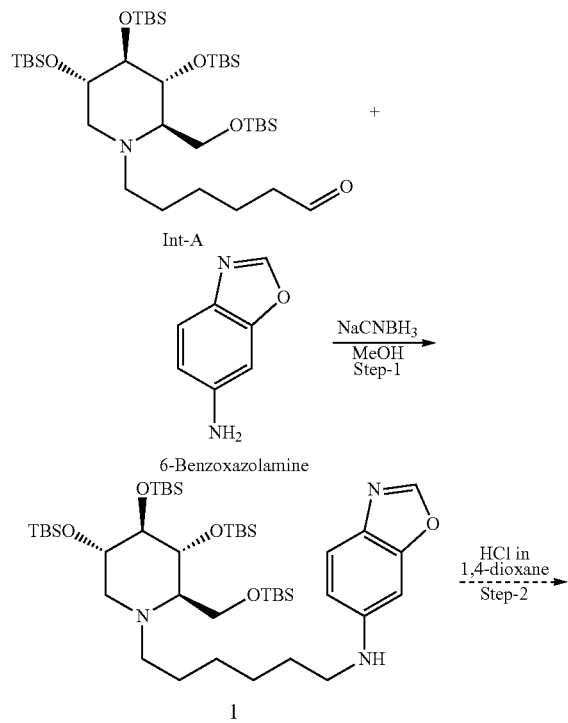

124

-continued

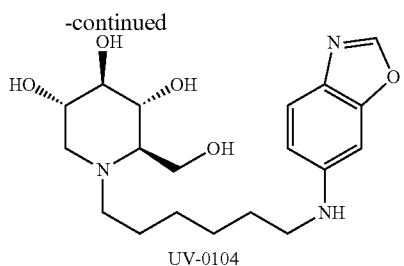

UV-0104

Preparation of 1:

Int-A (300 mg, 0.41 mmol), MeOH (10 ml), 6-benzoxazolamine (0.8 eq), AcOH (Cat.), NaCNBH3 (1.5 eq) reacted at RT. After 16 h, starting material was consumed and one major non-polar product was observed by TLC. The volatiles were removed under reduced pressure to afford crude material which was purified by silica gel (100-200 mesh) flash column chromatography [eluting with 20% EtOAc-hexane] to afford 200 mg (42% yield) of 1 as color less thick syrup. Another preparation with 1.2 g of Int-A afforded 800 mg of 1 as colorless thick syrup.

Preparation of UV-0104:

1 (100 mg, 0.10 mmol), THF (10 ml), CsF (5.0 eq), TBAF (cat) mixed at 0° C. then raised to RT. After 16 h, starting material was consumed and polar product spot observed by TLC. LCMS suggested 32% product formation. The volatiles were removed under reduced pressure to afford crude material. Another preparation was carried out with 200 mg of 1 (0.20 mmol). Products were combined and preparative HPLC followed by repeated lyophilisation afforded 12.5 mg of UV-0104 as colorless thick syrup with ~4.5% NH4OAc. Purity by HPLC 98.09%, [M+H]+ 380.4 by LCMS.

Example 56. Synthesis of UV-0105

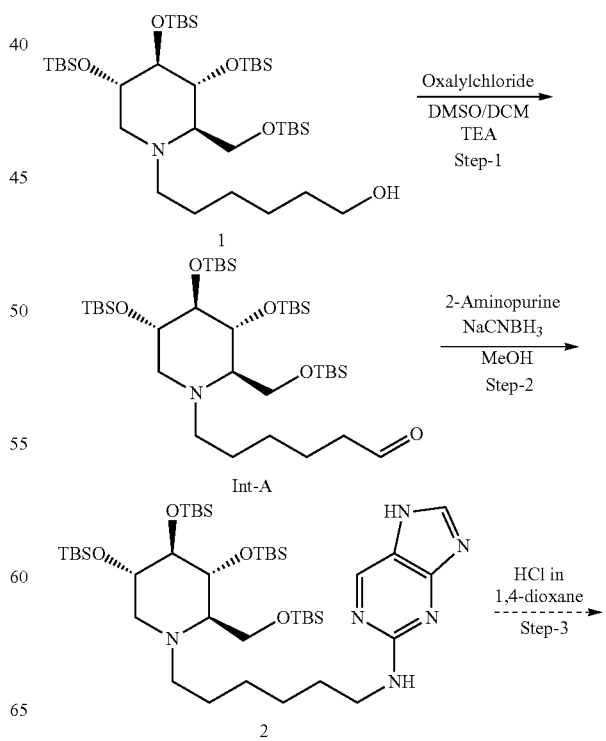

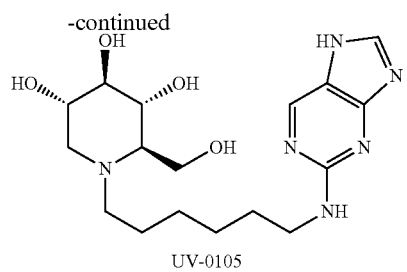

UV-0105

Preparation of 2:

9H-purin-2-amine (120 mg, 0.92 mmol), Int-A (1.2 eq), MeOH (20 ml), AcOH (cat), NaCNBH3 (1.5 eq) were reacted at RT. After 16 h, starting material was consumed and one major non-polar product was observed by TLC. The volatiles were removed under reduced pressure to crude material which was purified by column chromatography [using 00-200 mesh, eluting with 100% EtOAc] to afford 150 mg of 2 as color less thick syrup.

Preparation of UV-0105:

2 (150 mg, 0.16 mmol), 1,4-dioxane (3 ml), 4M HCl in 1,4-dioxane (1.5 mL), mixed at 0° C. then raised to RT. After 16 h, starting material was consumed and one polar product spot was observed by TLC. LCMS suggested 32% product formation. The volatiles were removed under reduced pressure to afford 100 mg of crude material and preparative HPLC purification afforded 8.1 mg of UV-0105 as colorless thick syrup, with 95.12% purity by HPLC, [M−H]− 379.2 by LCMS.

Example 57. Cytotoxicity and In Vitro Antiviral Activity

Cytotoxicity: To determine the cytotoxicity of the compounds in Vero cells, the CellTiter-Glo Luminescent Cell Viability Assay (Promega) was used. The compounds were tested at 6-8 concentrations in three replicates. Control conditions include vehicle-only treated cells to set 100% surviving cells, DMSO-killed cells as a cell death-inducing control, and no cells for 0% surviving cells. Cytotoxicity is measured after 3-5 days in culture by the change/decrease in relative light units (RLUs) in each sample which reflects the amount of ATP present (an indicator of metabolically active cells).

The 50% cellular cytotoxicity (CC50) value is calculated based on the RLUs of the compound-treated samples using vehicle-only control as 100% survival and no cells as 0% survival.

In vitro antiviral activity: To test the ability of the compounds to reduce viral replication, virus yield assay performed and the supernatant samples generated from the virus-infected Vero cells incubated with different concentrations of each small-molecule subsequently enumerated using a standard plaque. The compounds were tested at 6 concentrations against dengue virus (DENV serotype 2, strain New Guinea C) or Venezuelan Equine Encephalitis Virus (VEEV TC-83 stain). The assay is used to determine the reduction in titer of virus after growth in the presence of predetermined concentrations of compound. In the yield assay, the concentrations tested started at 125 μM with two-fold dilutions and each concentration was tested in duplicate. Compound dilutions were added to cells at 1 hour prior to infection, virus was added to monolayer for infection between 3 and 5 days (VEEV and DENV, respectively). After the incubation period, supernatants were harvested and clarified of cell debris, and subsequently analyzed for virus content using plaque assay. In the plaque assay for titer determination, Vero cells were seeded in 24-well plates and allowed to adhere overnight. The next day each of the harvested supernatants from the yield-reduction assay were serially diluted 10-fold, growth medium was removed and cells were infected with the dilutions of the supernatants for 1 h. For the VEEV assay, the inoculum was removed after 1 h and 1% low-melting agarose was added. After 2 days, the cells were fixed and stained with crystal violet. Plaques were either visible as clear spots in a purple cell layer or as dark purple spots on a light purple cell layer. The plaques were counted and the IC50 determined. For the DENY assay, after the infection 0.8% methylcellulose was added without removal of the inoculum. The plates were incubated for four days, cells fixed and permeabilized in an 80%/20% (v/v) mixture of ethanol and methanol. A DENV E-specific antibody (monoclonal antibody 4G2, obtained from ATCC) was added for one hour. After washing an HRP-conjugated goat anti-mouse antibody was added for one hour. Foci of viral infection were visualized with an insoluble peroxidase substrate (TrueBlue), plaques counted and the IC50 was calculated. A 4PL curve was used to generate 50% inhibitory concentration (IC50) based on percent reduction of virus yield compared to a wild-type titer (no compound control) and these were calculated using XLFit equation 205.

Table 3 presents cytotoxicity and in vitro antiviral activity (against Dengue and Venezuelan Equine Encephalitis Virus) results.

| Compound | CC$_{50}$ Cytotoxicity in Vero Cells | IC50 Dengue-2 (DENV2) | IC50 Venezuelan Equine Encephalitis TC-83 (VEEV) |
|---|---|---|---|
| UV-30 | ≥125 microM | 7 microM | 14 microM |
| UV-60 | 245 microM | 5 microM | 94.1 microM |

Example 58. Drug Likeness

Assays for drug likeness (solubility, microsomal stability, plasma protein binding, A-B efflux, cytochrome CYP450 3A4, hERG binding, and Ames) were carried out by Cerep (Washington USA, and France) using standard protocols for in vitro testing. Assay protocols are provided online at http://www.cerep.fecerep/users/pages/catalog/profiles/catalog.asp and Cerep standard procedures and concentrations were used for all assays.

In vivo pharmacokinetic parameters and oral bioavailability for UV-0060 was determined by Eurofins (Cerep Panlabs, Taiwan). A pharmacokinetic study following oral and intravenous administrations was performed using male Sprague-Dawley rats. Test article was formulated in 2% DMSO/0.9% NaCl and administered orally (PO) at 10 mg/kg and intravenously (IV) at 5 mg/kg to groups of 3 rats. The dosing volume was 10 mL/kg for PO and 5 mL/kg for IV. Rats weighing 220±20 g were used. Blood samples were harvested at 3, 10, 30, 60, 120, 240, 360, 720 and 1440 minutes after intravenous injection and at 10, 30, 60, 120, 240, 360, 720 and 1440 minutes after oral administration. Blood was collected in tubes coated with lithium heparin, mixed gently, then kept on ice and centrifuged at 2,500×g for 15 minutes at 4° C., within 1 hour of collection. The plasma was harvested and kept frozen at −80° C. until further processing. A plasma calibration curve from 3-10000 ng/mL was generated using oxybutynin as internal standard. Aliquots of drug-free plasma were spiked with the test compound at the specified concentration levels. Plasma samples were processed using acetonitrile precipitation and analyzed by HPLC/MS/MS. The spiked plasma samples were processed together with the unknown plasma samples using the same procedure. HPLC/MS/MS analysis was carried out with electrospray ionization in positive ion mode with multiple reaction monitoring. HPLC column was Agilent Poroshell 120 EC-C18 column 2.7 μm (3.0×50 mm, 23° C.) with an acetonitrile/water/formic acid mobile phase gradient. Standards data were fitted linearly with a 1/x2 weighting.

Table 4 presents results of drug likeness assays for UV-5 and UV-0060.

TABLE 4

| UV-5 | UV-0060 |
| --- | --- |
| Molecular weight: 424.46 | Molecular weight: 450.50 |
| Aqueous solubility: >112 mg/mL in acidified water pH~4. | Aqueous solubility in gastric and intestinal fluids both >200 microM |
| Plasma t½: ~4 h (mice), 1.62 h (guinea pig) | Human microsomal stability: t½ > 60 min |
| Clearance (guinea pig): 232.55 mL/min/kg | Human plasma protein binding: 88% (at 10 microM) |
| Vss (guinea pig): 16.89 L/kg | A-B Efflux (Caco2): Papp~0.3 |
| Oral Bioavailability (mice): 80% | CYP450 3A4 inhibition: none (0.2% at 10 uM) |
| | hERG binding: not significantly different to negative control (3% at 10 uM) |
| | Ames: negative with or without S9 activation |

Table 5 presents results for in vivo ADME parameters in rodent species.

TABLE 5

| UV-5 | UV-0060 |
| --- | --- |
| Mouse (single dose, tested IV, oral routes): | Rat (single dose, tested IV, oral routes): |
| $T_{max}$: 1 h | $T_{max}$: 2.2 h |
| $C_{max}$: 14369-14399 ng/mL | CL: 72.9 mL/min/kg |
| $T_{1/2}$: 4.09-8.96 h | $T_{1/2}$: 2.8 h (IV), 2.2 h (PO) |
| Bioavailability: 80% (oral) | Oral Bioavailability: 6% |
| Guinea pig (single dose, tested IV, SQ, IM routes): | |
| Tmax: 0.75-1.13 h | |
| Cmax: 2317-3793 ng/mL | |
| T½: 1.62-3.99 h | |
| Bioavailability: 187-198% (IM, SC) | |

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

What is claimed is:
1. A compound of formula IA:

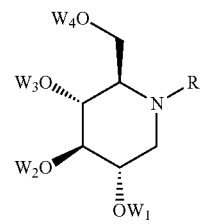

or a pharmaceutically acceptable salt thereof, wherein R is
a)

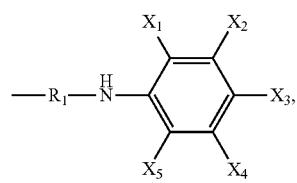

wherein optionally, at least one CX group in

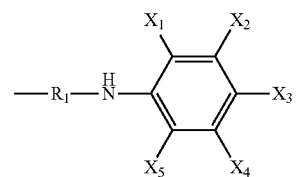

is replaced with N; or
b)

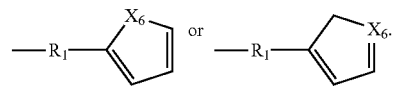

wherein $X_6$ is O or S; and
wherein each of $W_1$-$W_4$ is independently H or a $C_1$-$C_3$ alkyl group;
$R_1$ is a $C_1$-$C_{12}$ alkyl group; and
wherein each of $X_1$-$X_5$ is independently selected from the group consisting of H, $N_3$, $NO_2$, $NH_2$,

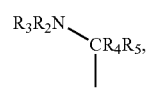

and a group comprising a heteroatom containing ring,
wherein each of $R_2$ and $R_3$ is independently selected from the group consisting of H, $C_1$-$C_3$ alkyl, and $C_1$-$C_3$ hydroxyalkyl; and $R_4$ and $R_5$ are each H, or $R_4$ and $R_5$ are together =N—OH, provided that at least one of $X_1$-$X_5$ is

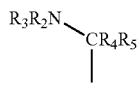

or the group comprising a heteroatom containing ring; or wherein each of $X_1$-$X_5$ is independently selected from the group consisting of H, $N_3$, $NO_2$, and $NH_2$, and wherein two of $X_1$-$X_5$, which are adjacent, form a heteroatom containing ring.

2. The compound of claim 1, wherein R is

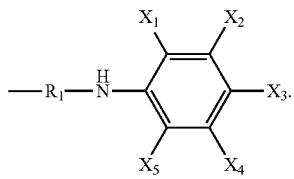

3. The compound of claim 2, wherein one of $X_1$-$X_5$ is

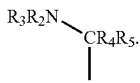

4. The compound of claim 3, wherein $R_2$ and $R_3$ are each methyl and $R_4$ and $R_5$ are each H; or wherein $R_2$ is $C_1$-$C_3$ hydroxyalkyl and each of $R_3$, $R_4$ and $R_5$ is H; or wherein $R_2$ and $R_3$ are each H and $R_4$ and $R_5$ are together =N—OH.

5. The compound of claim 2, wherein one of $X_1$-$X_5$ is the group comprising a heteroatom containing ring, wherein the heteroatom containing ring comprises at least one ring forming atom selected from N and O; wherein the heteroatom containing ring is directly bound to the ring of R or is bound to the ring of R through a $C_1$-$C_3$ alkyl group; or wherein the heteroatom containing ring is a three, four, five, six or seven membered ring.

6. The compound of claim 5, wherein the heteroatom containing ring is a conjugated ring.

7. The compound of claim 5, wherein the heteroatom containing ring is a non-conjugated ring.

8. The compound of claim 2, wherein the group comprising a heteroatom containing ring is selected from

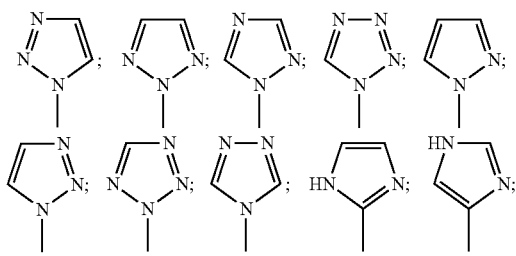

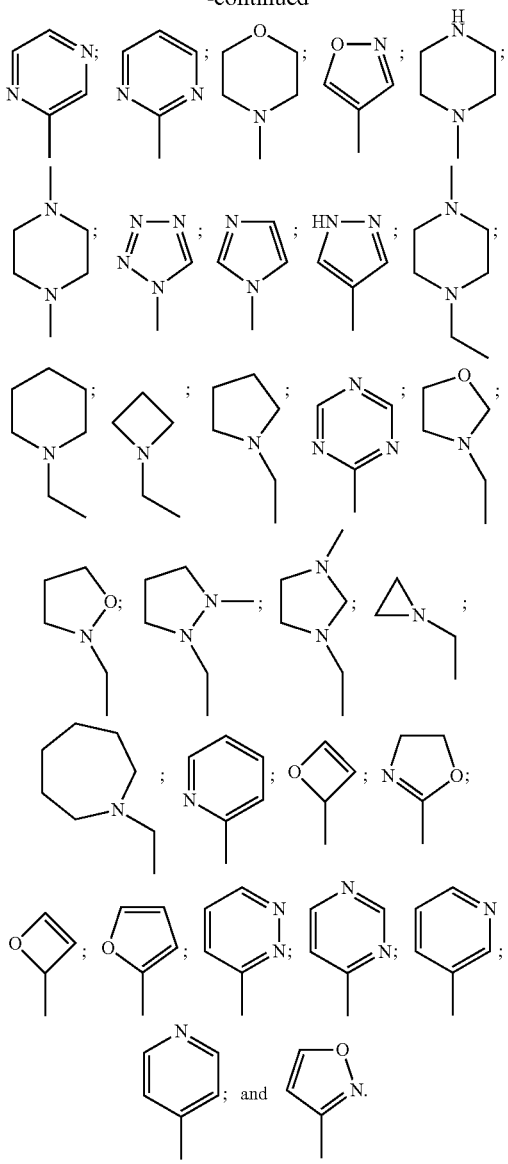

9. The compound of claim 2, wherein $X_2$ or $X_3$ is

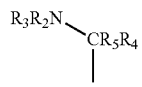

or the group comprising a heteroatom containing ring.

10. The compound of claim 9, wherein $X_4$ and $X_5$ are each independently H or $NO_2$, wherein at least one of $X_4$ and $X_5$ is H.

11. The compound of claim 9, wherein $X_3$ is

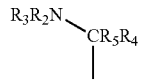

or the group comprising a heteroatom containing ring.

12. The compound of claim 11, wherein $X_5$ is H or $NO_2$.

13. The compound of claim 2, wherein $X_1$ and $X_2$, $X_2$ and $X_3$, $X_3$ and $X_4$, or $X_4$ and $X_5$ together form a heteroatom containing ring.

14. The compound of claim 13, wherein R is

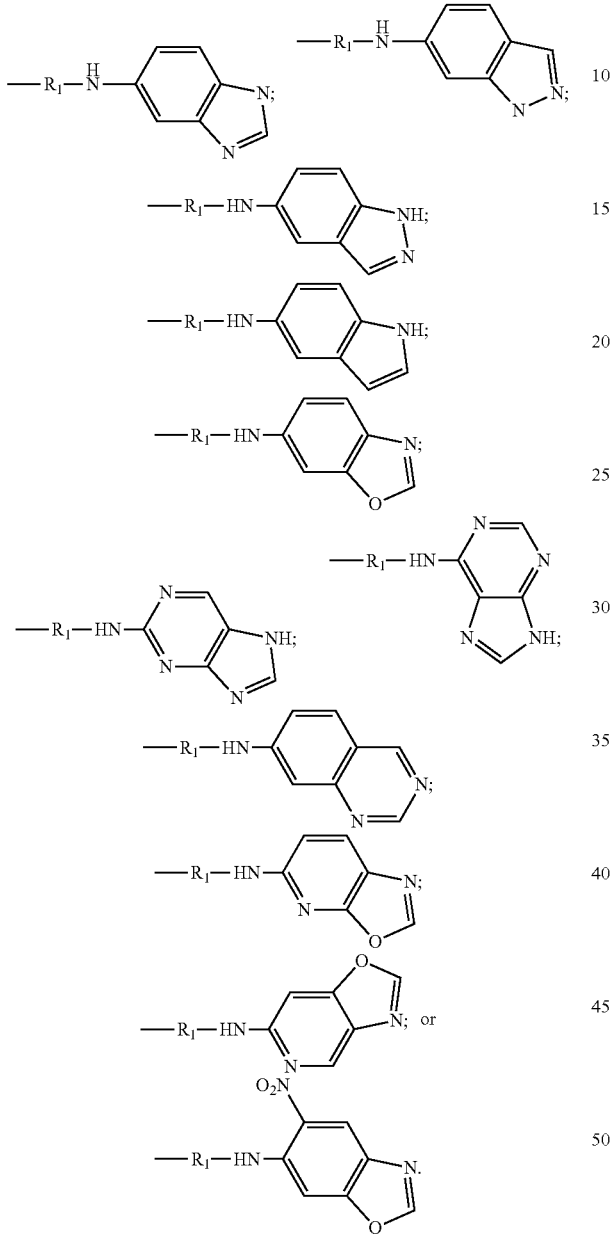

15. The compound of claim 13, wherein any of $X_1$-$X_5$ which do not form the heteroatom containing ring, are each H.

16. The compound of claim 1, wherein R is

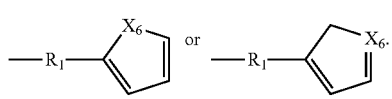

17. The compound of claim 16, wherein $R_1$ is $C_6$-$C_{10}$ alkyl.

18. The compound of claim 1, which is

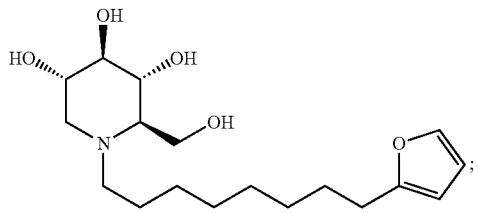

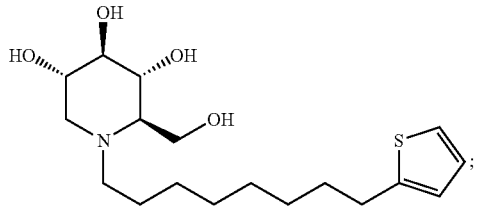

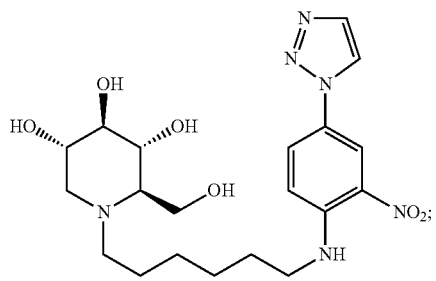

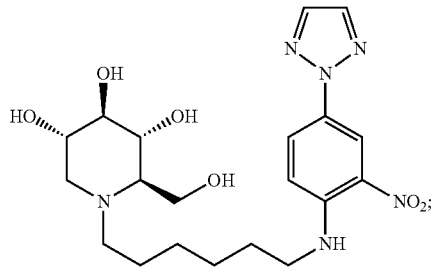

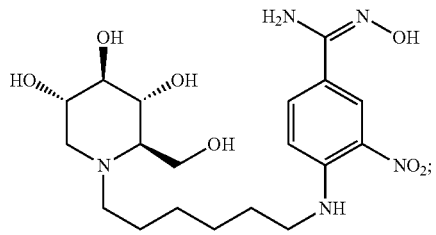

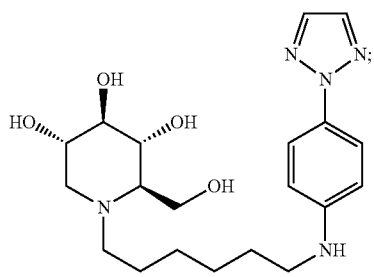

133
-continued
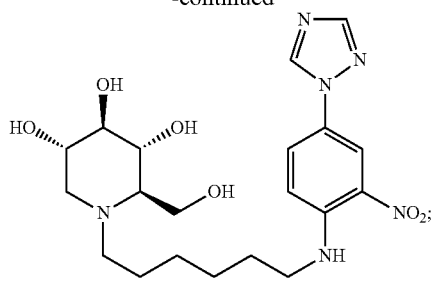
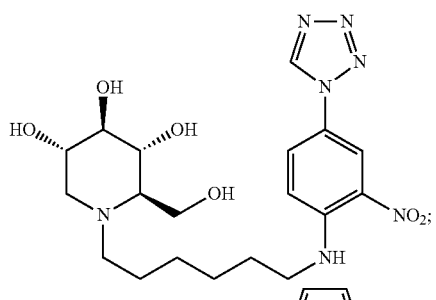
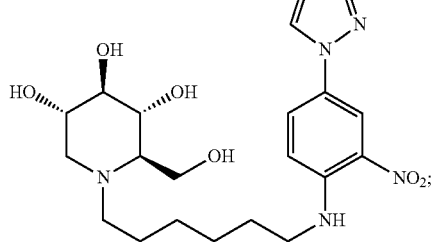
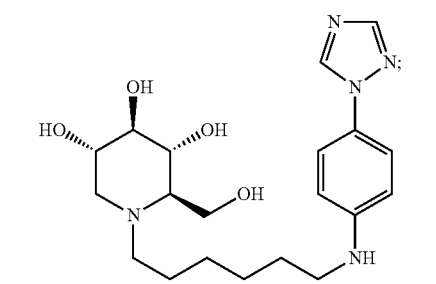
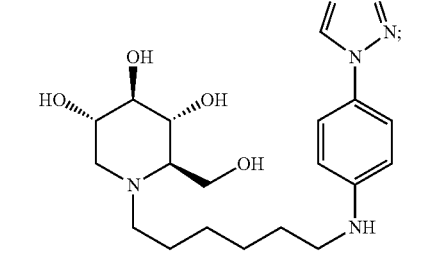
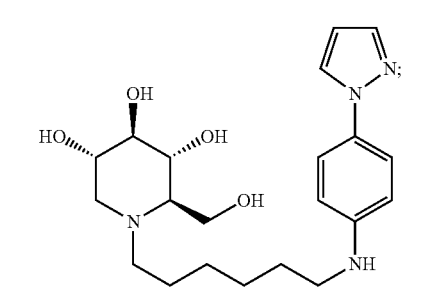
134
-continued
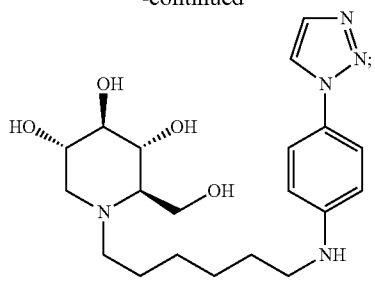
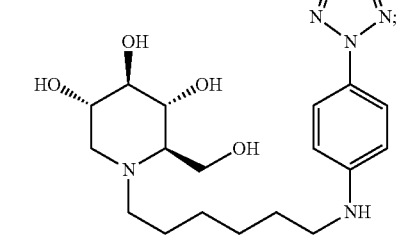
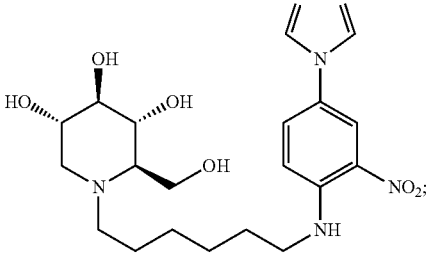
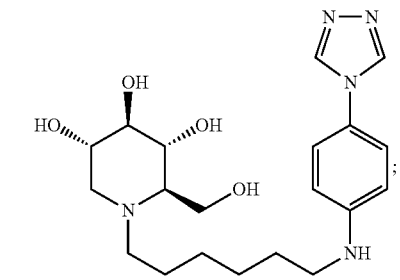
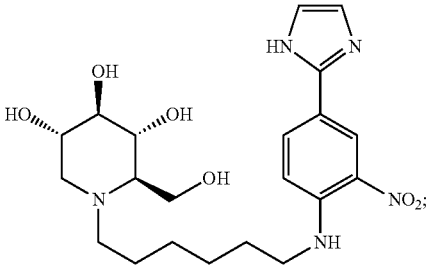
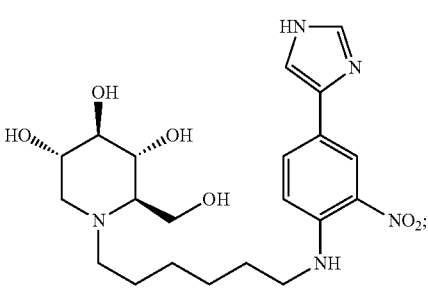

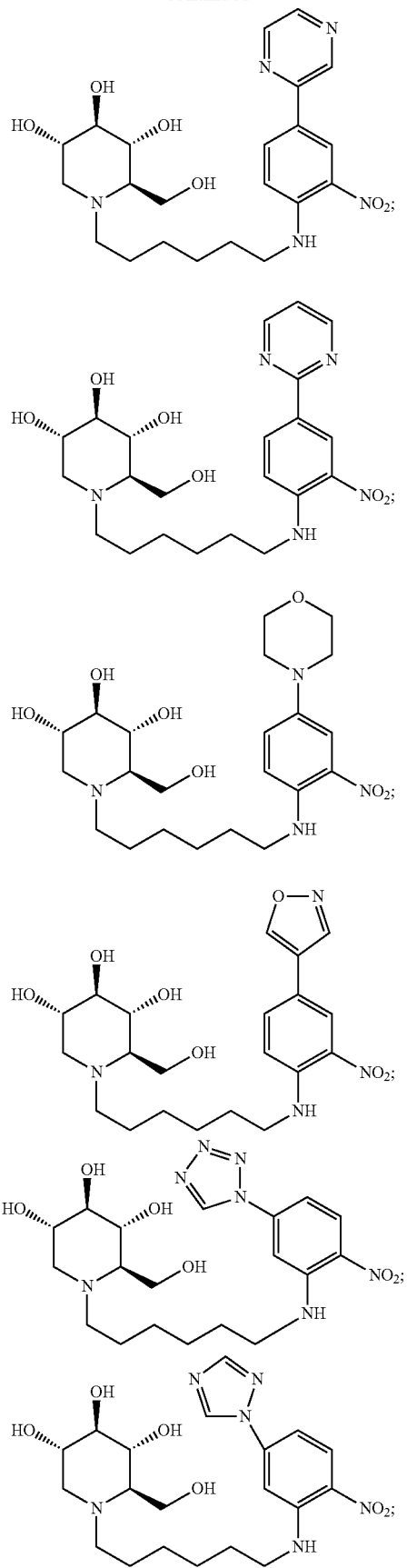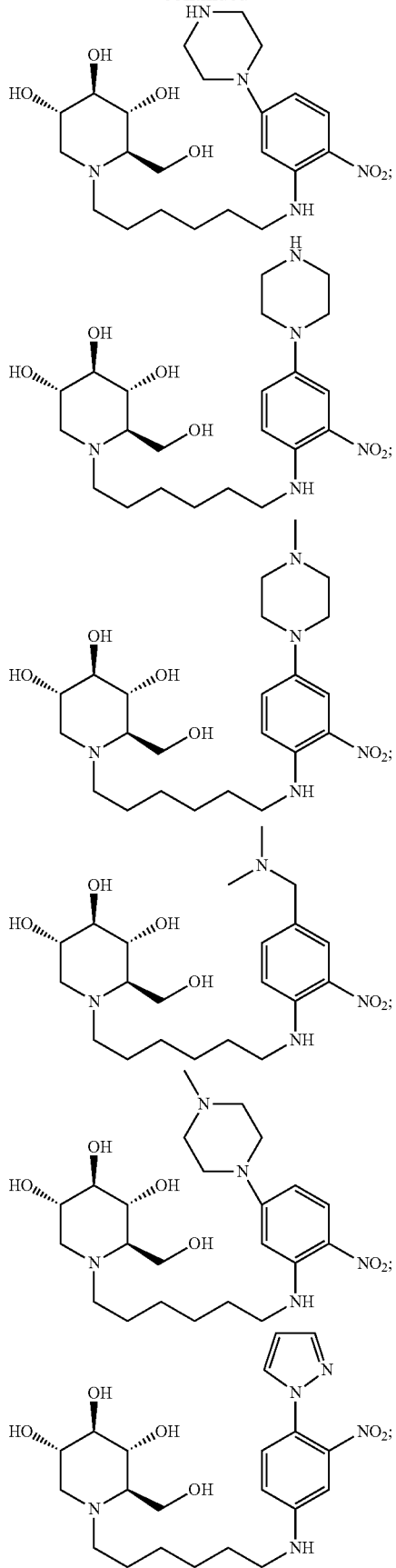

137
-continued
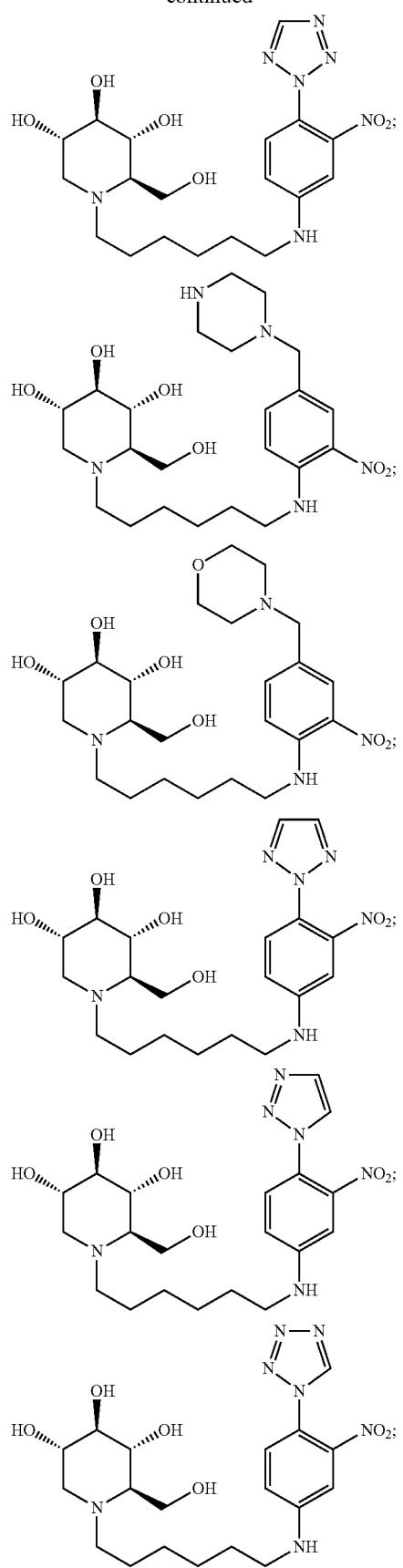
138
-continued
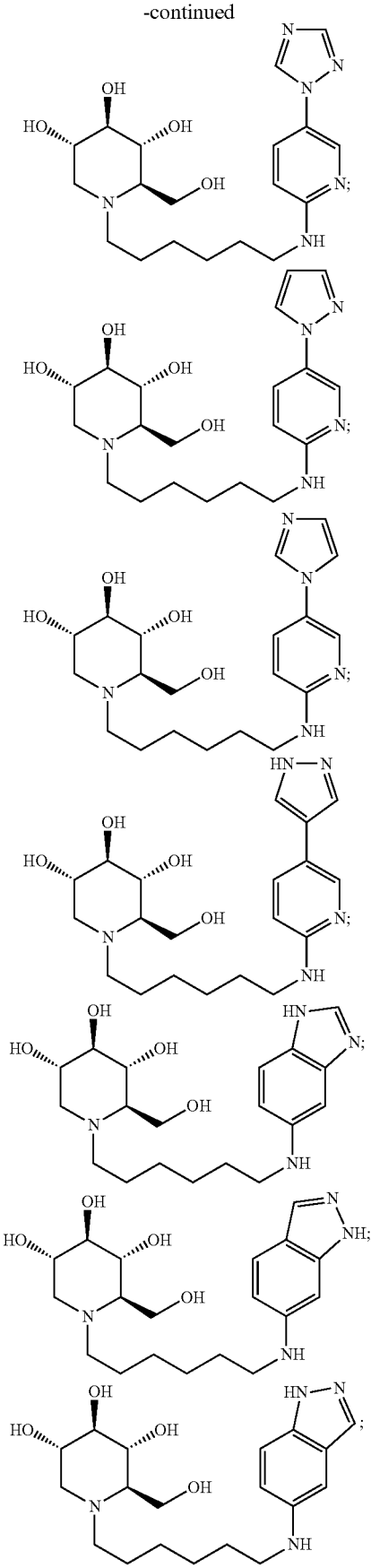

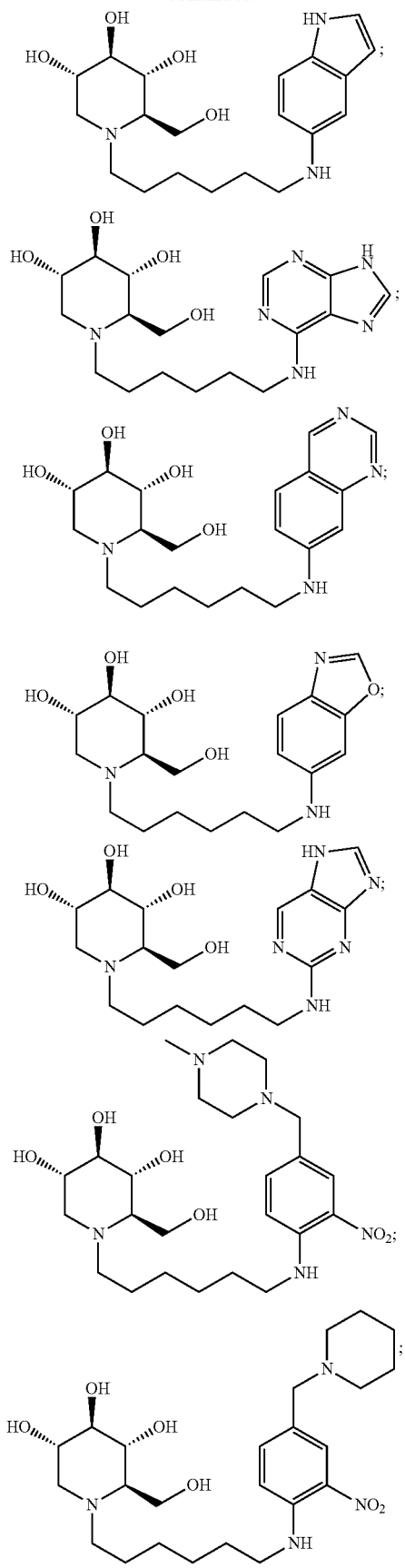
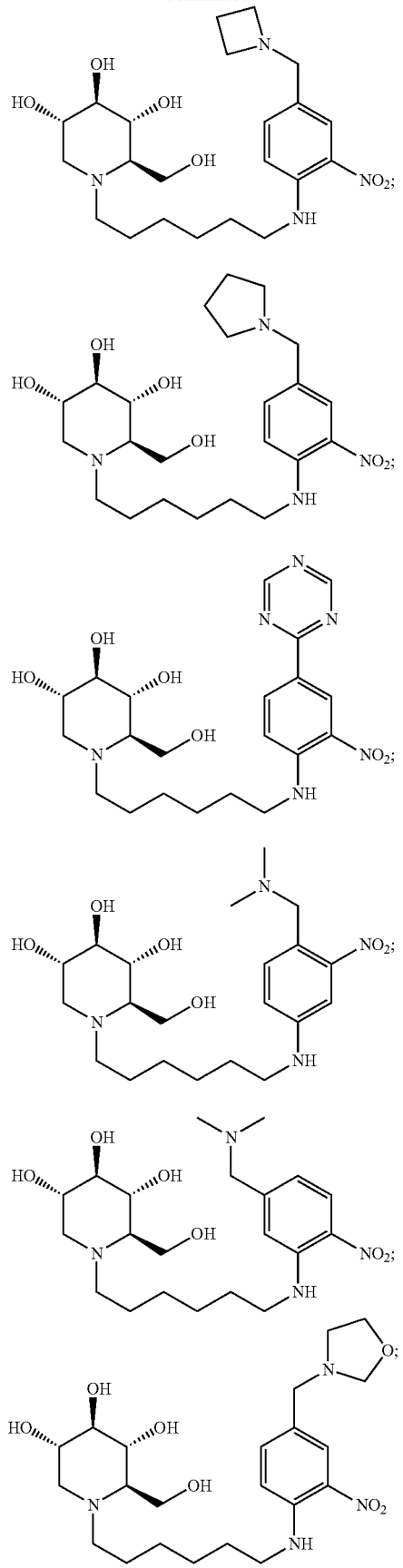

-continued
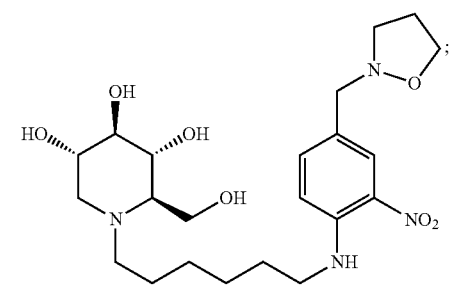
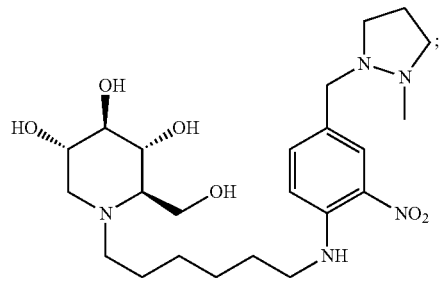
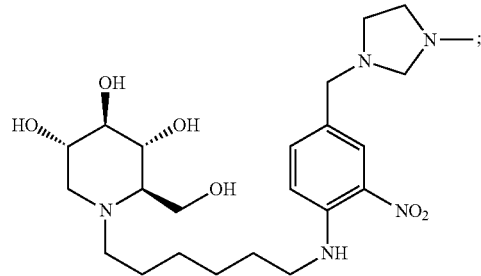
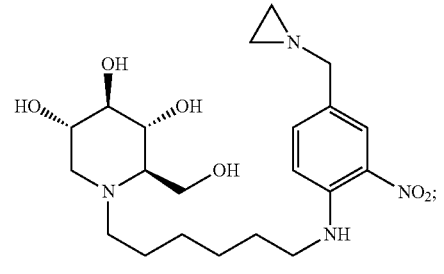
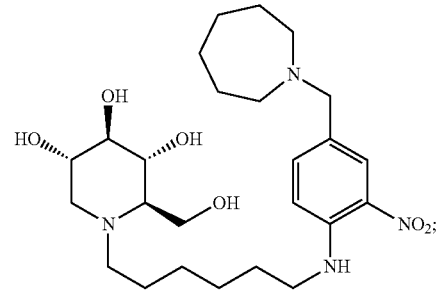
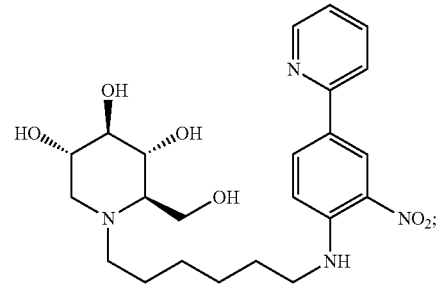
-continued
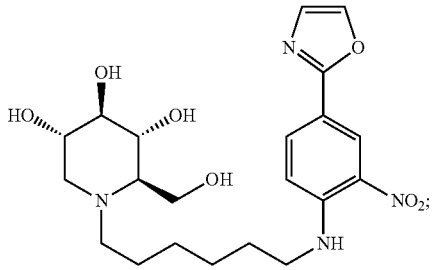
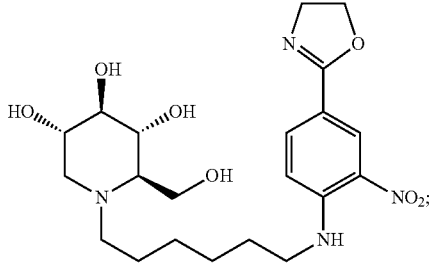
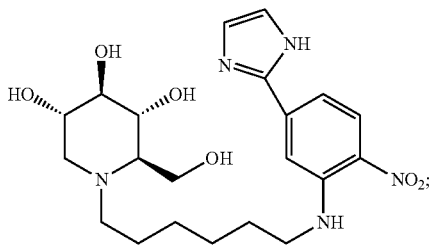
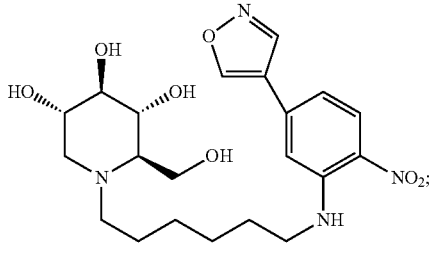
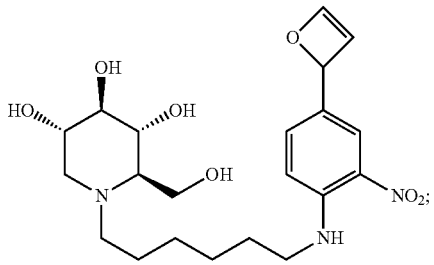
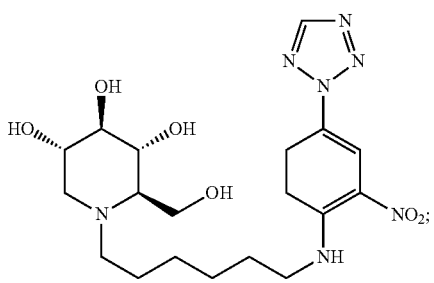

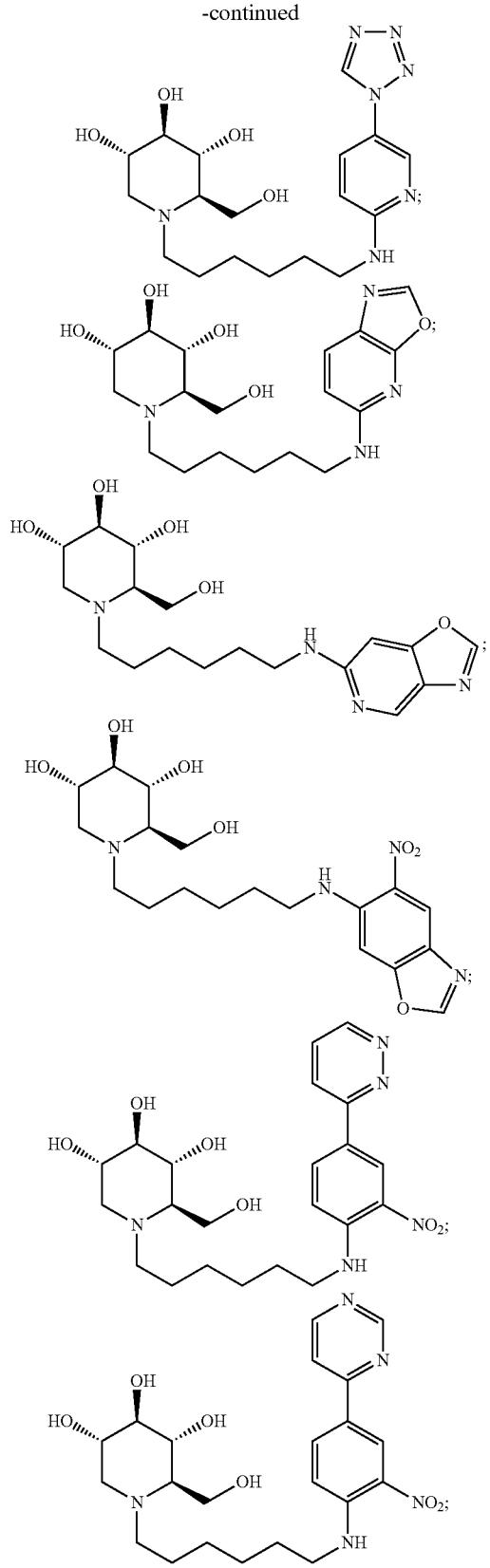
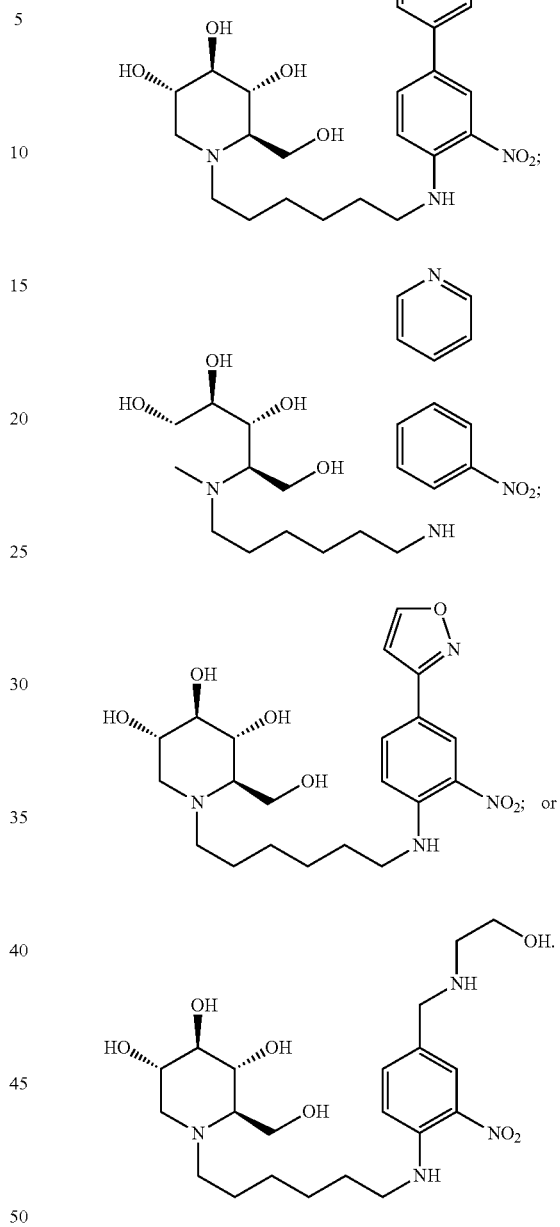

19. A pharmaceutical composition comprising i) the compound of claim 1 and ii) a pharmaceutically acceptable excipient.

20. The pharmaceutical composition of claim 19, wherein the composition is an oral pharmaceutical composition.

21. A method of treating a Dengue virus viral infection or a togaviridae virus viral infection in a subject in need thereof, the method comprising administering an effective amount of a compound of claim 1 to the subject to treat the viral infection.

* * * * *

UNITED STATES PATENT AND TRADEMARK OFFICE
CERTIFICATE OF CORRECTION

PATENT NO. : 10,428,022 B2
APPLICATION NO. : 15/524535
DATED : October 1, 2019
INVENTOR(S) : Ramstedt et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 190 days.

Signed and Sealed this
Eighth Day of December, 2020

Andrei Iancu
*Director of the United States Patent and Trademark Office*